(12) United States Patent
Tsuyama et al.

(10) Patent No.: US 9,159,356 B2
(45) Date of Patent: Oct. 13, 2015

(54) NON-RESONANT TWO-PHOTON ABSORPTION RECORDING MATERIAL, NON-RESONANT POLYMER TWO-PHOTON ABSORPTION OPTICAL INFORMATION RECORDING MEDIUM, AND RECORDING/REPRODUCING METHOD

(71) Applicant: FUJIFILM Corporation, Minato-ku, Tokyo (JP)

(72) Inventors: Hiroaki Tsuyama, Kanagawa (JP); Masaomi Makino, Kanagawa (JP); Hidehiro Mochizuki, Kanagawa (JP); Toshio Sasaki, Kanagawa (JP); Tatsuo Mikami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/078,980

(22) Filed: Nov. 13, 2013

(65) Prior Publication Data
US 2014/0078878 A1 Mar. 20, 2014

Related U.S. Application Data

(63) Continuation of application No. PCT/JP2012/062128, filed on May 11, 2012.

(30) Foreign Application Priority Data

| May 13, 2011 | (JP) | ................. | 2011-108698 |
| Jul. 13, 2011 | (JP) | ................. | 2011-154893 |
| May 10, 2012 | (JP) | ................. | 2012-108951 |

(51) Int. Cl.
*G11B 7/24* (2013.01)
*G11B 7/245* (2006.01)
(Continued)

(52) U.S. Cl.
CPC ................. *G11B 7/245* (2013.01); *B82Y 10/00* (2013.01); *C07C 69/76* (2013.01); *G02B 1/04* (2013.01); *G11B 7/2405* (2013.01); *G11B 7/24044* (2013.01); *G11B 2007/00457* (2013.01)

(58) Field of Classification Search
CPC ..................... G11B 7/245; G11B 2007/00457; G11B 7/2405; G11B 7/24044; B82Y 10/00; C07C 69/76; G02B 1/04
See application file for complete search history.

(56) References Cited

U.S. PATENT DOCUMENTS

| 2004/0245432 | A1 | 12/2004 | Takizawa |
| 2005/0173683 | A1 | 8/2005 | Marder et al. |

(Continued)

FOREIGN PATENT DOCUMENTS

| JP | 2004-518154 A | 6/2004 |
| JP | 2004-529913 A | 9/2004 |

(Continued)

OTHER PUBLICATIONS

Brott et al. "Near IR two photon induced polymerizations using either benzophenone or thioxanthone based photoinitiators", Poly. Preprints., vol. 42(1) pp. 675-676 (2001).*

(Continued)

*Primary Examiner* — Martin Angebranndt
(74) *Attorney, Agent, or Firm* — Sughrue Mion, PLLC

(57) ABSTRACT

The present invention provides a non-resonant two-photon absorption recording material containing a non-resonant polymer two-photon absorption compound, and the non-resonant two-photon absorption recording material wherein the main chain of the non-resonant polymer two-photon absorption compound contains at least one member selected from polystyrene, polyacrylate, polymethacrylate-polyester, polyurethane, polyether and polyimide, and also provides an optical information recording medium having a recording layer containing the recording material.

25 Claims, 2 Drawing Sheets

(51) Int. Cl.
    *C07C 69/76*    (2006.01)
    *G02B 1/04*    (2006.01)
    *B82Y 10/00*    (2011.01)
    G11B 7/0045    (2006.01)
    G11B 7/24044    (2013.01)
    G11B 7/2405    (2013.01)

(56) References Cited

U.S. PATENT DOCUMENTS

| | | | |
|---|---|---|---|
| 2006/0257615 A1 | 11/2006 | Takano et al. | |
| 2007/0077480 A1* | 4/2007 | Curello et al. | 429/34 |
| 2007/0242323 A1* | 10/2007 | Yamada | 359/3 |
| 2008/0130444 A1* | 6/2008 | Kikukawa et al. | 369/53.15 |
| 2009/0303855 A1 | 12/2009 | Akiba et al. | |
| 2010/0078607 A1 | 4/2010 | Akiba et al. | |
| 2010/0182895 A1 | 7/2010 | Oyamada et al. | |
| 2010/0309759 A1* | 12/2010 | Sato et al. | 369/44.26 |

FOREIGN PATENT DOCUMENTS

| | | | |
|---|---|---|---|
| JP | 2004-346238 | * | 12/2004 |
| JP | 2005-29725 A | | 2/2005 |
| JP | 2005-97538 A | | 4/2005 |
| JP | 2005-258388 A | | 9/2005 |
| JP | 2005-320502 A | | 11/2005 |
| JP | 2006-318516 A | | 11/2006 |
| JP | 2007-87532 A | | 4/2007 |
| JP | 2007-262155 A | | 10/2007 |
| JP | 2008-226324 A | | 9/2008 |
| JP | 2009-099253 | * | 5/2009 |
| JP | 2009-104717 A | | 5/2009 |
| JP | 2010-108588 A | | 5/2010 |
| JP | 2010-162846 A | | 7/2010 |
| WO | 01/96452 A2 | | 12/2001 |

OTHER PUBLICATIONS

Carlini "Polymeric photoinitiators containing side chain ketoaromatic moieties for fast ultraviolet initiated polymerization of acrylic monomers", Br. Poly. J. vol. 18(4) pp. 236-241 (1986).*
International Search Report dated Aug. 21, 2012 issued in International Application No. PCT/JP2012/062128 (PCT/ISA/210).
Written Opinion (PCT/ISA/237), dated Aug. 21, 2012, issued by the International Searching Authority in counterpart International Patent Application No. PCT/JP2012/062128.
Office Action dated Sep. 24, 2014, issued by the Japanese Patent Office in counterpart Japanese Application No. 2012-108951.

* cited by examiner

NON-RESONANT TWO-PHOTON ABSORPTION RECORDING MATERIAL, NON-RESONANT POLYMER TWO-PHOTON ABSORPTION OPTICAL INFORMATION RECORDING MEDIUM, AND RECORDING/REPRODUCING METHOD

CROSS REFERENCE TO RELATED APPLICATION

This is a continuation of International Application No. PCT/JP2012/062128 filed on May 11, 2012, and claims priority from Japanese Patent Application No. 2011-108698, filed on May 13, 2011, and Japanese Patent Application No. 2011-154893, filed on Jul. 13, 2011, and Japanese Patent Application No. 2012-108951, filed on May 10, 2012, the entire disclosures of which are incorporated therein by reference.

TECHNICAL FIELD

The present invention relates to a non-resonant two-photon absorption recording material and a non-resonant two-photon absorption compound. More specifically, the present invention provides a recording material having high humidity/heat resistance for performing three-dimensional recording of recording pits in the inside of a recording medium by using non-resonant two-photon absorption, which ensures that the recording pits recorded can be read out and non-resonant two-photon absorption recording can be performed using recording light in the wavelength region shorter than 700 nm, and a two-photon absorption compound.

BACKGROUND ART

In general, the non-linear optical effect indicates a non-linear optical response proportional to the square, cube or higher power of a photoelectric field applied. Known examples of the second-order non-linear optical effect proportional to the square of a photoelectric field applied include second harmonic generation (SHG), optical rectification, photorefractive effect, Pockels effect, parametric amplification, parametric oscillation, light sum frequency mixing, and light difference frequency mixing. Also, examples of the third-order non-linear optical effect proportional to the cube of photoelectric filed applied include third harmonic generation (THG), optical Kerr effect, self-induced refractive index change, and two-photon absorption.

As for the non-linear optical material exhibiting these non-linear optical effects, a large number of inorganic materials have been heretofore found. However, an inorganic material can be very hardly used in practice because a so-called molecular design so as to optimize the desired non-linear optical characteristics or various properties necessary for the production of a device is difficult. On the other hand, an organic compound can realize not only optimization of the desired non-linear optical characteristics by the molecular design but also control of other various properties and therefore, the probability of its practical use is high. Thus, an organic compound is attracting attention as a promising non-linear optical material.

In recent years, among non-linear optical characteristics of the organic compound, third-order non-linear optical effects, particularly, non-resonant two-photon absorption, are being taken notice of. The two-photon absorption is a phenomenon of a compound being excited by simultaneously absorbing two photons. In the case where the two-photon absorption occurs in the energy region having no (linear) absorption band of the compound, this is called non-resonant two-photon absorption. In the following, even when not particularly specified, "two-photon absorption" indicates "non-resonant two-photon absorption". Also, "simultaneous two-photon absorption" is sometimes simply referred to as "two-photon absorption" by omitting "simultaneous".

Meanwhile, the non-resonant two-photon absorption efficiency is proportional to the square of a photoelectric field applied (quadratic dependency of two-photon absorption). Therefore, when a two-dimensional plane is irradiated with a laser, two-photon absorption takes place only in the position having a high electric field strength in the central part of the laser spot, and absolutely no two-photon absorption occurs in the portion having a weak electric field strength in the periphery. On the other hand, in a three-dimensional space, two-photon absorption occurs only in the region having a large electric field strength at the focus where the laser rays are converged through a lens, and two-photon absorption does not take place at all in the off-focus region because the electric field strength is weak. Compared with linear absorption where excitation occurs in all positions proportionally to the strength of a photoelectric field applied, in the non-resonant two-photon absorption, excitation occurs only at one point inside the space because of the quadratic dependency and therefore, the spatial resolution is remarkably enhanced.

Usually, in the case of inducing non-resonant two-photon absorption, a short pulsed laser in the near infrared region having a wavelength longer than the wavelength region where the (linear) absorption band of a compound is present, and having no absorption is used in many cases. Thanks to use of near infrared light in a so-called transparent region, the excitation light can reach the inside of a sample without being absorbed or scattered and one point inside the sample can be excited with very high spatial resolution because of the quadratic dependency of non-resonant two-photon absorption.

The present applicant have filed various patent applications relating to a two-photon sensitization-type three-dimensional recording material using a compound capable of inducing non-resonant two-photon absorption. This recording material is a recording material containing at least (1) a two-photon absorption compound (two-photon sensitizer) and (2) a refractive index-modulating material or a fluorescence intensity-modulating material, where (1) efficiently undergoes two-photon absorption and the obtained energy is transferred to (2) by photoexcited electron transfer or energy transfer to change the refractive index or fluorescence intensity of (2), thereby performing the recording. Thanks to use of non-resonant two-photon absorption but not one-photon absorption employed in the process of light absorption of normal optical recording, a recording pit with three-dimensional spatial resolution can be written at an arbitrary position inside of a recording material.

For example, Patent Document 1 discloses a technique using, as (2) a refractive index- or fluorescence intensity-modulating material, a material capable of modulating the refractive index by the color formation of a dye, or a material capable of modulating the fluorescence from non-fluorescence to fluorescence or from fluorescence to non-fluorescence (a material capable of modulating a refractive index or fluorescence by the color formation of a dye or a fluorescent dye). Also, Patent Document 2 discloses a technique using, as (2) a refractive index- or fluorescence intensity-modulating material, a material capable of forming a seed (latent image speck) through very slight color formation of a dye or change of fluorescence and then performing recording and amplification under light irradiation or heating (a refractive index/ fluorescence modulation and latent image amplification system; a material that forms a latent image capable of performing refractive index/fluorescence modulation by color formation of a dye). In addition, for example, Patent Document 3 discloses a technique using, as (2) a refractive index-modulating material, a material capable of forming a macromolecular polymer by polymerization and thereby modulating the refractive index (a material that performs refractive index modulation by polymerization). Furthermore, Patent Document 4 discloses a technique using, as a refractive index-modulating material, a material capable of forming a very fine polymerized latent image speck and then driving the polymerization (a refractive index modulation and latent image polymerization system; a material that forms a latent image capable of performing refractive index modulation by polymerization).

In all of these two-photon sensitization-type three-dimensional recording materials described in Patent Documents 1 to 4, a material capable of performing two-photon absorption with light of 700 nm or more is used as (1) the two-photon absorption compound (two-photon sensitizer). However, there are various demands in recent years, and above all, for obtaining a higher recording density, a recording material capable of performing non-resonant two-photon absorption recording by using recording light in the wavelength region shorter than 700 nm so as to form a smaller pit in the recording material is required. The two-photon absorption compound described in Patent Document 5 can perform non-resonant two-photon absorption recording.

Incidentally, in Non-Patent Document 1, it is disclosed that a compound having a structure shown below exhibits non-resonant two-photon absorption properties for light at 450 to 600 nm.

[Chem. 1]

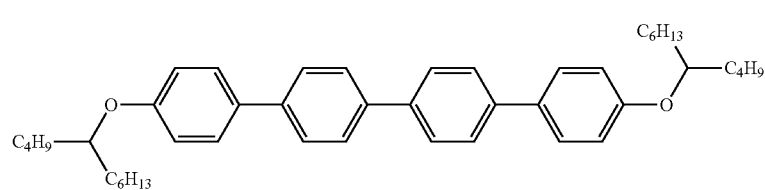

However, there is no description of the humidity/heat resistance of the non-resonant two-photon absorption recording material using a two-photon absorption compound capable of performing non-resonant two-photon absorption recording by using recording light in the wavelength region shorter than 700 nm described in Patent Document above.

PRIOR-ART DOCUMENTS

Patent Document

Patent Document 1: JP-A-2007-87532 (the term "JP-A" as used herein means an "unexamined published Japanese patent application")
Patent Document 2: JP-A-2005-320502
Patent Document 3: JP-A-2005-29725
Patent Document 4: JP-A-2005-97538
Patent Document 5: JP-A-2010-108588

Non-Patent Document

Non-Patent Document 1: Y. Morel, 0. Stephan, C. Andraud, and P. L. Baldeck, *Synth. Met.*, 2001, 124, 237

SUMMARY OF THE INVENTION

Problems that the Invention is to Solve

An object of the present invention is to provide a non-resonant two-photon absorption recording material in which the non-resonant two-photon absorption recording material has high humidity/heat resistance and sufficient recording/readout characteristics, and a non-resonant polymer two-photon absorption compound usable therein.

Means for Solving the Problems

As a result of intensive studies, the present inventors have found that the above-described object can be attained by the following configurations.

1. A non-resonant two-photon absorption recording material containing a non-resonant polymer two-photon absorption compound.

2. The non-resonant two-photon absorption recording material as described in 1 above, wherein the main chain of the non-resonant polymer two-photon absorption compound contains at least one member selected from polystyrene, polyacrylate, polymethacrylate, polyester, polyurethane, polyether and polyimide.

3. The non-resonant two-photon absorption recording material as described in 1 or 2 above, wherein the non-resonant polymer two-photon absorption compound is a compound containing a structure represented by the following formula (1):

[Chem. 2]

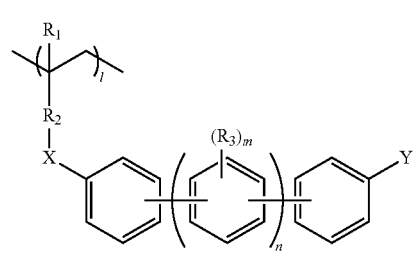

Formula (1)

(wherein Y represents a substituent having a Hammett sigma para value (σp value) of 0 or more; X represents a divalent substituent having a Hammett sigma para value (σp value) of 0 or more; X and Y may be the same as or different from each other; n represents an integer of 1 to 4; $R_1$ represents a hydrogen atom or a substituent; $R_2$ represents a divalent substituent; $R_3$ represents a substituent; when a plurality of $R_1$, $R_2$ or $R_3$ are present, $R_1$, $R_2$ or $R_3$ may be the same as or different from every other $R_1$, $R_2$ or $R_3$; l represents an integer of 1 or more; and m represents an integer of 0 to 4).

4. The non-resonant two-photon absorption recording material as described in any one of 1 to 3 above, wherein the non-resonant polymer two-photon absorption compound is a compound containing a structure represented by the following formula (2):

[Chem. 3]

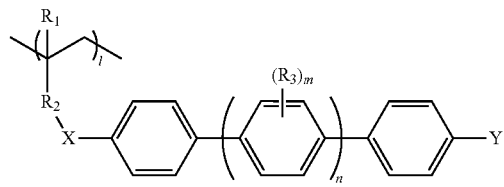

Formula (2)

(wherein Y represents a substituent having a Hammett sigma para value (σp value) of 0 or more; X represents a divalent substituent having a Hammett sigma para value (σp value) of 0 or more; X and Y may be the same as or different from each other; n represents an integer of 1 to 4; $R_1$ represents a hydrogen atom or a substituent; $R_2$ represents a divalent substituent; $R_3$ represents a substituent; when a plurality of $R_1$, $R_2$ or $R_3$ are present, $R_1$, $R_2$ or $R_3$ may be the same as or different from every other $R_1$, $R_2$ or $R_3$; l represents an integer of 1 or more; and m represents an integer of 0 to 4).

5. The non-resonant two-photon absorption recording material as described in any one of 1 to 4 above, wherein the non-resonant polymer two-photon absorption compound represented by formula (1) or (2) is a compound containing a structure represented by the following formula (3):

[Chem. 4]

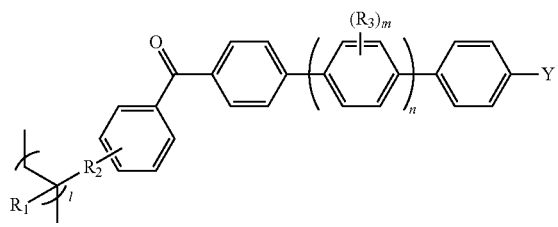

Formula (3)

(wherein Y represents a substituent having a Hammett sigma para value (σp value) of 0 or more; n represents an integer of 1 to 4; $R_1$ represents a hydrogen atom or a substituent; $R_2$ represents a divalent substituent; $R_3$ represents a substituent; when a plurality of $R_1$, $R_2$ or $R_3$ are present, $R_1$, $R_2$ or $R_3$ may be the same as or different from every other $R_1$, $R_2$ or $R_3$; l represents an integer of 1 or more; and m represents an integer of 0 to 4).

6. The non-resonant two-photon absorption recording material as described in any one of 1 to 5 above, wherein the non-resonant polymer two-photon absorption compound represented by formula (1), (2) or (3) is a compound containing a structure represented by the following formula (4):

[Chem. 5]

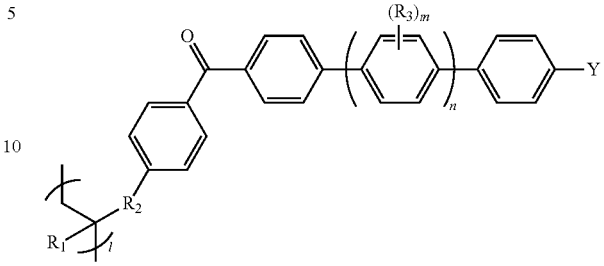

Formula (4)

(wherein Y represents a substituent having a Hammett sigma para value (σp value) of 0 or more; n represents an integer of 1 to 4; $R_1$ represents a hydrogen atom or a substituent; $R_2$ represents a divalent substituent; $R_3$ represents a substituent; when a plurality of $R_1$, $R_2$ or $R_3$ are present, $R_1$, $R_2$ or $R_3$ may be the same as or different from every other $R_1$, $R_2$ or $R_3$; l represents an integer of 1 or more; and m represents an integer of 0 to 4).

7. The non-resonant two-photon absorption recording material as described in any one of 1 to 6 above, wherein the non-resonant two-photon absorption recording material contains a polymer compound containing, as a copolymer component, a non-resonant polymer two-photon absorption compound represented by at least one of formulae (1) to (4).

8. The non-resonant two-photon absorption recording material as described in any one of 1 to 7 above, wherein the non-resonant two-photon absorption recording material forming a recording layer contains at least (a) the non-resonant polymer two-photon absorption compound described in any one of 1 to 7 above and (b) a material capable of changing the reflected light intensity between before and after two-photon recording.

9. The non-resonant two-photon absorption recording material as described in any one of 1 to 7 above, wherein the non-resonant two-photon absorption recording material forming a recording layer contains at least (a) the non-resonant polymer two-photon absorption compound described in 1 to 7 above and (b) a material capable of changing the refractive index between before and after two-photon recording.

10. The non-resonant two-photon absorption recording material as described in any one of 1 to 7 above, wherein the non-resonant two-photon absorption recording material forming a recording layer contains the non-resonant polymer two-photon absorption compound described in 1 to 7 above and the non-resonant polymer two-photon absorption compound described in any one of 1 to 7 above can change the reflected light intensity between before and after two-photon recording.

11. The non-resonant two-photon absorption recording material as described in any one of 1 to 7 above, wherein the non-resonant two-photon absorption recording material forming a recording layer contains the non-resonant polymer two-photon absorption compound described in 1 to 7 above and the non-resonant polymer two-photon absorption compound described in any one of 1 to 7 above can change the refractive index between before and after two-photon recording.

12. An optical information recording medium having a recording layer containing the recording material described in any one of 1 to 7 above.

13. The optical information recording medium as described in 12 above,
wherein the thickness of the recording layer is from 50 nm to 5 μm.

14. The optical information recording medium as described in 12 above,
wherein the optical recording medium has an intermediate layer located adjacent to the recording layer so as to physically separate the recording layer and form an interface capable of forming a recording mark by expansion.

15. The optical information recording medium as described in 14 above,
wherein the refractive index difference between the recording layer and the intermediate layer is from 0.01 to 0.5.

16. The optical information recording medium as described in 14 above,
wherein the thickness of the intermediate layer is from 2 μm to 20 μm.

17. The optical information recording medium as described in 12 above,
wherein the optical information recording medium has a substrate.

18. The optical information recording medium as described in 17 above,
wherein the substrate thickness is from 0.02 mm to 2 mm.

19. The optical information recording medium as described in 12 above,
wherein the optical information recording medium has a guide layer for performing the radial position control by a tracking servo during recording.

20. The optical information recording medium as described in 12 above,
wherein the optical information recording medium has a cover layer on the light incidence-side surface side relative to the recording layer.

21. The optical information recording medium as described in 20 above,
wherein the thickness of the cover layer is from 0.01 mm to 0.2 mm.

22. The optical information recording medium as described in 12 above,
wherein the optical information recording medium has a reflecting layer.

23. The optical information recording medium as described in 12 above,
wherein the optical information recording medium has a spacer layer.

24. The optical information recording medium as described in 23 above,
wherein the thickness of the spacer layer is from 5 μm to 100 μm.

25. The optical information recording medium as described in 12 above,
wherein the optical information recording medium performs marking.

26. The optical information recording medium as described in 12 above,
wherein the optical information recording medium has a hardcoat layer on the light incidence-side surface.

27. The optical information recording medium as described in 12 above,
wherein the optical information recording medium is housed in a cartridge.

28. The optical information recording medium as described in any one of 13 to 27 above.

29. A recording/reproducing method on the optical information recording medium described in 28 above,
wherein the peak power of a recording laser is from 1 to 100 W on the surface of the optical information recording medium, the average power of the recording laser is 100 mW or less on the surface of the optical information recording medium, and the product of the pulse width and the oscillation cycle of the recording laser is from 0.001 to 0.1.

30. A recording/reproducing method on the optical information recording medium described in 28, comprising using a confocal optical system at the time of reproducing the information.

31. A compound represented by the following formula (5):

[Chem. 6]

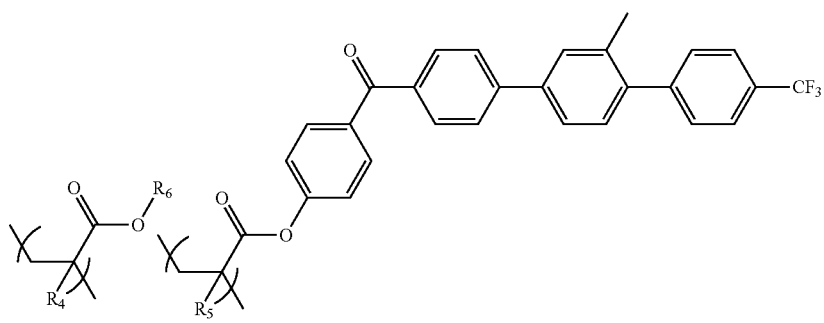

Formula (5)

(wherein each of $R_4$, $R_5$ and $R_6$ represents a hydrogen atom or a substituent, and $R_4$, $R_5$ and $R_6$ may be the same as or different from each other).

32. A compound represented by the following formula (6):

[Chem. 7]

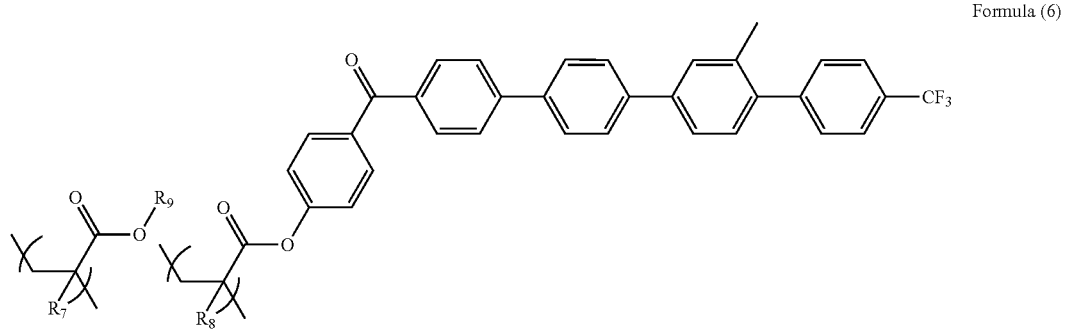

Formula (6)

(wherein each of $R_7$, $R_8$ and $R_9$ represents a hydrogen atom or a substituent, and $R_7$, $R_8$ and $R_9$ may be the same as or different from each other).

Advantage of the Invention

According to the configuration of the two-photon absorption recording material of the present invention, non-resonant two-photon absorption recording can be performed and at the same time, the humidity/heat resistance after the recording is high.

MODE FOR CARRYING OUT THE INVENTION

Figure 1:
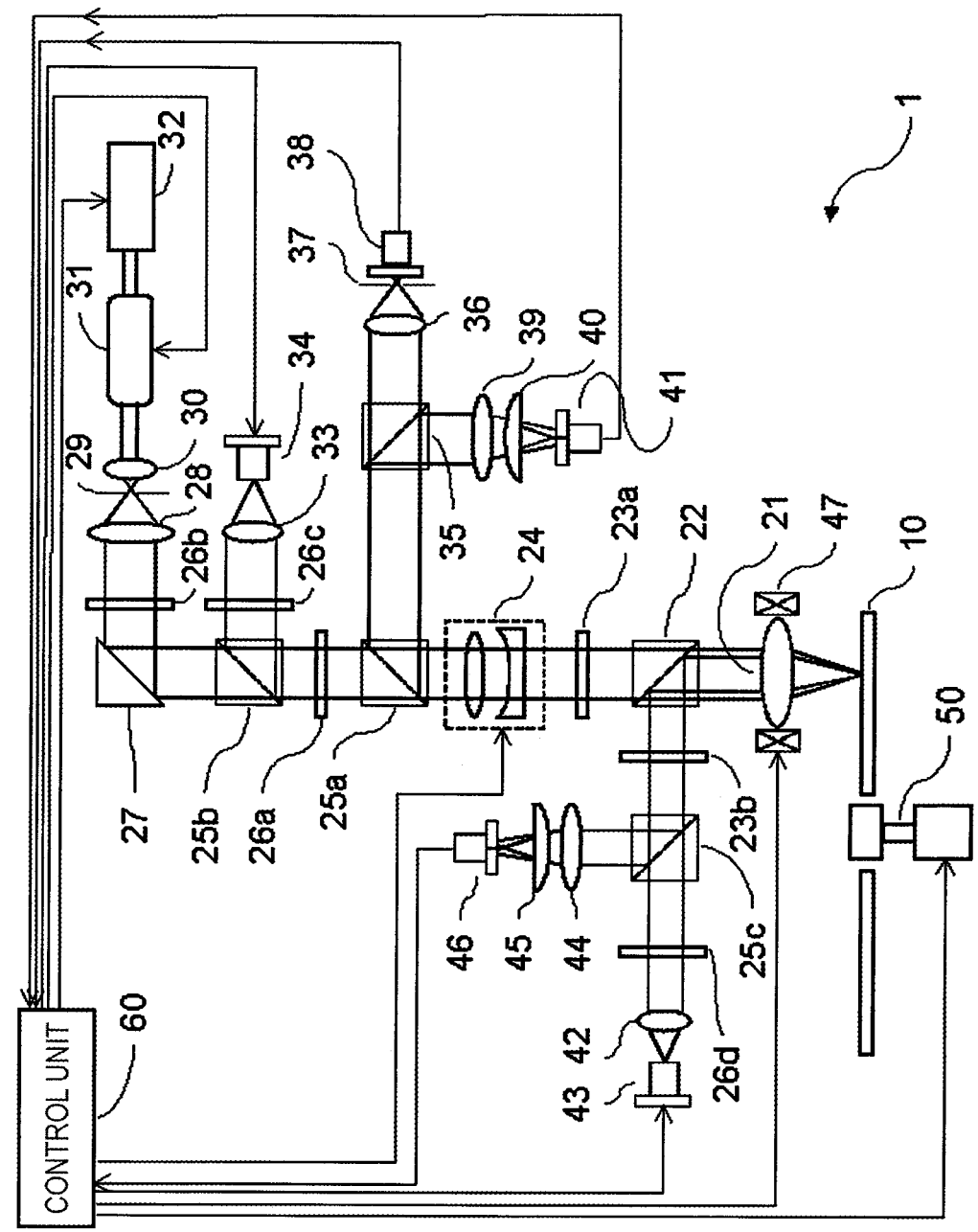
FIG. 1 is a view showing the outline of one example of the recording/reproducing apparatus used for recording/reproduction of the two-photon absorption recording material of the present invention.

The two-photon absorption recording material of the present invention is described in detail below.

Non-Resonant Polymer Two-Photon Absorption Compound

The (a) non-resonant polymer two-photon absorption compound used in the non-resonant two-photon absorption recording material of the present invention is described below.

The main chain of the non-resonant polymer two-photon absorption compound is not particularly limited, but specific examples thereof include polystyrene, polyacrylate, polymethacrylate, polyester, polyurethane, polyether, and polyimide. Among these, polystyrene, polyacrylate, polymethacrylate and polyurethane are preferred, and polyacrylate and polymethacrylate are most preferred.

The weight average molecular weight of the non-resonant polymer two-photon absorption compound is preferably from 1,000 to 1,000,000, more preferably from 10,000 to 700,000, and most preferably from 30,000 to 500,000.

The molecular weight distribution (weight average molecular weight±number average molecular weight, Mw/Mn) of the non-resonant polymer two-photon absorption compound is not particularly limited but is preferably 5.0 or less, more preferably 3.0 or less, and most preferably 2.0 or less.

The non-resonant polymer two-photon absorption compound is preferably a polymer compound containing, as copolymer components, a non-resonant polymer two-photon absorption compound represented by at least any one of the later-described formulae (1) to (4) and a monomer other than the non-resonant polymer two-photon absorption compound.

In the case of a copolymer, the compositional ratio of the non-resonant polymer two-photon absorption compound is not particularly limited, but the percentage of the two-photon absorption compound is preferably from 1 to 80 mol %, more preferably from 3 to 50 mol %, and most preferably from 8 to 30 mol %.

The number of copolymerization components of the non-resonant polymer two-photon absorption compound is not particularly limited but is preferably 10 or less, more preferably 5 or less, and most preferably 3 or less.

The configuration of the copolymer of the non-resonant polymer two-photon absorption compound may be any of a block copolymer, a random copolymer and a graft copolymer.

In a polymerization reaction for synthesizing the non-resonant polymer two-photon absorption compound of the present invention, the reaction type thereof is preferably any one of radical polymerization, cationic polymerization, anionic polymerization and polycondensation, more preferably radical polymerization or cationic polymerization, and most preferably radical polymerization.

At this time, as for the polymerizable group contained in a dye having a polymerizable group or in a polymerizable compound having no dye moiety, when the polymerization is radical polymerization, the polymerizable group is an ethylenic unsaturated group moiety such as acryloyl group, methacryloyl group, styryl group and vinyl group, preferably an acryloyl group or a methacryloyl group, and when the polymerization is cationic polymerization or anionic polymerization, the polymerizable group is any one of an oxirane ring, an oxetane ring, a vinyl ether group and an N-vinylcarbazole moiety, preferably an oxirane ring or an oxetane ring.

The solvent used when synthesizing the non-resonant polymer two-photon absorption compound of the present invention includes, for example, ethylene dichloride, cyclohexanone, methyl ethyl ketone, acetone, methanol, ethanol, propanol, butanol, ethylene glycol monomethyl ether, ethylene glycol monoethyl ether, 2-methoxyethyl acetate, 1-methoxy-2-propanol, 1-methoxy-2-propyl acetate, N,N-dimethylformamide, N,N-dimethylacetamide, dimethylsulfoxide, toluene, tetrahydrofuran, ethyl acetate, methyl lactate, and ethyl lactate.

One of these solvents may be used alone, or two or more thereof may be mixed.

The monomer that can be used as a copolymerization component of the non-resonant polymer two-photon absorption compound is not particularly limited but specifically includes the following compounds:

acrylic acid esters and methacrylic acid esters each having an aliphatic hydroxyl group, such as 2-hydroxyethyl acrylate, 2-hydroxypropyl acrylate, 3-hydroxypropyl acrylate, 4-hydroxybutyl acrylate, 2-hydroxyethyl methacrylate, 2-hydroxypropyl methacrylate, 3-hydroxypropyl methacrylate and 4-hydroxybutyl methacrylate;

an alkyl acrylate such as methyl acrylate, ethyl acrylate, propyl acrylate, butyl acrylate, isobutyl acrylate, amyl acrylate, hexyl acrylate, 2-ethylhexyl acrylate, octyl acrylate, benzyl acrylate, 2-chloroethyl acrylate, glycidyl acrylate, 3,4-epoxycyclohexylmethyl acrylate, vinyl acrylate, 2-phenylvinyl acrylate, 1-propenyl acrylate, allyl acrylate, 2-allyloxyethyl acrylate and propargyl acrylate;

an alkyl methacrylate such as methyl methacrylate, ethyl methacrylate, propyl methacrylate, isopropyl methacrylate, butyl methacrylate, isobutyl methacrylate, n-butyl methacrylate, sec-butyl methacrylate, tert-butyl methacrylate, amyl methacrylate, hexyl methacrylate, 2-ethylhexyl methacrylate, cyclohexyl methacrylate, benzyl methacrylate, 2-chloroethyl methacrylate, glycidyl methacrylate, 3,4-epoxycyclohexylmethyl methacrylate, vinyl methacrylate, 2-phenylvinyl methacrylate, 1-propenyl methacrylate, allyl methacrylate, 2-allyloxyethyl methacrylate and propargyl methacrylate;

an acrylamide or methacrylamide such as acrylamide, methacrylamide, N-methylolacrylamide, N-ethylacrylamide, N-hexylmethacrylamide, N-cyclohexylacrylamide, N-hydroxyethylacrylamide, N-phenylacrylamide, N-nitrophenylacrylamide, N-ethyl-N-phenylacrylamide, vinylacrylamide, vinylmethacrylamide, N,N-diallylacrylamide, N,N-diallylmethacrylatmide, allylacrylamide and allylmethacrylamide;

vinyl ethers such as ethyl vinyl ether, 2-chloroethyl vinyl ether, hydroxyethyl vinyl ether, propyl vinyl ether, butyl vinyl ether, octyl vinyl ether and phenyl vinyl ether;

vinyl esters such as vinyl acetate, vinyl chloroacetate, vinyl butyrate and vinyl benzoate;

styrenes such as styrene, α-methylstyrene, methylstyrene, chloromethylstyrene and p-acetoxystyrene;

vinyl ketones such as methyl vinyl ketone, ethyl vinyl ketone, propyl vinyl ketone and phenyl vinyl ketone;

olefins such as ethylene, propylene, isobutylene, butadiene and isoprene;

N-vinylpyrrolidone, acrylonitrile, methacrylonitrile and the like;

an unsaturated imide such as maleimide, N-acryloylacrylamide, N-acetylmethacryl amide, N-propionylmethacrylamide and N-(p-chlorobenzoyl)methacrylamide; and a methacrylic acid-based monomer in which a heteroatom is bonded on the α-position, such as compounds described in JP-A-2002-309057 and JP-A-2002-311569.

Other examples include a non-halogen-based aliphatic compound. Specifically, examples of the monofunctional type include an unsaturated acid compound such as (meth) acrylic acid, itaconic acid and maleic acid; an alkoxyalkylene glycol(meth)acrylate type such as methoxydiethy(propy)lene glycol(meth)acrylate, methoxytriethy(propy)lene glycol (meth)acrylate, methoxytetraethy(propy)lene glycol(meth) acrylate, methoxypolyethy(propy)lene glycol(meth)acrylate, ethoxydiethy(propy)lene glycol(meth)acrylate, ethoxytriethy(propy)lene glycol(meth)acrylate and ethoxypolyethy (propy)lene glycol(meth)acrylate; an alicyclic(meth)acrylate type such as cyclohexyl(meth)acrylate, tetrahydrofuryl (meth)acrylate, isobornyl(meth)acrylate, dicyclopentanyl (meth)acrylate, tricyclopentanyl(meth)acrylate, dicyclopentadienyl(meth)acrylate and pinanyl(meth)acrylate; an amine-type (meth)acrylate such as N,N-dimethylaminoethyl(meth) acrylate, N,N-diethylaminoethyl(meth)acrylate, (meth)acryl amide and diacetone (meth)acrylamide; and a functional group-containing (meth)acrylate such as allyl(meth)acrylate and glycidyl(meth)acrylate.

Next, examples of the polyfunctional type include an alkyl-type (meth)acrylate such as 1,3-propanediol di(meth)acrylate, 1,4-butanediol di(meth)acrylate, 1,6-hexanediol di(meth)acrylate, neopentyl glycol di(meth)acrylate, bis (acryloxyneopentyl glycol) adipate, bis(methacryloxyneopentyl glycol) adipate, epichlorohydrin-modified 1,6-hexanediol di(meth)acrylate (Kayarad R-167 produced by Nippon Kayaku Co., Ltd.), hydroxypivalic acid neopentyl glycol di(meth)acrylate and caprolactone-modified hydroxypivalic acid neopentyl glycol di(meth)acrylate (Kayarad HX series produced by Nippon Kayaku Co., Ltd.); an alkylene glycol-type (meth)acrylate such as ethylene glycol di(meth) acrylate, diethylene glycol di(meth)acrylate, triethylene glycol di(meth)acrylate, tetraethylene glycol di(meth)acrylate, polyethylene glycol di(meth)acrylate, epichlorohydrin-modified ethylene glycol di(meth)acrylate (Denacol DA(M)-811 produced by Nagase & Co., Ltd.), epichlorohydrin-modified ethylene glycol di(meth)acrylate (Denacol DA(M)-851 produced by Nagase & Co., Ltd.), propylene glycol di(meth) acrylate, dipropylene glycol di(meth)acrylate, tripropylene glycol di(meth)acrylate, tetrapropylene glycol di(meth)acrylate, polypropylene glycol di(meth)acrylate and epichlorohydrin-modified propylene glycol di(meth)acrylate (DA(M)-911 produced by Nagase & Co., Ltd.); a trimethylolpropane-type (meth)acrylate such as trimethylolpropane tri(meth) acrylate, ditrimethylolpropane tri(meth)acrylate, neopentyl glycol-modified trimethylolpropane di(meth)acrylate (Kayarad R-604 produced by Nippon Kayaku Co., Ltd.), ethylene oxide-modified trimethylolpropane tri(meth)acrylate (Sartomer SR-454), propylene oxide-modified trimethylolpropane tri(meth)acrylate (TPA-310 produced by Nippon Kayaku Co., Ltd.) and epichlorohydrin-modified trimethylolpropane tri(meth)acrylate (DA(M)-321 produced by Nagase & Co., Ltd.); a pentaerythritol-type (meth)acrylate such as pentaerythritol tri(meth)acrylate, pentaerythritol tetra(meth) acrylate, stearic acid-modified pentaerythritol di(meth)acrylate (Aronix M-233 produced by Toagosei Chemical Industry Co., Ltd.), dipentaerythritol hexa(meth)acrylate, dipentaerythritol monohydroxypenta(meth)acrylate, alkyl-modified dipentaerythritol poly(meth)acrylates (e.g., Kayarad D-310, 320 and 330 produced by Nippon Kayaku Co., Ltd.) and caprolactone-modified dipentaerythritol poly(meth) acrylates (e.g., Kayarad DPCA-20, 30, 60 and 120 produced by Nippon Kayaku Co., Ltd.); a glycerol-type (meth)acrylate such as glycerol di(meth)acrylate, epichlorohydrin-modified glycerol tri(meth)acrylate (Denacol DA(M)-314 produced by Nagase & Co., Ltd.) and triglycerol di(meth)acrylate; an alicyclic (meth)acrylate such as dicyclopentanyl di(meth)acrylate, tricyclopentanyl di(meth)acrylate, cyclohexyl di(meth) acrylate and methoxylated cyclohexyl di(meth)acrylate (CAM-200 produced by Sanyo Kokusaku Pulp Co., Ltd.); and an isocyanurate-type (meth)acrylate such as tris(acryloxyethyl) isocyanurate (Aronix M-315 produced Toagosei Chemical Industry Co., Ltd.), tris(methacryloxyethyl) isocyanurate, caprolactone-modified tris(acryloxyethyl) isocyanurate and caprolactone-modified tris(methacryloxyethyl) isocyanurate.

Out of the compounds composed of only an aliphatic group and having a polymerizable ethylenically unsaturated group, for example, a compound further containing a sulfur atom in the molecule is described below. Examples of the monofunctional type include an alkoxyalkylene glycol thio(meth)acrylate type such as methoxydiethy(propy)lene glycol thio(meth)acrylate, methoxytriethy(propy)lene glycol thio(meth)acrylate, methoxytetraethy(propy)lene glycol thio(meth)acrylate, methoxypolyethy(propy)lene glycol thio(meth)acrylate, ethoxydiethy(propy)lene glycol thio(meth)acrylate, ethoxytriethy(propy)lene glycol thio(meth)acrylate and ethoxypolyethy(propy)lene glycol thio(meth)acrylate; and an alicyclic thio(meth)acrylate type such as cyclohexyl thio(meth)acrylate, tetrahydrofuryl thio(meth)acrylate, isobornyl thio(meth)acrylate, dicyclopentanyl thio(meth)acrylate, tricyclopentanyl thio(meth)acrylate, dicyclopentadienyl thio(meth)acrylate and pinanyl thio(meth)acrylate.

Examples of the polyfunctional type include an alkyl-type thio(meth)acrylate such as 1,3-propanediol dithio(meth)acrylate, 1,4-butanediol dithio(meth)acrylate, 1,6-hexanediol dithio(meth)acrylate, neopentyl glycol dithio(meth)acrylate, bis(thioacryloxyneopentyl glycol) adipate, bis(thiomethacryloxyneopentyl glycol) adipate, epichlorohydrin-modified 1,6-hexanediol dithio(meth)acrylate, hydroxypivalic acid neopentyl glycol dithio(meth)acrylate and caprolactone-modified hydroxypivalic acid neopentyl glycol dithio(meth)acrylate; an alkylene glycol-type thio(meth)acrylate such as ethylene glycol dithio(meth)acrylate, diethylene glycol dithio(meth)acrylate, triethylene glycol dithio(meth)acrylate, tetraethylene glycol dithio(meth)acrylate, polyethylene glycol dithio(meth)acrylate, epichlorohydrin-modified ethylene glycol dithio(meth)acrylate, epichlorohydrin-modified diethylene glycol dithio(meth)acrylate, propylene glycol dithio(meth)acrylate, dipropylene glycol dithio(meth)acrylate, tripropylene glycol dithio(meth)acrylate, tetrapropylene glycol dithio(meth)acrylate, polypropylene glycol dithio(meth)acrylate and epichlorohydrin-modified propylene glycol dithio(meth)acrylate; a trimethylolpropane-type thio(meth)acrylate such as trimethylolpropane trithio(meth)acrylate, ditrimethylolpropane trithio(meth)acrylate, neopentyl glycol-modified trimethylolpropane dithio(meth)acrylate, ethylene oxide-modified trimethylolpropane trithio(meth)acrylate, propylene oxide-modified trimethylolpropane trithio(meth)acrylate and epichlorohydrin-modified trimethylolpropane trithio(meth)acrylate; a pentaerythritol-type thio(meth)acrylate such as pentaerythritol trithio(meth)acrylate, pentaerythritol tetrathio(meth)acrylate, stearic acid-modified pentaerythritol dithio(meth)acrylate, dipentaerythritol hexathio(meth)acrylate, dipentaerythritol monohydroxypentathio(meth)acrylate, alkyl-modified dipentaerythritol polythio(meth)acrylate and caprolactone-modified dipentaerythritol polythio(meth)acrylates; a glycerol-type thio(meth)acrylate such as glycerol dithio(meth)acrylate, epichlorohydrin-modified glycerol trithio(meth)acrylate and triglycerol dithio(meth)acrylate; an alicyclic thio(meth)acrylate such as dicyclopentanyl dithio(meth)acrylate, tricyclopentanyl dithio(meth)acrylate, cyclohexyl dithio(meth)acrylate, methoxylated cyclohexyl dithio(meth)acrylate; and an isocyanurate-type thio(meth)acrylate such as tris(thioacryloxyethyl) isocyanurate, tris(thiomethacryloxyethyl) isocyanurate, caprolactone-modified tris(thioacryloxyethyl) isocyanurate and caprolactone-modified tris(thiomethacryloxyethyl) isocyanurate. One of these compounds may be used alone, or a plurality thereof may be mixed and used.

Out of the compounds having an ethylenically unsaturated group, examples of the compound having an aromatic ring or(and) a halogen atom in the molecule include styrenes such as styrene, α-methylstyrene and 4-methoxy(or ethoxy)styrene; a di- or poly(meth)acrylate compound such as phenyl (meth)acrylate, 4-phenylethyl(meth)acrylate, 4-methoxycarbonylphenyl(meth)acrylate, 4-ethoxycarbonylphenyl(meth)acrylate, 4-butoxycarbonylphenyl(meth)acrylate, 4-tert-butylphenyl(meth)acrylate, benzyl EO-modified phenoxylated phosphoric acid (meth)acrylate, EO-modified phthalic acid (meth)acrylate, 4-biphenylyl(meth)acrylate and aromatic polyhydroxy compound (e.g., hydroquinone, resorcin, catechol, pyrogallol); an aromatic group-containing (meth)acrylate compound such as bisphenol A di(meth)acrylate, ethy(propy)lene oxide-modified bisphenol A di(meth)acrylate, bisphenol F di(meth)acrylate, ethy(propy)lene oxide-modified bisphenol F di(meth)acrylate, bisphenol S di(meth)acrylate, ethy(propy)lene oxide-modified bisphenol S di(meth)acrylate and epichlorohydrin-modified phthalic acid di(meth)acrylate; styrenes and a (meth)acrylate compound, each having an aromatic group substituted with a halogen atom having an atomic weight of chlorine or more, such as p-chlorostyrene, p-bromostyrene, p-chlorophenoxyethyl(meth)acrylate, p-bromophenoxyethyl(meth)acrylate, trichlorophenolethy(propy)lene oxide-modified (meth)acrylate, tribromophenolethy(propy)lene oxide-modified (meth)acrylate, tetrachlorobisphenol A ethy(propy)lene oxide-modified di(meth)acrylate, tetrabromobisphenol A ethy(propy)lene oxide-modified di(meth)acrylate, tetrachlorobisphenol S ethy(propy)lene oxide-modified di(meth)acrylate and tetrabromobisphenol S ethy(propy)lene oxide-modified di(meth)acrylate; a heteroaromatic group-containing vinyl compound such as N-vinylcarbazole and 3-methyl(or ethyl)-N-vinylcarbazole; and a (meth)acrylate compound substituted with a halogen atom, such as 3-chloro-2-hydroxypropyl(meth)acrylate, 3-bromo-2-hydroxypropyl(meth)acrylate, 2,3-dichloropropyl(meth)acrylate and 2,3-dibromopropyl(meth)acrylate.

Examples of the compound having an aromatic ring or(and) a halogen atom in the molecule and further having a sulfur atom in the molecule include a dithio- or polythio(meth)acrylate compound such as phenyl thio(meth)acrylate, 4-phenylethyl thio(meth)acrylate, 4-methoxycarbonylphenyl thio(meth)acrylate, 4-ethoxycarbonylphenyl thio(meth)acrylate, 4-butoxycarbonylphenyl thio(meth)acrylate, 4-tert-butylphenyl thio(meth)acrylate, benzyl thio(meth)acrylate, 4-phenoxydiethylene glycol thio(meth)acrylate, 4-phenoxytetraethylene glycol thio(meth)acrylate, 4-phenoxyhexaethylene glycol thio(meth)acrylate, 4-biphenylyl thio(meth)acrylate and aromatic polyhydroxy compound (e.g., hydroquinone, resorcin, catechol, pyrogallol); an aromatic group-containing thio(meth)acrylate compound such as bisphenol A dithio(meth)acrylate, ethy(propy)lene oxide-modified bisphenol A dithio(meth)acrylate, bisphenol F dithio(meth)acrylate, ethy(propy)lene oxide-modified bisphenol F dithio(meth)acrylate, bisphenol S dithio(meth)acrylate, ethy(propy)lene oxide-modified bisphenol S dithio(meth)acrylate and epichlorohydrin-modified phthalic acid dithio(meth)acrylate; a thio(meth)acrylate compound having an aromatic group substituted with a halogen atom having an atomic weight of chlorine or more, such as trichlorophenolethy(propy)lene oxide-modified thio(meth)acrylate, tribromophenolethy(propy)lene oxide-modified thio(meth)acrylate, tetrachlorobisphenol A ethy(propy)lene oxide-modified dithio(meth)acrylate, tetrabromobisphenol A ethy(propy) lene oxide-modified dithio(meth)acrylate, tetrachlorobisphenol S ethy(propy)lene oxide-modified dithio(meth)acrylate and tetrabromobisphenol S ethy(propy)lene oxide-modified dithio(meth)acrylate; and a thio(meth)acrylate compound substituted with a halogen atom, such as 3-chloro-2-hydroxypropyl thio(meth)acrylate, 3-bromo-2-hydroxypropyl thio (meth)acrylate, 2,3-dichloropropyl thio(meth)acrylate and 2,3-dibromopropyl thio(meth)acrylate.

Other examples of the compound having an ethylenically unsaturated bond include an addition-polymerizable compound of undergoing polymerization through ring-opening sigma bond cleavage. Such a compound is described in K. J. Ivin and T. Saegusa (compilers), Chap. 1 "General Thermodynamics and Mechanistic Aspects of Ring-Opening Polymerization", pp. 1-82, and Chap. 2 "Ring Opening Polymerization via Carbon-Carbon Sigmabond Cleavage", pp. 83-119, Elsevier, New York (1984); W. J. Bailey et al., *J. Macromol. Sci.-Chem.*, Vol. A21, pp. 1611-1639 (1984); and I. Cho and K.-D. Ahn, *J. Polym. Sci., Polym. Lett. Ed.*, Vol. 15, pp. 751-753 (1977). Specific examples thereof include a vinylcyclopropane such as 1,1-dicyano-2-vinylcyclopropane, 1,1-dichloro-2-vinylcyclopropane, diethyl 2-vinylcyclopropane-1,1-dicarboxylate (EVCD), ethyl 1-acetyl-2-vinyl-1-cyclopropanecarboxylate (EAVC) and ethyl 1-benzoyl-2-vinyl-1-cyclopropanecarboxylate (EBVC). One of these compounds may be used alone, a plurality thereof may be mixed and used, or a mixture with the above-described (meth)acrylic compound or vinyl compound may be used.

Also, specific examples of the amide monomer of an unsaturated carboxylic acid and an aliphatic polyvalent amine compound include methylenebisacrylamide, methylenebismethacrylamide, 1,6-hexamethylenebisacrylamide, 1,6-hexamethylenebismethacrylamide, diethylenetriaminetrisacrylamide, xylylenebisacrylamide, xylylenebismethacrylamide, N-phenylmethacrylamide, and diacetoneacrylamide.

Other examples include a polyisocyanate compound having two or more isocyanate groups per molecule described in JP-B-48-41708 (the term "JP-B" as used herein means an "examined Japanese patent publication"), and a vinyl urethane compound having two or more polymerizable vinyl groups per molecule, where a hydroxy group-containing vinyl monomer represented by the formula $CH_2=C(R)COOCH_2CH(R')OH$ (wherein each of R and R' independently represents a hydrogen atom or a methyl group) is added.

Also, urethane acrylates described in JP-A-51-37193, polyester acrylates described in JP-A-48-64183, JP-B-49-43191 and JP-B-52-30490, and a polyfunctional acrylate or methacrylate of an epoxy resin and a (meth)acrylic acid or the like, may be used.

Furthermore, those described as a photocurable monomer or oligomer in *Nippon Secchaku Kyokaishi* (*Journal of the Adhesion Society of Japan*), Vol. 20, No. 7, pp. 300-308 may be used.

In addition, examples of the phosphorus-containing monomer include mono(2-acryloyloxyethyl) acid phosphate (Light Ester PA, trade name, produced by Kyoeisha Chemical Co., Ltd.) and mono(2-methacryloyloxyethyl) acid phosphate (Light Ester PM, trade name, produced by Kyoeisha Chemical Co., Ltd.), and also include Ripoxy VR-60 (trade name, produced by Showa Highpolymer Co., Ltd.) and Ripoxy VR-90 (trade name, produced by Showa Highpolymer Co., Ltd.), which are an epoxy acrylate-based monomer.

Also, NK Ester M-230G (trade name, produced by Shin-Nakamura Chemical Co., Ltd.) and NK Ester 23G (trade name, produced by Shin-Nakamura Chemical Co., Ltd.) may be used.

Other examples include triacrylates (Aronix M-315, trade name, produced by Toagosei Chemical Industry Co., Ltd.; Aronix M-325, trade name, produced by Toagosei Chemical Industry Co., Ltd.), 2,2'-bis(4-acryloxy•diethoxyphenyepropane (NK Ester A-BPE-4, trade name, produced by Shin-Nakamura Chemical Co., Ltd.), and tetramethylolmethane tetraacrylate (NK Ester A-TMMT, trade name, produced by Shin-Nakamura Chemical Co., Ltd.).

As the polymerizable urethane acrylate resin, TSR-1920B, TSR-1938 (produced by Teijin Limited) and SCR-500 (produced by Japan Synthetic Rubber Co., Ltd.) are also preferred in view of thermal and mechanical properties.

The cationic polymerizable compound for use in the present invention is a compound of starting its polymerization under the action of an acid generated by the two-photon absorption compound and a cationic polymerization initiator, and examples thereof include the compounds described in J. V. Crivello, *Chemtech. Oct.*, page 624 (1980), JP-A-62-149784, and *Nippon Secchaku Kyokaishi* (*Journal of the Adhesion Society of Japan*), Vol. 26, No. 5, pp. 179-187 (1990).

The cationic polymerizable compound for use in the present invention is preferably a compound having at least one more oxirane ring, oxetane ring or vinyl ether group moiety in the molecule, more preferably a compound having an oxirane ring moiety.

Specifically, the cationic polymerizable compound includes the following cationic polymerizable monomers and prepolymers (e.g., dimer, oligomer) comprising such a cationic polymerizable monomer.

Specific examples of the cationic polymerizable monomer having an oxirane ring include compounds such as glycerol diglycidyl ether, glycerol triglycidyl ether, diglycerol triglycidyl ether, diglycerol polyglycidyl ether, pentaerythritol polyglycidyl ether, 1,4-bis(2,3-epoxypropoxyperfluoroisopropyl)cyclohexane, sorbitol tetraglycidyl ether, trimethylolpropane diglycidyl ether, trimethylolpropane monoglycidyl ether, trimethylolpropane triglycidyl ether, resorcin diglycidyl ether, 1,6-hexanediol diglycidyl ether, ethylene glycol diglycidyl ether, ethylene glycol monoglycidyl ether, polyethylene glycol diglycidyl ether, propylene glycol diglycidyl ether, propylene glycol monoglycidyl ether, neopentyl glycol diglycidyl ether, neopentyl glycol monoglycidyl ether, phenyl glycidyl ether, p-tert-butylphenyl glycidyl ether, diglycidyl adipate, diglycidyl phthalate, dibromophenyl glycidyl ether, dibromoneopentyl glycol diglycidyl ether, 1,2,7,8-diepoxyoctane, 1,6-dimethylolperfluorohexanediglycidyl ether, 4,4'-bis(2,3-epoxypropoxyperfluoroisopropyl)diphenyl ether, vinylcyclohexene dioxide, 3,4-epoxycyclohexylmethyl-3',4'-epoxycyclohexane carboxylate, 3,4-epoxycyclohexyloxirane, bis(3,4-epoxycyclohexyl) adipate, bis(3,4-epoxy-6-methyl-cyclohexylmethyl) adipate, 2,2-bis[4-(2,3-epoxypropoxyl)cyclohexyl]propane, 2,2-bis[4-(2,3-epoxypropoxyl)cyclohexyl]hexafluoropropane, 1,2,5,6-diepoxy-4,7-methanoperhydroindene, 2-(3,4-epoxycyclohexyl)-3',4'-epoxy-1,3-dioxane-5-spirocyclohexane, 1,2-ethylenedioxy-bis(3,4-epoxycyclohexylmethane), 4',5'-epoxy-2'-methylcyclohexylmethyl-4,5-epoxy-2-methylcyclohexane carboxylate, ethylene glycol-bis(3,4-epoxycyclohexane carboxylate), bis(3,4-epoxycyclohexylmethyl) adipate, di-2,3-epoxycyclopentyl ether, vinyl glycidyl ether, allyl glycidyl ether, 2-ethylhexyl glycidyl ether, styrene oxide, p-bromostyrene oxide, bisphenol-A-diglycidyl ether, tetrabromobisphenol-A-diglycidyl ether and bisphenol-F-diglycidyl ether.

Also, HS-681 (produced by Asahi Denka Co., Ltd.), SOMOS8100 (produced by DMS-SOMOS), SCR-8100 series (produced by Japan Synthetic Rubber Co., Ltd.), SL-7540 (produced by Vantico) and SCR-701 (produced by D-MEC Ltd. and Japan Synthetic Rubber Co., Ltd.) can be used as the polymerizable epoxy-based resin.

Specific examples of the cationic polymerizable monomer having an oxetane ring include the compounds described above as specific examples of the cationic polymerizable monomers having an oxirane ring, where the oxirane ring is replaced by an oxetane ring.

Specific examples of the cationic polymerizable monomer having a vinyl ether group moiety include compounds such as vinyl-2-chloroethyl ether, vinyl-n-butyl ether, vinyl-tert-butyl ether, ethylene glycol divinyl ether, ethylene glycol monovinyl ether, propylene glycol divinyl ether, propylene glycol monovinyl ether, neopentyl glycol divinyl glycol, neopentyl glycol monovinyl glycol, glycerol divinyl ether, glycerol trivinyl ether, triethylene glycol divinyl ether, trimethylolethane trivinyl ether, trimethylolpropane monovinyl ether, trimethylolpropane divinyl ether, trimethylolpropane trivinyl ether, diglycerol trivinyl ether, sorbitol tetravinyl ether, allyl vinyl ether, 2,2-bis(4-cyclohexanol)propane divinyl ether, 2,2-bis(4-cyclohexanol)trifluoropropane divinyl ether, 1,4-cyclohexanedimethanol divinyl ether, 4-vinyl ether styrene, hydroquinone divinyl ether, phenyl vinyl ether, bisphenol A divinyl ether, tetrabromobisphenol A divinyl ether, bisphenol F divinyl ether, phenoxyethylene vinyl ether and p-bromophenoxyethylene vinyl ether.

In particular, the (a) non-resonant polymer two-photon absorption compound for use in the non-resonant two-photon absorption recording material of the present invention is preferably a compound having a structure represented by the following formula (1):

[Chem. 8]

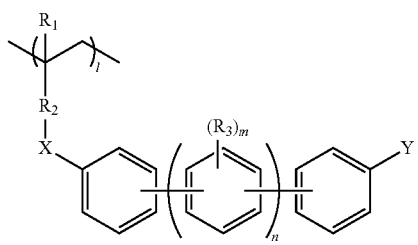

Formula (1)

(wherein X and Y represent substituents both having a Hammett sigma para value (σp value) of 0 or more and may be the same as or different from each other; n represents an integer of 1 to 4; $R_1$ represents a hydrogen atom or a substituent; $R_2$ represents a divalent substituent; $R_3$ represents a substituent; when a plurality of $R_1$, $R_2$ or $R_3$ are present, $R_1$, $R_2$ or $R_3$ may be the same as or different from every other $R_1$, $R_2$ or $R_3$; l represents an integer of 1 or more; and m represents an integer of 0 to 4).

In formula (1), Y represents a so-called electron-withdrawing group of which σp value in the Hammett equation takes a positive value, and is preferably, for example, a trifluoromethyl group, a heterocyclic group, a halogen atom, a cyano group, a nitro group, an alkylsulfonyl group, an arylsulfonyl group, a sulfamoyl group, a carbamoyl group, an acyl group, an acyloxy group or an alkoxycarbonyl group, more preferably a trifluoromethyl group, a cyano group, an acyl group, an acyloxy group or an alkoxycarbonyl group, still more preferably a trifluoromethyl group, a cyano group or a benzoyl group, and most preferably a trifluoromethyl group. Out of these substituents, the alkylsulfonyl group, arylsulfonyl group, sulfamoyl group, carbamoyl group, acyl group, acyloxy group and alkoxycarbonyl group may further have a substituent for imparting solubility in a solvent or other various purposes, and preferred examples of the substituent include an alkyl group, an alkoxy group, an alkoxyalkyl group, and an aryloxy group.

X is similar to Y and is a substituent (linking group) having two bonding sites, and examples thereof include a trifluoromethylene group, a heterocyclic group, an alkylsulfonyl group, an arylsulfonyl group, a sulfamoyl group, a carbamoyl group, an acyl group, an acyloxy group and an alkoxycarbonyl group. X is preferably an acyl group, an acyloxy group or an alkoxycarbonyl group, and most preferably a benzoyl group. Out of these substituents, the alkylsulfonyl group, arylsulfonyl group, sulfamoyl group, carbamoyl group, acyl group, acyloxy group and alkoxycarbonyl group may further have a substituent for imparting solubility in a solvent or other various purposes, and preferred examples of the substituent include an alkyl group, an alkoxy group, an alkoxyalkyl group, and an aryloxy group.

n represents an integer of 1 or 4 and is preferably 2 or 3, most preferably 2. If n becomes 5 or more, the linear absorption comes to appear on the long wavelength side, and non-resonant two-photon absorption recording using recording light in a wavelength region shorter than 700 nm cannot be performed. Also, m represents an integer of 0 to 4.

$R_1$ represents a hydrogen atom or a substituent and is preferably a hydrogen atom, an alkyl group, an alkoxy group, an aryl group, an alkoxyalkyl group or an aryloxy group, more preferably a hydrogen atom, an alkyl group, an alkoxy group or an aryl group, and most preferably a hydrogen atom or an alkyl group.

$R_2$ represents a divalent substituent (linking group) and is preferably a carbonyl group, an oxy group, an alkylene group, an arylene group or a group formed by combining these groups, more preferably an ester bond (a group composed of a carbonyl group and an oxy group), an alkylene oxide group (a group composed of an alkylene group and an oxy group), an arylene group, or a group formed by combining these groups. Such a group may further have a substituent for imparting solubility in a solvent or other various purposes, and preferred examples of the substituent include a hydroxyl group, an alkyl group, an alkoxy group, an alkoxyalkyl group, and an aryloxy group.

$R_3$ represents a substituent, and the substituent is not particularly limited. Specific examples thereof include an alkyl group, an alkoxy group, an alkoxyalkyl group, and an aryloxy group.

In the compound having a structure represented by formula (1), X and Y are preferably a so-called electron-withdrawing group of which σp value in the Hammett equation takes a positive value, and this is described below.

According to T. Kogej, et al., *Chem. Phys. Lett.*, 298, 1 (1998), the two-photon absorption efficiency of an organic compound, that is, the two-photon absorption cross-sectional area 8, has the following relationship with the imaginary part of the third-order molecular polarizability (second-order hyperpolarizability) γ.

[Math. 1]

$$\delta(\omega) = \left(\frac{3\pi h v^2}{n^2 c^2 \varepsilon_0}\right) \mathrm{Im}\gamma(-\omega; \omega, -\omega, \omega) \quad \text{Mathematical Formula (1)}$$

wherein c: light speed, v: frequency, n: refractive index, $\varepsilon_0$: dielectric constant in vacuum, ω: number of vibration of photon, and Im: imaginary part. The imaginary part (Imγ) of γ has the following relationship with Mge: dipole moment between Ig> and Ie>, Mge': dipole moment between Ig> and Ie'>, Δμge: difference in dipole moment between Ig> and Ie>, Ege: transition energy, and Γ: damping factor.

[Math. 2]

$$\mathrm{Im}\gamma(-\omega; \omega, -\omega, \omega) = \mathrm{Im} P \sum_{e'} \begin{bmatrix} \frac{Mge^2 \Delta\mu ge^2}{(Ege - \hbar\omega - i\Gamma ge)} + \\ (Ege - 2\hbar\omega - i\Gamma ge) \\ (Ege - \hbar\omega - i\Gamma ge) \\ \frac{Mge^2 Mee'^2}{(Ege - \hbar\omega - i\Gamma ge)} - \\ (Ege' - 2\hbar\omega - i\Gamma ge') \\ (Ege - \hbar\omega - i\Gamma ge) \\ \frac{Mge^4}{(Ege - \hbar\omega - i\Gamma ge)} \\ (Ege + \hbar\omega + i\Gamma ge) \\ (Ege - \hbar\omega - i\Gamma ge) \end{bmatrix} \quad \text{Mathematical Formula (2)}$$

wherein P represents a commutative operator.

Accordingly, when the value of mathematical formula (2) is computed, the two-photon absorption cross-sectional area of a compound can be predicted. For this reason, the most stable structure of the ground state is computed by a DFT method using a B3LYP functional with a 6-31G* basis function, and Mge, Mee' and Ege are computed based on the result, whereby the value of Imγ can be computed. For example, assuming that the maximum Imγ value obtained by the computation of a quaterphenyl compound that is a compound having a structure represented by formula (1) where a methoxy group as an electron-donating substituent is substituted on X and Y is 1, the relative value of the maximum Imγ value of a molecule having, as other substituents, a so-called electron-withdrawing group of which σp value in the Hammett equation takes a positive value becomes large.

As regards the compound having a structure represented by formula (1), Imγ is small in the case of a quaterphenyl compound where a methoxy group as an electron-donating group is substituted on X and Y, and Imγ greatly increases in general in the case of a molecule where an electron-withdrawing substituent is substituted on both X and Y. As described above, the two-photon absorption cross-sectional area δ is theoretically proportional to the imaginary part of the third-order hyperpolarizability γ, that is, Imγ, and judging from the computation thereof, a structure where an electron-withdrawing substituent is substituted on both X and Y is preferred.

The compound having a structure represented by formula (1) is preferably a compound having a structure represented by the following formula (2):

[Chem. 9]

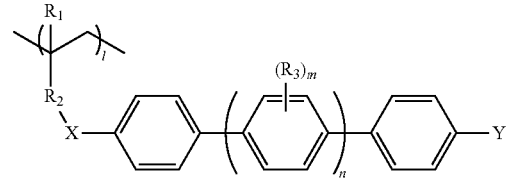

Formula (2)

In formula (2), X, Y, n, $R_1$, $R_2$, $R_3$, l and m are the same as those specified in formula (1).

In the compound having a structure represented by formula (1) or (2), X and Y may be the same as or different from each other but are preferably different, because the two-photon absorption cross-sectional area tends to become large.

Furthermore, the compound having a structure represented by formula (2) is preferably a compound having a structure represented by the following formula (3):

[Chem. 10]

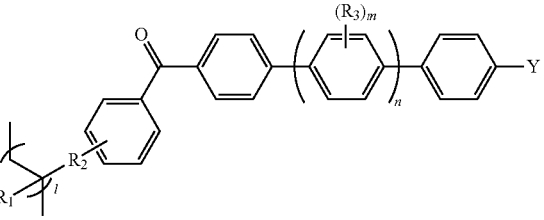

Formula (3)

In formula (3), Y, n, $R_1$, $R_2$, $R_3$, l and m are the same as those specified in formulae (1) and (2).

In addition, the compound having a structure represented by formula (3) is preferably a compound having a structure represented by the following formula (4):

[Chem. 11]

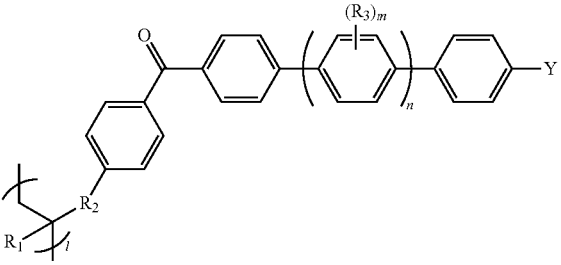

Formula (4)

In formula (4), Y, n, $R_1$, $R_2$, $R_3$, l and m are the same as those specified in formulae (1) to (3).

The non-resonant polymer two-photon absorption compound in the present invention is preferably a compound represented by the following formula (5):

[Chem. 12]

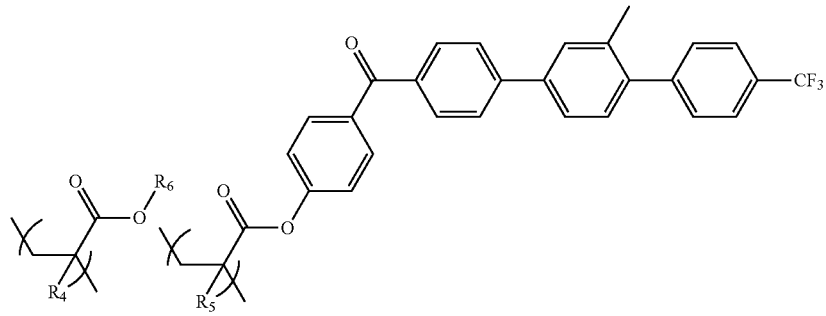

Formula (5)

(wherein each of $R_4$, $R_5$ and $R_6$ represents a hydrogen atom or a substituent, and $R_4$, $R_5$ and $R_6$ may be the same as or different from each other).

Each of $R_4$, $R_5$ and $R_6$ independently represents a hydrogen atom or a substituent and is preferably a hydrogen atom, an alkyl group, an alkoxy group, an aryl group, an alkoxyalkyl group or an aryloxy group, more preferably a hydrogen atom, an alkyl group, an alkoxy group or an aryl group, and most preferably a hydrogen atom or an alkyl group.

It is also preferred that the non-resonant polymer two-photon absorption compound in the present invention is a compound represented by the following formula (6):

[Chem. 13]

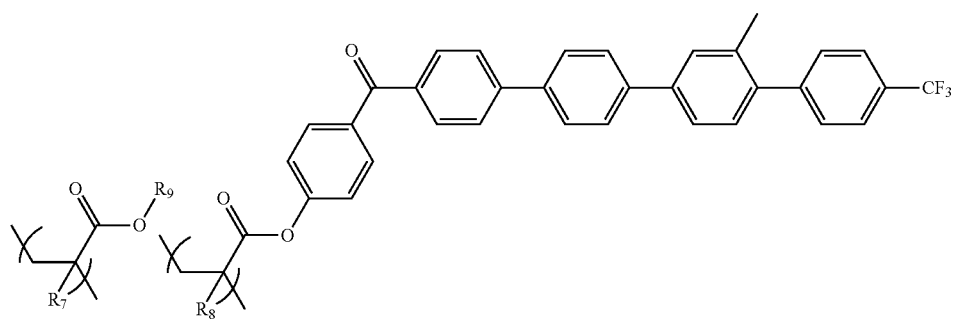

Formula (6)

(wherein each of $R_7$, $R_8$ and $R_9$ represents a hydrogen atom or a substituent, and $R_7$, $R_8$ and $R_9$ may be the same as or different from each other).

Each of $R_7$, $R_8$ and $R_9$ independently represents a hydrogen atom or a substituent and is preferably a hydrogen atom, an alkyl group, an alkoxy group, an aryl group, an alkoxyalkyl group or an aryloxy group, more preferably a hydrogen atom, an alkyl group, an alkoxy group or an aryl group, and most preferably a hydrogen atom or an alkyl group.

Specific examples of the compounds of the present invention are not particularly limited but include the followings.

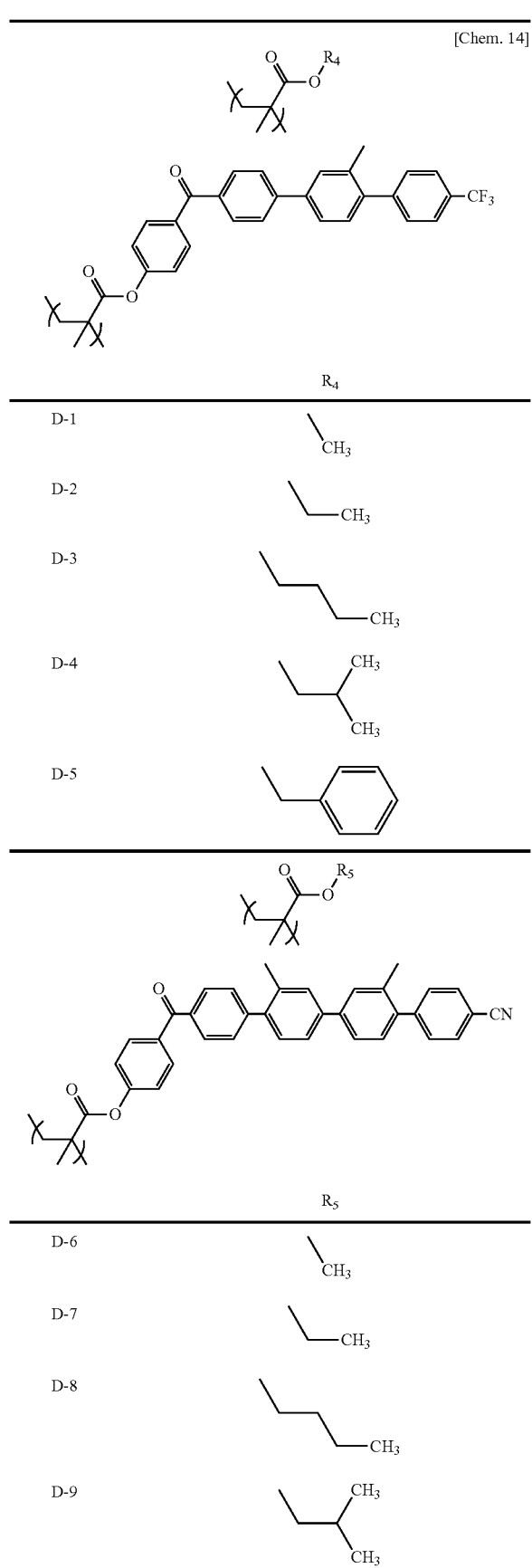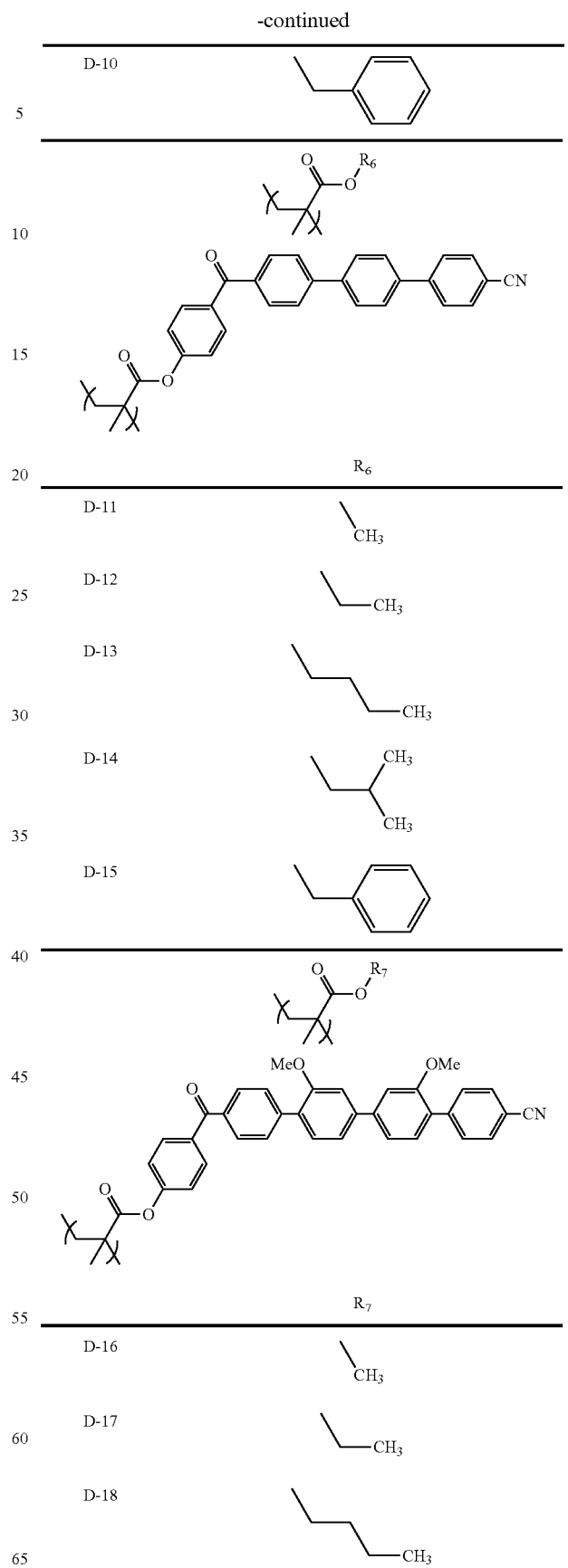

-continued
| | |
|---|---|
| D-19 | 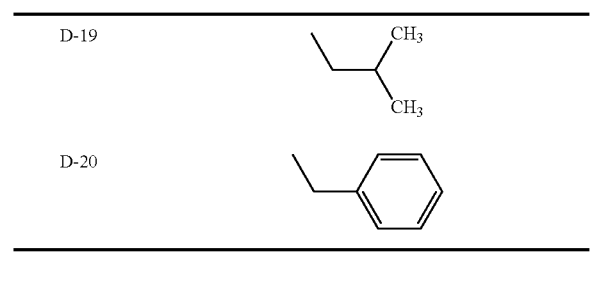 |
| D-20 | |
[Chem. 15]
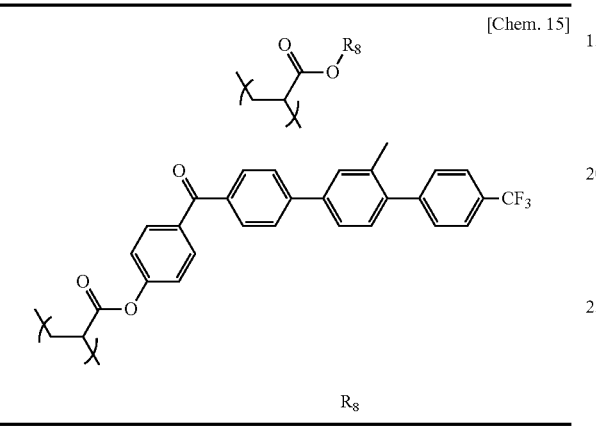
| | $R_8$ |
|---|---|
| D-21 | 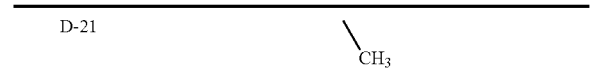 |
| D-22 |  |
| D-23 |  |
| D-24 |  |
| D-25 |  |
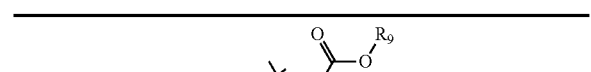
| | $R_9$ |
|---|---|
| D-26 | 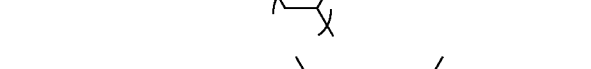 |
-continued
| | |
|---|---|
| D-27 | 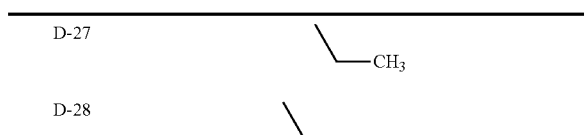 |
| D-28 | |
| D-29 | |
| D-30 | |
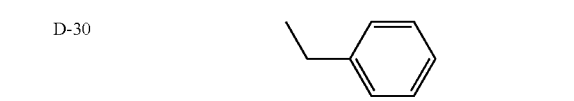
| | $R_{10}$ |
|---|---|
| D-31 | 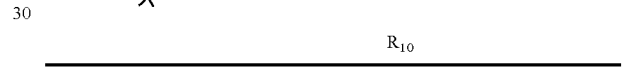 |
| D-32 | 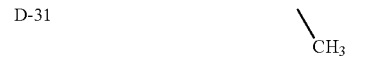 |
| D-33 |  |
| D-34 |  |
| D-35 |  |
| | $R_{11}$ |
|---|---|

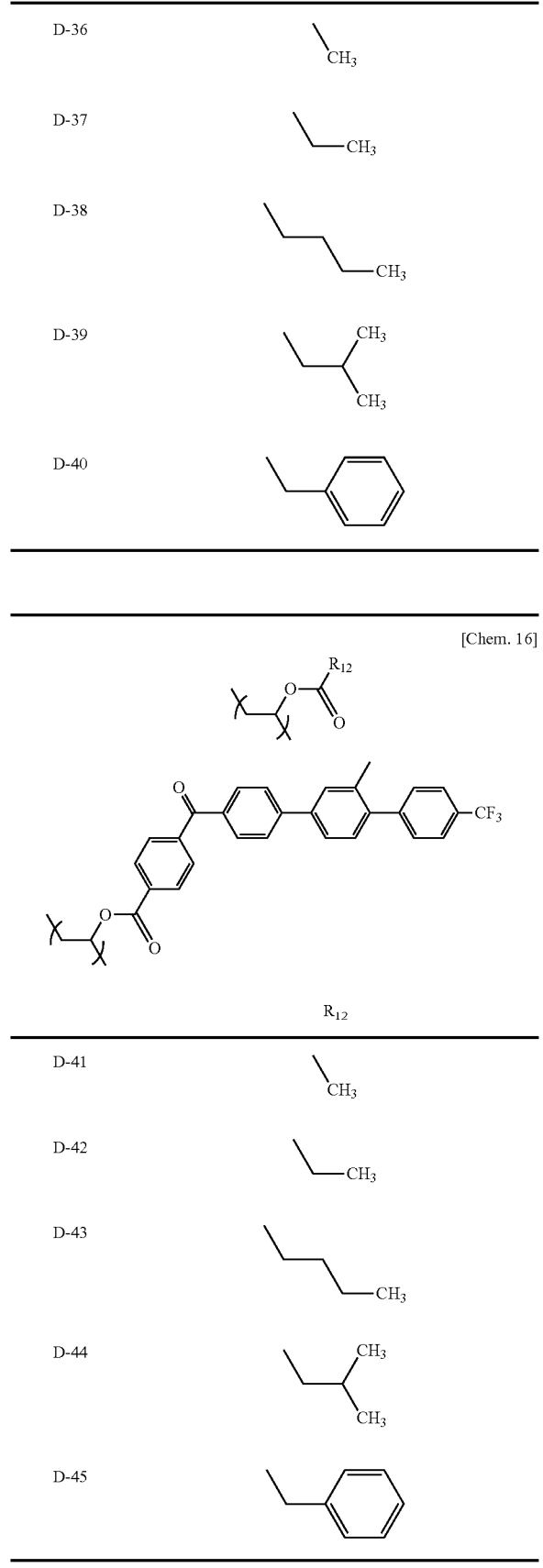
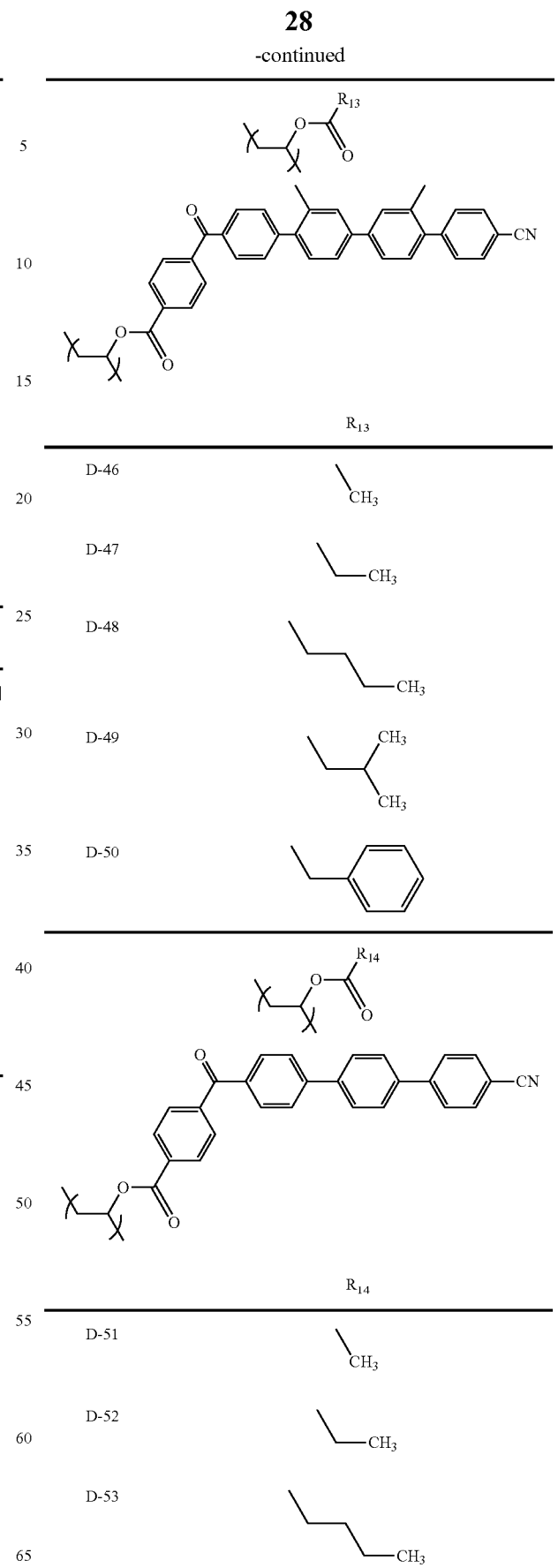

| | | | | |
|---|---|---|---|---|
| D-54 | 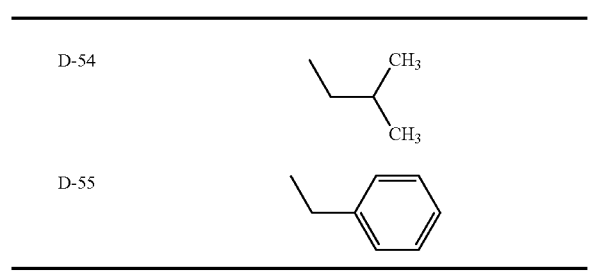 | | D-62 | 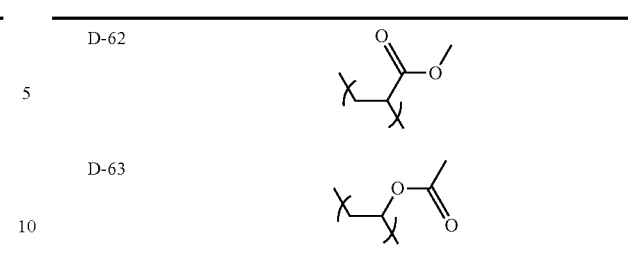 |
| D-55 | | | D-63 | |
| | | | D-64 | |
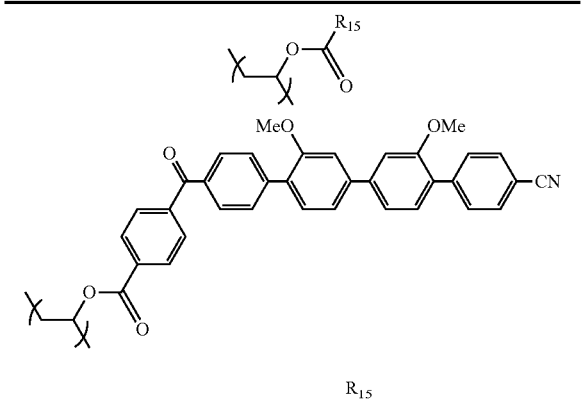
| | |
|---|---|
| | $R_{15}$ |
| D-56 | CH₃ |
| D-57 | CH₃ |
| D-58 | CH₃ |
| D-59 | CH₃ / CH₃ |
| D-60 | (phenethyl) |
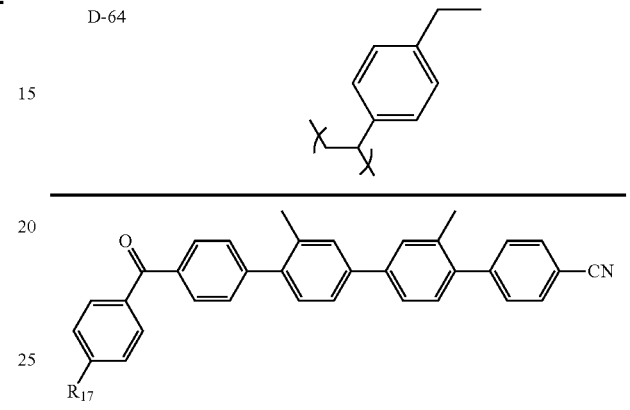
| | |
|---|---|
| | $R_{17}$ |
| D-65 | 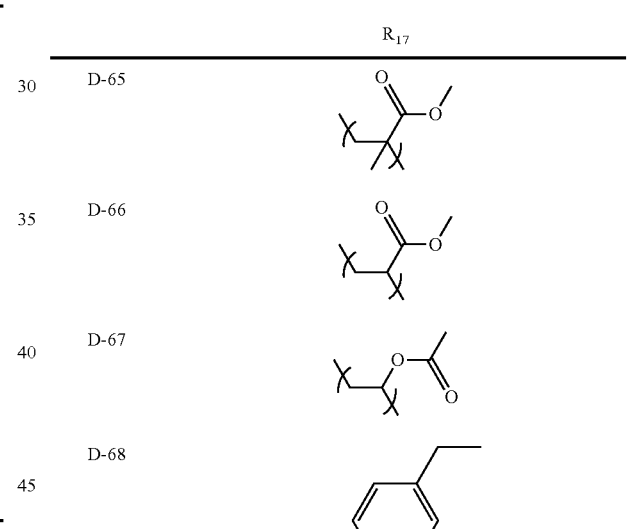 (top) |
| D-66 | |
| D-67 | |
| D-68 | |
[Chem. 17]
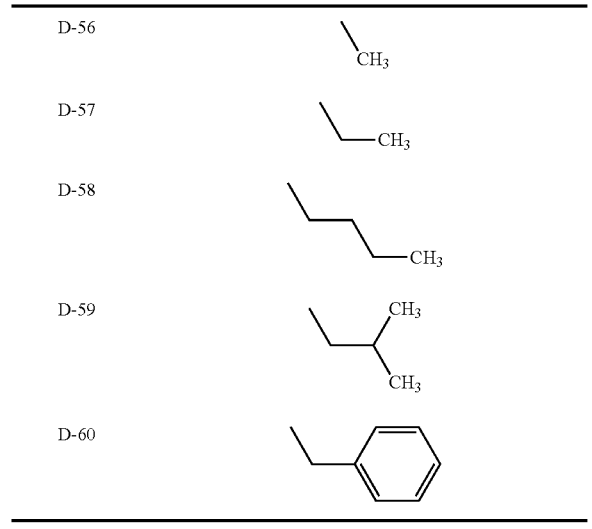
| | |
|---|---|
| | $R_{16}$ |
| D-61 | 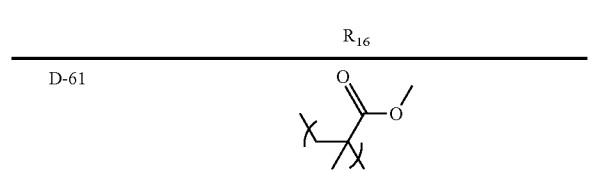 |
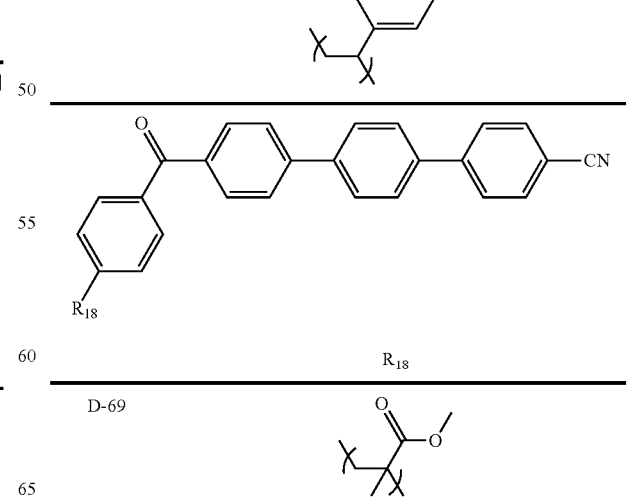
| | |
|---|---|
| | $R_{18}$ |
| D-69 | |

-continued
D-70
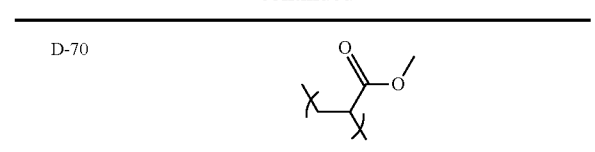
D-71
D-72
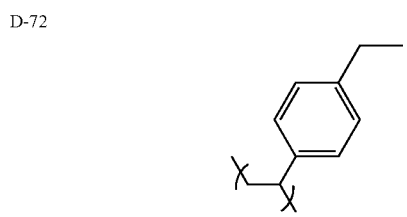
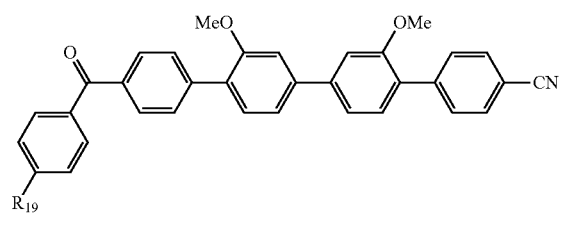
R_{19}
D-73
D-74
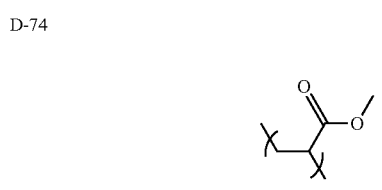
D-75
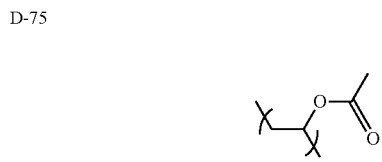
D-76
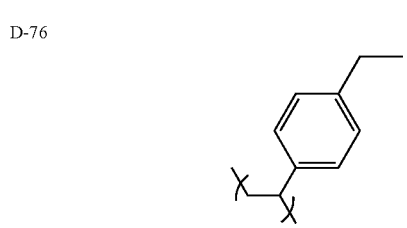
[Chem. 18]
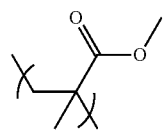
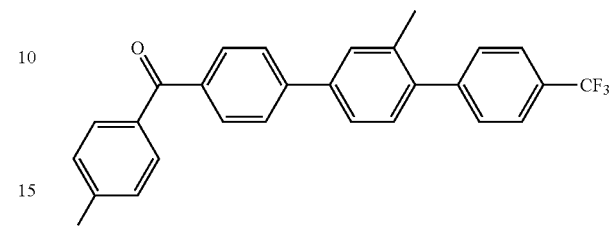
R_{20}
D-77
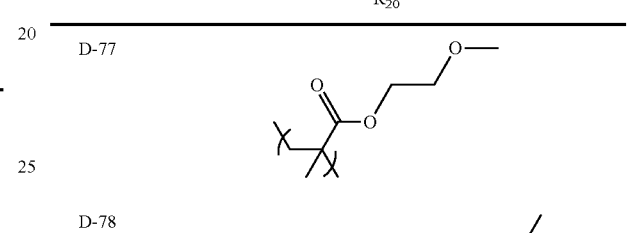
D-78
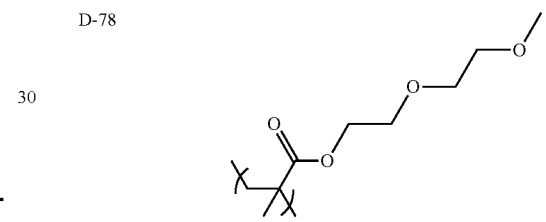
D-79
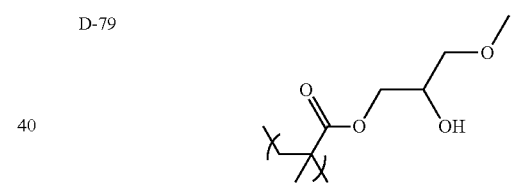
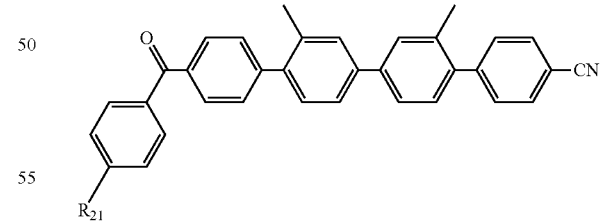
R_{21}
D-80
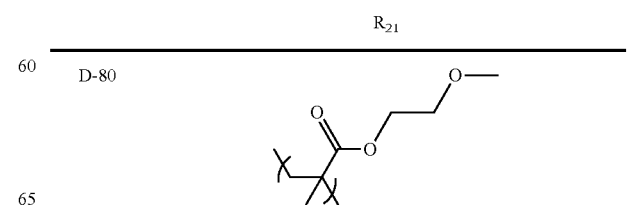

33
-continued
D-81
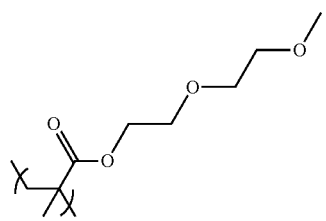
D-82
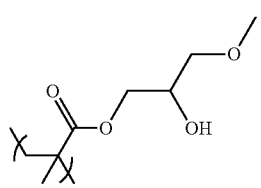
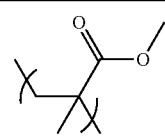
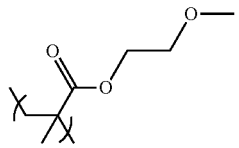
D-83
D-84
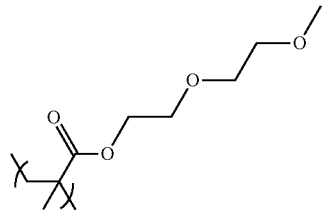
D-85
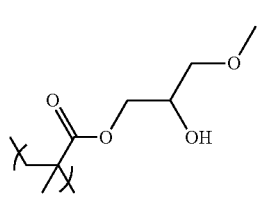
34
-continued
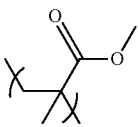
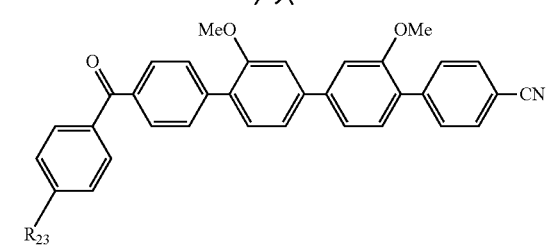
R₂₃
D-86
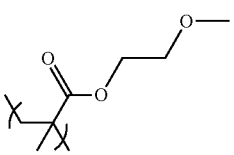
D-87
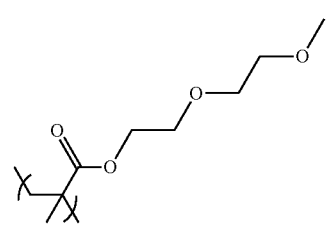
D-88
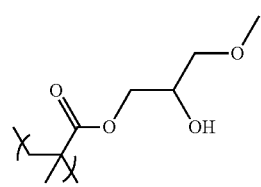
[Chem. 19]
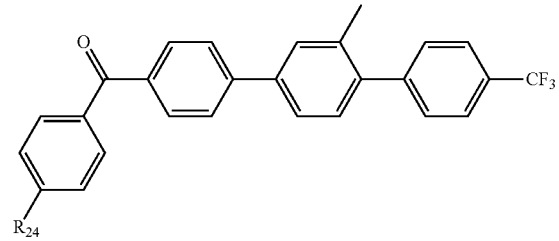
R₂₄
D-89
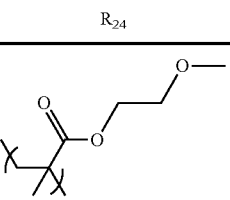

-continued
D-90
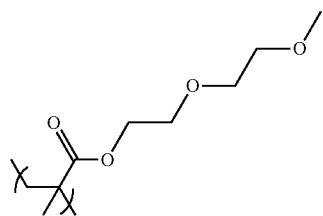
D-91
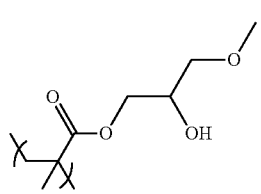
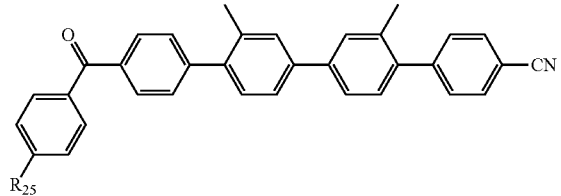
| $R_{25}$ |
|---|
| D-92 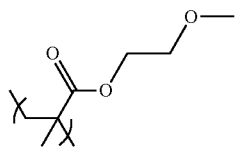 |
| D-93 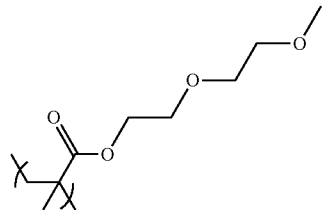 |
| D-94 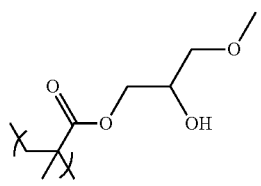 |
-continued
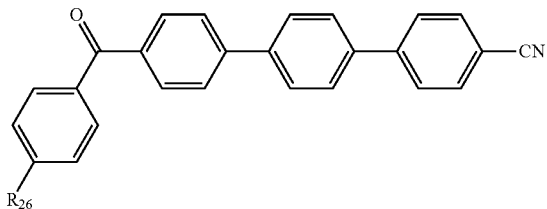
| $R_{26}$ |
|---|
| D-95 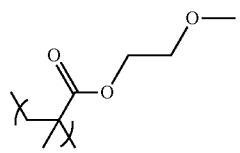 |
| D-96 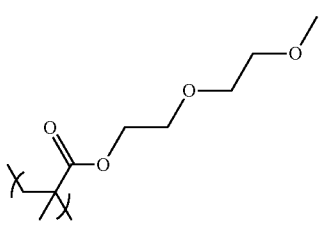 |
| D-97 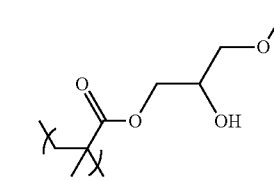 |
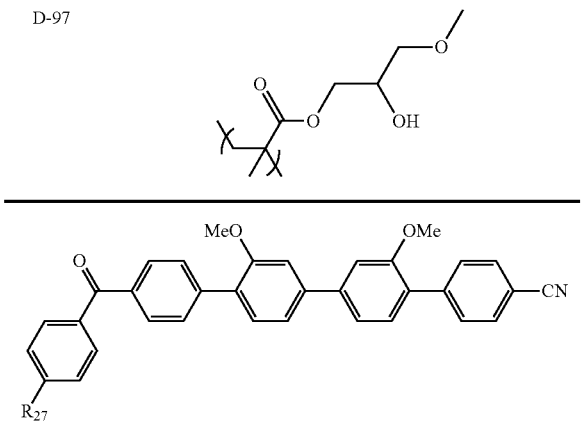
| $R_{27}$ |
|---|
| D-98 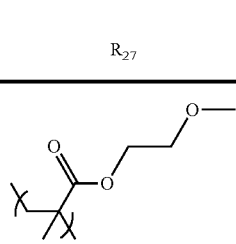 |
| D-99 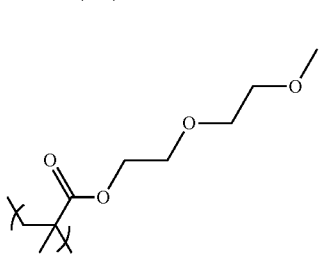 |

| | |
|---|---|
| D-100 | 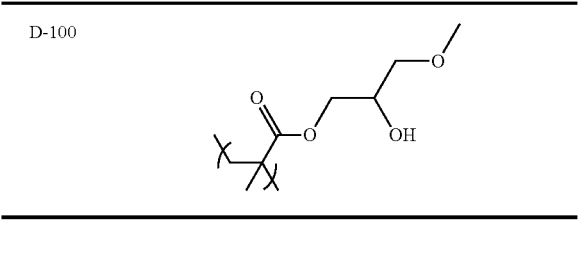 |
[Chem. 20]
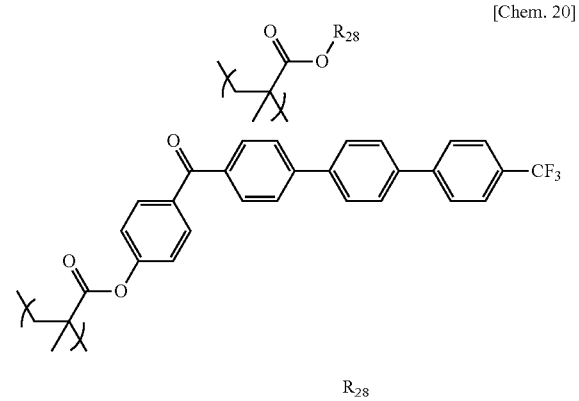
| | $R_{28}$ |
|---|---|
| D-101 | CH₃ |
| D-102 | CH₃ |
| D-103 | CH₃ / CH₃ |
| D-104 | CH₃ / CH₃ |
| D-105 | (benzyl-ethyl) |
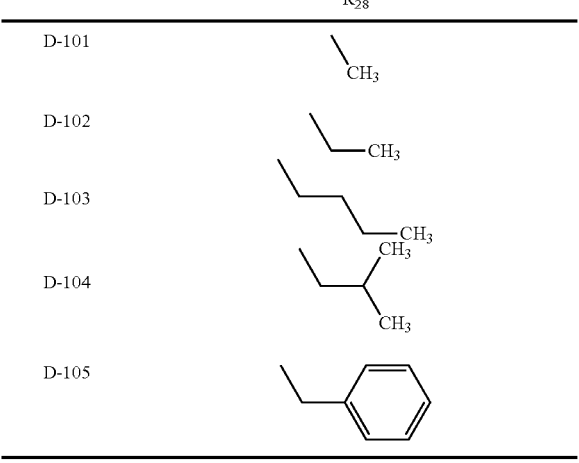
| | $R_{29}$ |
|---|---|
| D-106 | CH₃ |
| D-107 | CH₃ |
| | |
|---|---|
| D-108 | 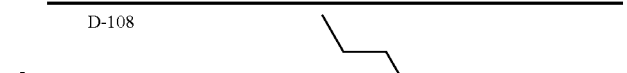 |
| D-109 |  |
| D-110 |  |
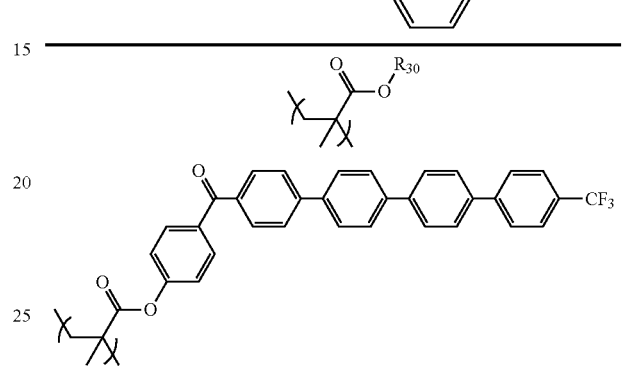
| | $R_{30}$ |
|---|---|
| D-111 | CH₃ |
| D-112 | CH₃ |
| D-113 | 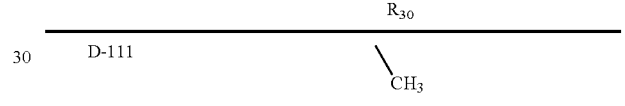 |
| D-114 | 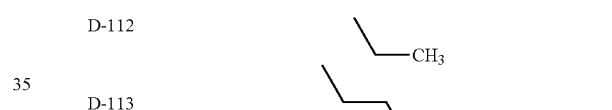 |
| D-115 | (benzyl-ethyl) |
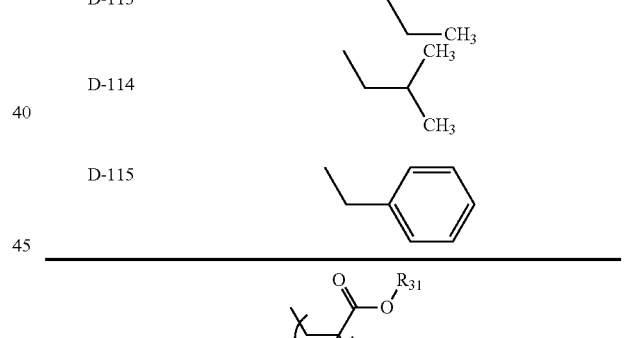
| | $R_{31}$ |
|---|---|
| D-116 | CH₃ |
| D-117 | CH₃ |

-continued
| | |
|---|---|
| D-118 | |
| D-119 | |
| D-120 | |
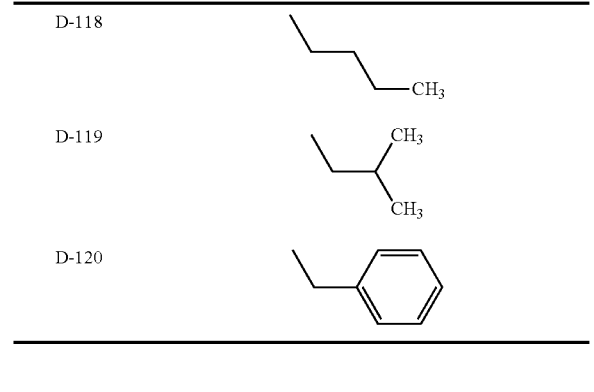
| $R_{32}$ | |
|---|---|
| D-121 | |
| D-122 | |
| D-123 | |
| D-124 | |
| D-125 | |
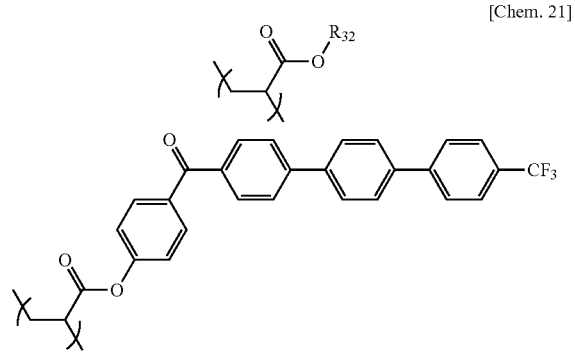
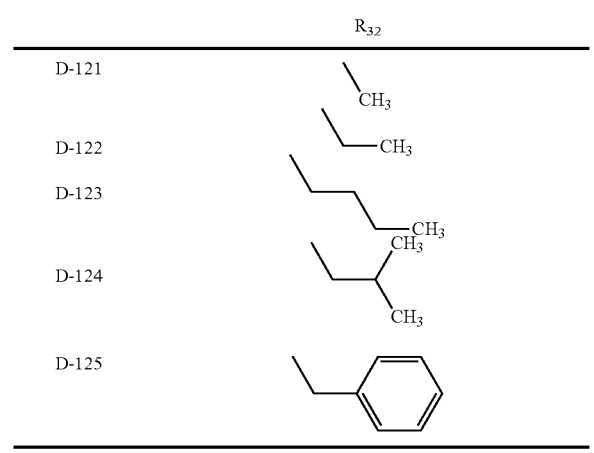
| $R_{33}$ | |
|---|---|
| D-126 | |
-continued
| | |
|---|---|
| D-127 | |
| D-128 | |
| D-129 | |
| D-130 | |
[Chem. 21]
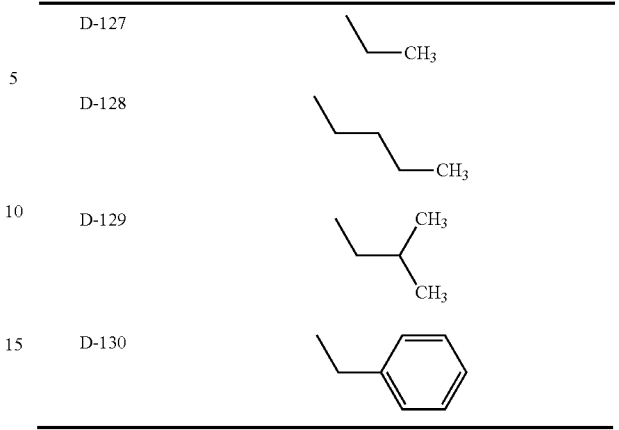
| $R_{34}$ | |
|---|---|
| D-131 | |
| D-132 | |
| D-133 | |
| D-134 | |
| D-135 | |
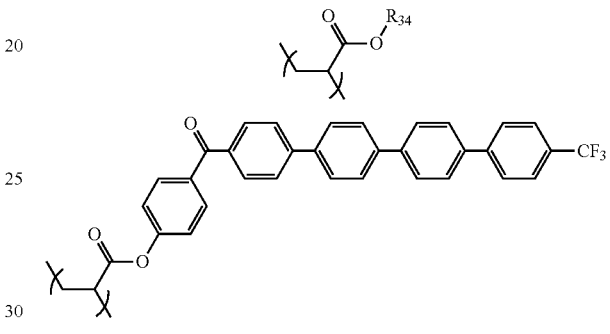
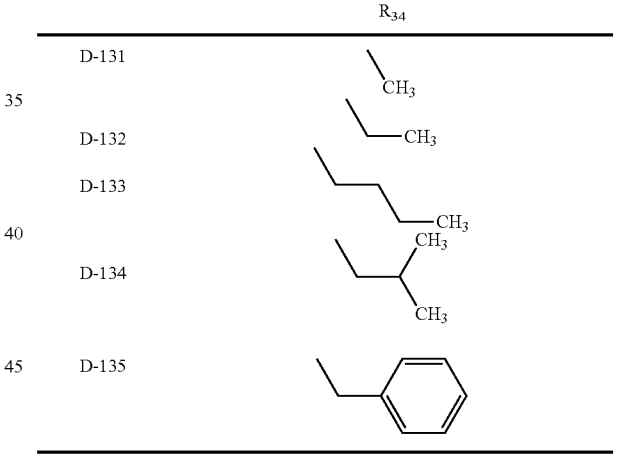
| $R_{35}$ | |
|---|---|
| D-136 | |
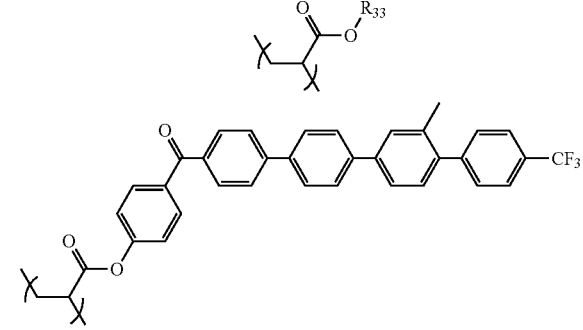
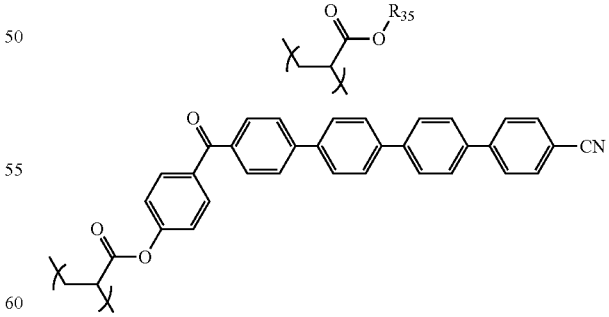

| | |
|---|---|
| D-137 | 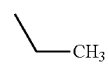 |
| D-138 | 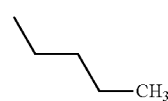 |
| | |
|---|---|
| D-139 | 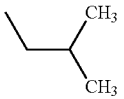 |
| D-140 | 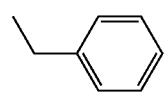 |
[Chem. 22]
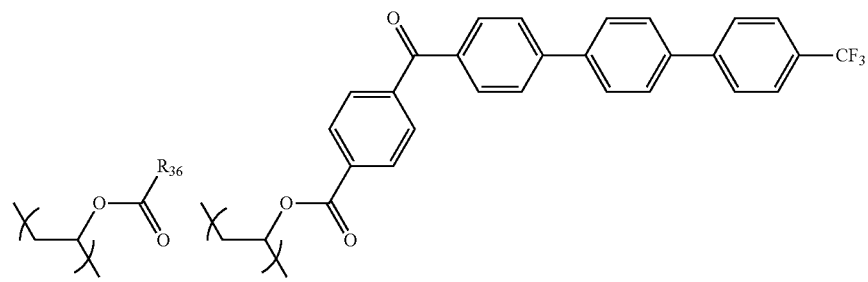
| | $R_{36}$ |
|---|---|
| D-141 |  |
| D-142 | 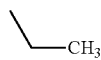 |
| D-143 | 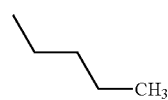 |
| D-144 | 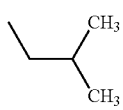 |
| D-145 | 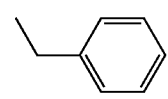 |
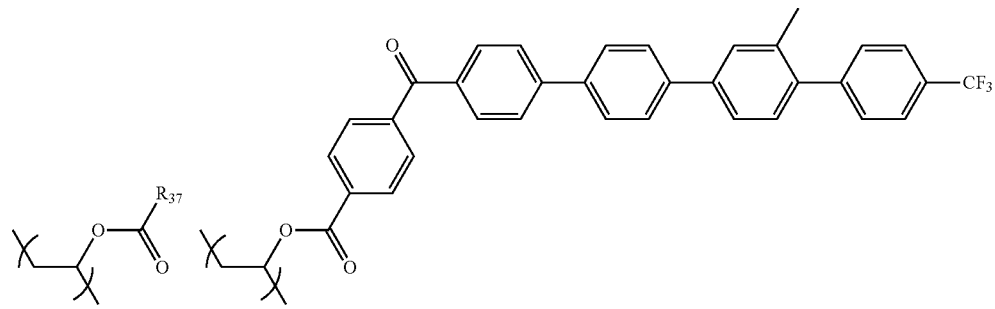
| | $R_{37}$ |
|---|---|
| D-146 |  |
| D-147 | 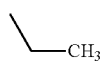 |

-continued
[Chem. 22]
D-148 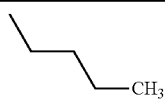
D-149 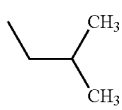
D-150 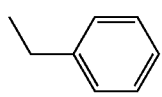
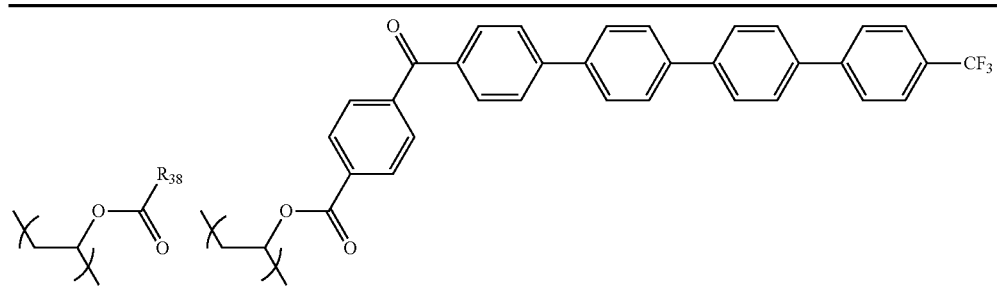
| | $R_{38}$ |
|---|---|
| D-151 |  |
| D-152 |  |
| D-153 | 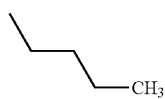 |
| D-154 | 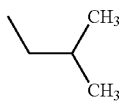 |
| D-155 | 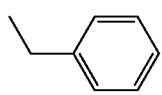 |
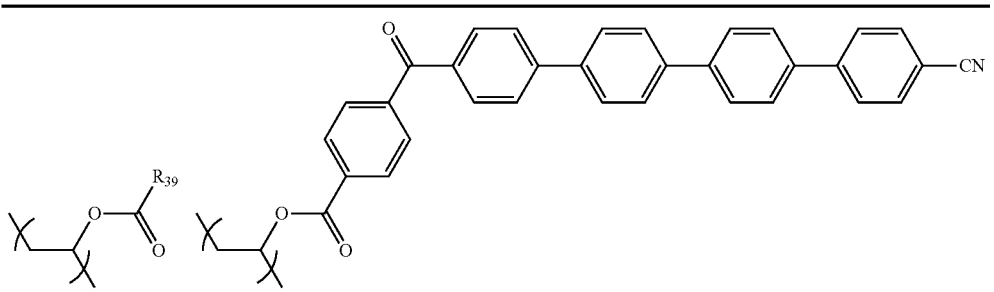
| | $R_{39}$ |
|---|---|
| D-156 |  |
| D-157 |  |

[Chem. 22]
D-158 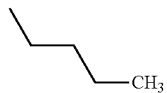
D-159 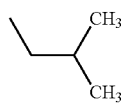
D-160 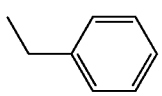
[Chem. 23]
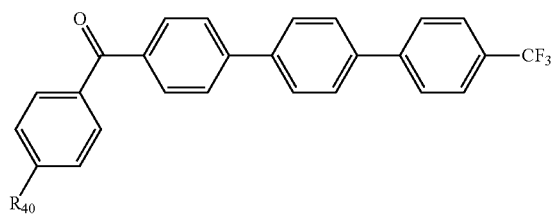
| | $R_{40}$ |
|---|---|
| D-161 | 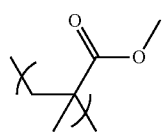 |
| D-162 | 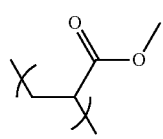 |
| D-163 | 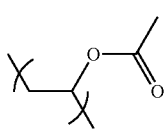 |
| D-164 | 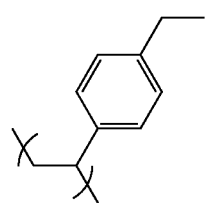 |

[Chem. 23]
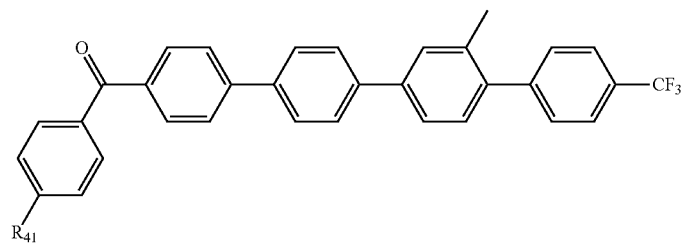
| | $R_{41}$ |
|---|---|
| D-165 | 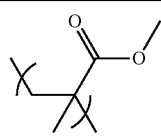 |
| D-166 | 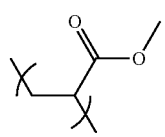 |
| D-167 | 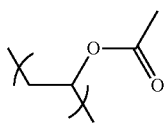 |
| D-168 | 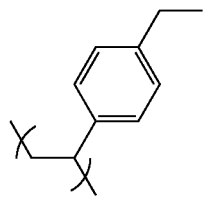 |
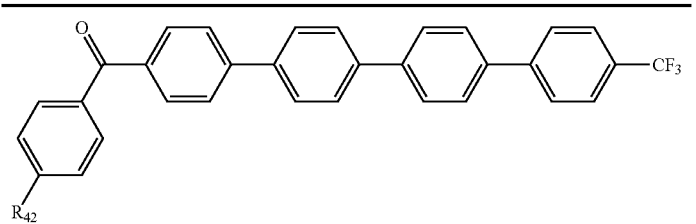
| | $R_{42}$ |
|---|---|
| D-169 | 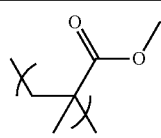 |
| D-170 | 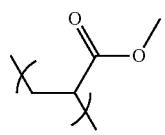 |
| D-171 | 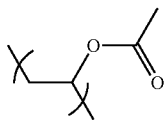 |

-continued
[Chem. 23]
D-172
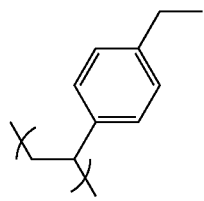
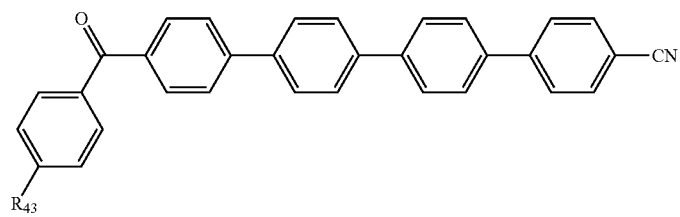
| $R_{43}$ |
|---|
D-173
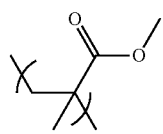
D-174
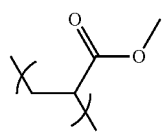
D-175
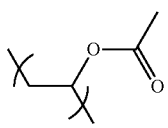
D-176
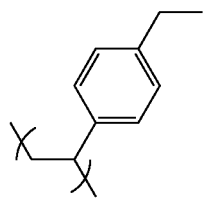

[Chem. 24]
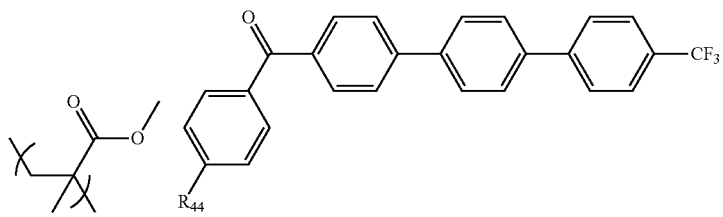
| | $R_{44}$ |
|---|---|
| D-177 | 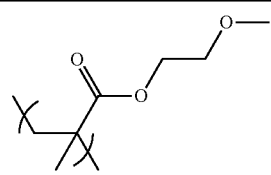 |
| D-178 | 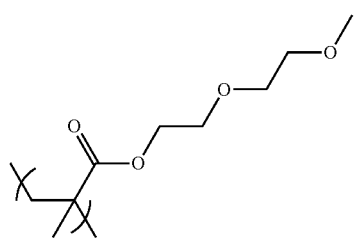 |
| D-179 | 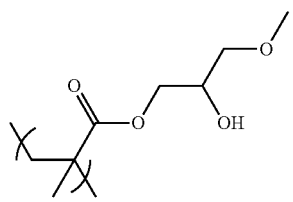 |
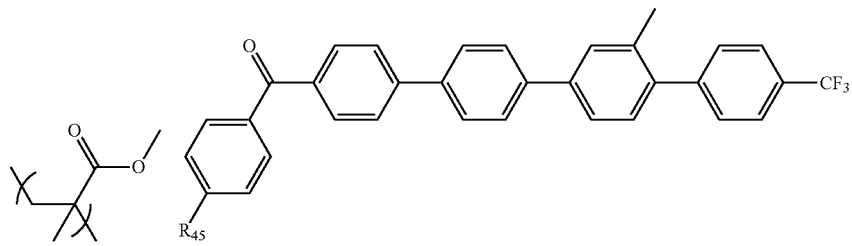
| | $R_{45}$ |
|---|---|
| D-180 | 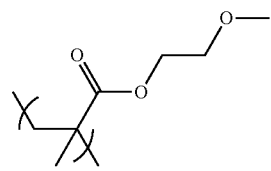 |
| D-181 | 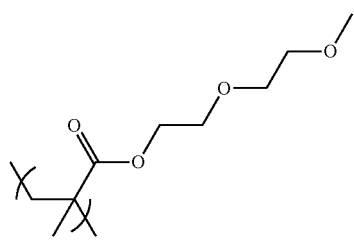 |

D-182
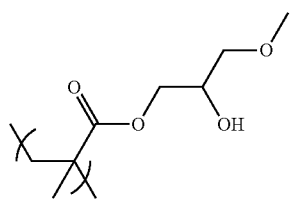
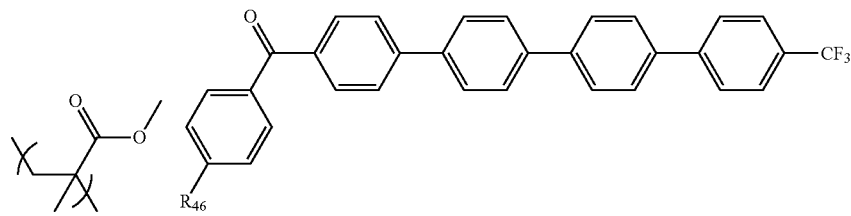
D-183
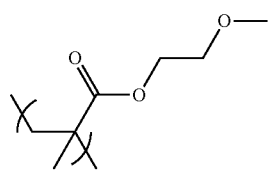
D-184
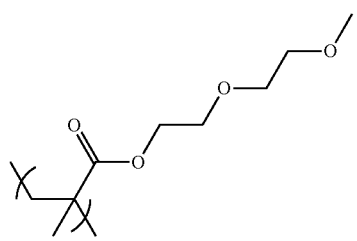
D-185
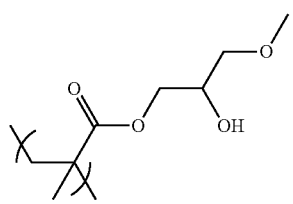
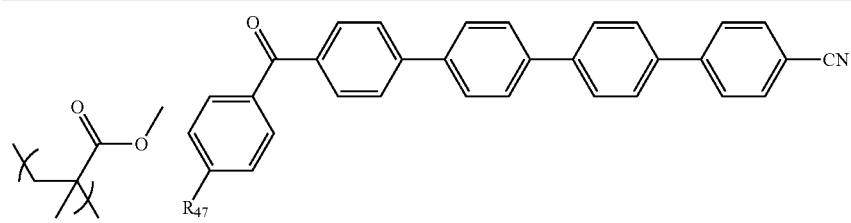
D-186
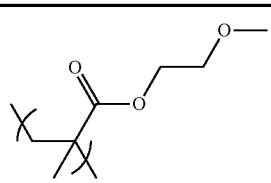

-continued
[Chem. 24]
D-187
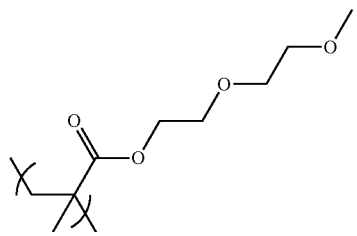
D-188
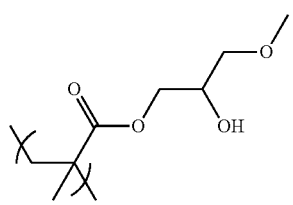
[Chem. 25]
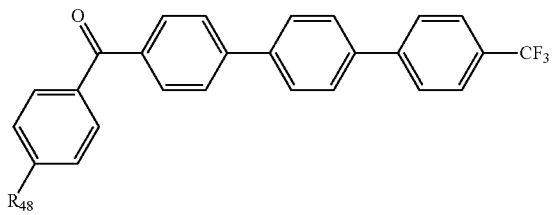
| $R_{48}$ |
|---|
| D-189 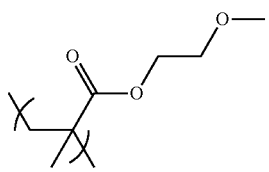 |
| D-190 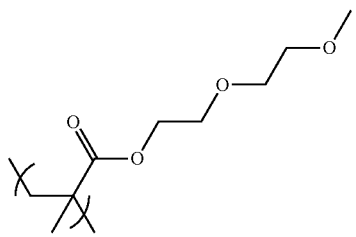 |
| D-191 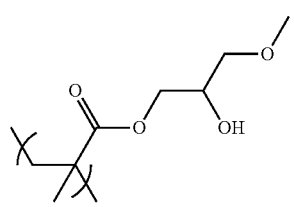 |

[Chem. 25]
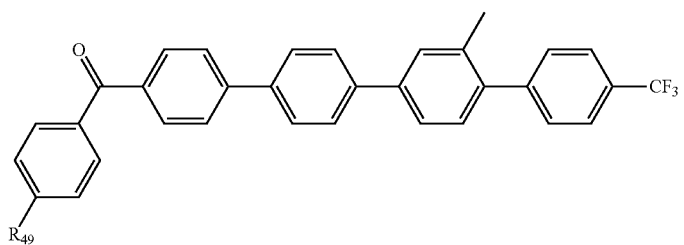
R49
| | R49 |
|---|---|
| D-192 | 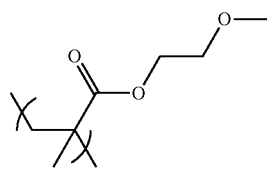 |
| D-193 | 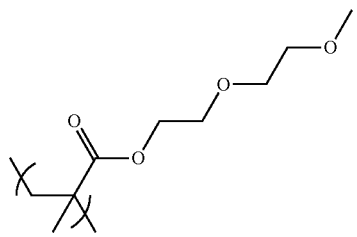 |
| D-194 | 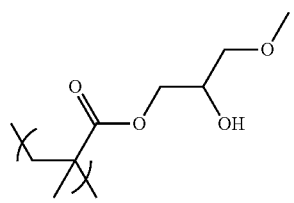 |
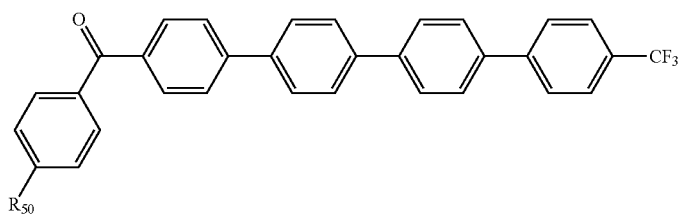
R50
| | R50 |
|---|---|
| D-195 | 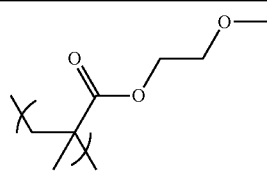 |
| D-196 | 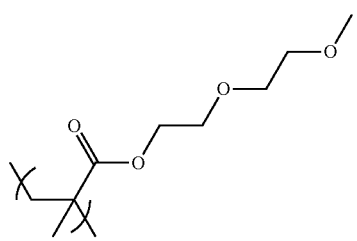 |

-continued
[Chem. 25]
D-197
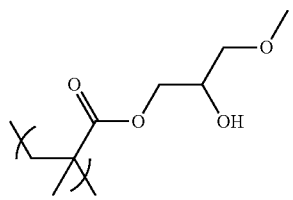
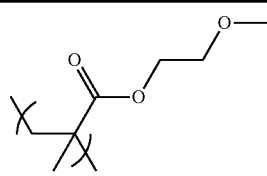
R$_{51}$
D-198
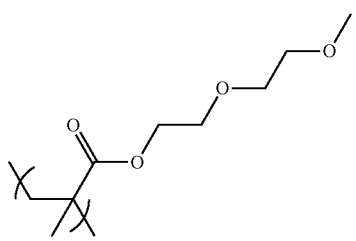
D-199
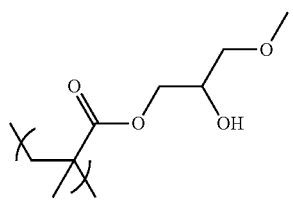
D-200
[Chem. 26]
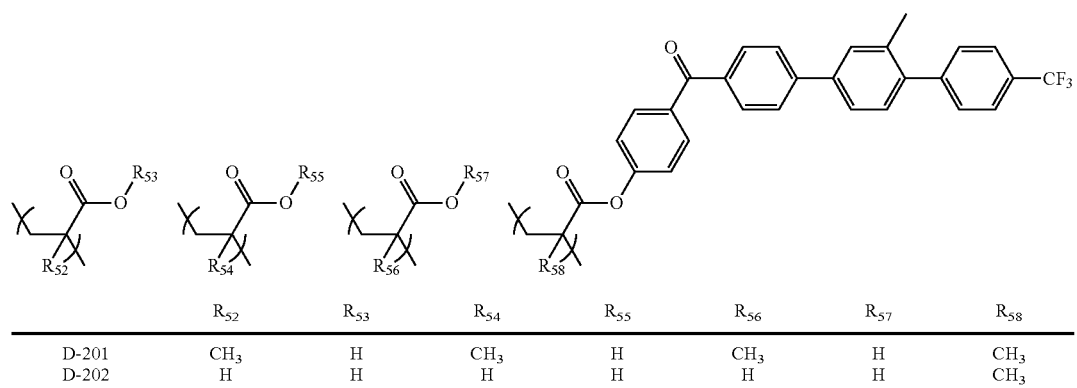
| | R$_{52}$ | R$_{53}$ | R$_{54}$ | R$_{55}$ | R$_{56}$ | R$_{57}$ | R$_{58}$ |
|---|---|---|---|---|---|---|---|
| D-201 | CH$_3$ | H | CH$_3$ | H | CH$_3$ | H | CH$_3$ |
| D-202 | H | H | H | H | H | H | CH$_3$ |

-continued

| | | | | | | |
|---|---|---|---|---|---|---|
| D-203 | CH₃ | H | CH₃ | H | CH₃ | H | H |
| D-204 | H | H | H | H | H | H | H |
| D-205 | CH₃ | H | CH₃ | H | H | H | CH₃ |
| D-206 | CH₃ | H | CH₃ | H | CH₃ | CH₃ | CH₃ |
| D-207 | CH₃ | H | CH₃ | H | H | CH₃ | CH₃ |
| D-208 | H | H | H | H | CH₃ | CH₃ | CH₃ |
| D-209 | H | H | H | H | H | CH₃ | CH₃ |
| D-210 | CH₃ | CH₃ | CH₃ | CH₃ | H | CH₃ | CH₃ |
| D-211 | CH₃ | H | CH₃ | H | H | H | H |
| D-212 | CH₃ | H | CH₃ | H | CH₃ | CH₃ | H |

[Chem. 27]

| | $R_{52}$ | $R_{53}$ | $R_{54}$ | $R_{55}$ | $R_{56}$ | $R_{57}$ | $R_{58}$ |
|---|---|---|---|---|---|---|---|
| D-213 | CH₃ | H | CH₃ | H | H | CH₃ | H |
| D-214 | H | H | H | H | CH₃ | CH₃ | H |
| D-215 | H | H | H | H | H | CH₃ | H |
| D-216 | CH₃ | CH₃ | CH₃ | CH₃ | H | CH₃ | H |
| D-217 | CH₃ | H | H | H | CH₃ | CH₃ | CH₃ |
| D-218 | CH₃ | H | H | H | H | CH₃ | CH₃ |
| D-219 | CH₃ | H | CH₃ | CH₃ | H | CH₃ | CH₃ |
| D-220 | H | H | CH₃ | CH₃ | H | CH₃ | CH₃ |
| D-221 | CH₃ | H | H | H | CH₃ | CH₃ | H |
| D-222 | CH₃ | H | H | H | H | CH₃ | H |
| D-223 | CH₃ | H | CH₃ | CH₃ | H | CH₃ | H |
| D-224 | H | H | CH₃ | CH₃ | H | CH₃ | H |

[Chem. 28]

| | $R_{59}$ | $R_{60}$ | $R_{61}$ | $R_{62}$ | $R_{63}$ | $R_{64}$ | $R_{65}$ |
|---|---|---|---|---|---|---|---|
| D-225 | CH₃ | H | CH₃ | H | CH₃ | H | CH₃ |
| D-226 | H | H | H | H | H | H | CH₃ |
| D-227 | CH₃ | H | CH₃ | H | CH₃ | H | H |
| D-228 | H | H | H | H | H | H | H |
| D-229 | CH₃ | H | CH₃ | H | H | H | CH₃ |
| D-230 | CH₃ | H | CH₃ | H | CH₃ | CH₃ | CH₃ |
| D-231 | CH₃ | H | CH₃ | H | H | CH₃ | CH₃ |
| D-232 | H | H | H | H | CH₃ | CH₃ | CH₃ |
| D-233 | H | H | H | H | H | CH₃ | CH₃ |
| D-234 | CH₃ | CH₃ | CH₃ | CH₃ | H | CH₃ | CH₃ |
| D-235 | CH₃ | H | CH₃ | H | H | H | H |
| D-236 | CH₃ | H | CH₃ | H | CH₃ | CH₃ | H |

[Chem. 29]

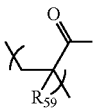

| | $R_{59}$ | $R_{60}$ | $R_{61}$ | $R_{62}$ | $R_{63}$ | $R_{64}$ | $R_{65}$ |
|---|---|---|---|---|---|---|---|
| D-237 | $CH_3$ | H | $CH_3$ | H | H | $CH_3$ | H |
| D-238 | H | H | H | H | $CH_3$ | $CH_3$ | H |
| D-239 | H | H | H | H | H | $CH_3$ | H |
| D-240 | $CH_3$ | $CH_3$ | $CH_3$ | $CH_3$ | H | $CH_3$ | H |
| D-241 | $CH_3$ | H | H | H | $CH_3$ | $CH_3$ | $CH_3$ |
| D-242 | $CH_3$ | H | H | H | H | $CH_3$ | $CH_3$ |
| D-243 | $CH_3$ | H | $CH_3$ | $CH_3$ | H | $CH_3$ | $CH_3$ |
| D-244 | H | H | $CH_3$ | $CH_3$ | H | $CH_3$ | $CH_3$ |
| D-245 | $CH_3$ | H | H | H | $CH_3$ | $CH_3$ | H |
| D-246 | $CH_3$ | H | H | H | H | $CH_3$ | H |
| D-247 | $CH_3$ | H | $CH_3$ | $CH_3$ | H | $CH_3$ | H |
| D-248 | H | H | $CH_3$ | $CH_3$ | H | $CH_3$ | H |

[Chem. 30]

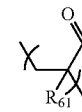

| | $R_{66}$ | $R_{67}$ | $R_{68}$ | $R_{69}$ | $R_{70}$ | $R_{71}$ | $R_{72}$ |
|---|---|---|---|---|---|---|---|
| D-249 | $CH_3$ | H | $CH_3$ | H | $CH_3$ | H | $CH_3$ |
| D-250 | H | H | H | H | H | H | $CH_3$ |
| D-251 | $CH_3$ | H | $CH_3$ | H | $CH_3$ | H | H |
| D-252 | H | H | H | H | H | H | H |
| D-253 | $CH_3$ | H | $CH_3$ | H | H | H | $CH_3$ |
| D-254 | $CH_3$ | H | $CH_3$ | H | $CH_3$ | $CH_3$ | $CH_3$ |
| D-255 | $CH_3$ | H | $CH_3$ | H | H | $CH_3$ | $CH_3$ |
| D-256 | H | H | H | H | $CH_3$ | $CH_3$ | $CH_3$ |
| D-257 | H | H | H | H | H | $CH_3$ | $CH_3$ |
| D-258 | $CH_3$ | $CH_3$ | $CH_3$ | $CH_3$ | H | $CH_3$ | $CH_3$ |
| D-259 | $CH_3$ | H | $CH_3$ | H | H | H | H |
| D-260 | $CH_3$ | H | $CH_3$ | H | $CH_3$ | $CH_3$ | H |

[Chem. 31]

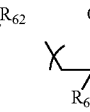

| | $R_{66}$ | $R_{67}$ | $R_{68}$ | $R_{69}$ | $R_{70}$ | $R_{71}$ | $R_{72}$ |
|---|---|---|---|---|---|---|---|
| D-261 | $CH_3$ | H | $CH_3$ | H | H | $CH_3$ | H |
| D-262 | H | H | H | H | $CH_3$ | $CH_3$ | H |

| | | | | | | | |
|---|---|---|---|---|---|---|---|
| D-263 | H | H | H | H | H | CH₃ | H |
| D-264 | CH₃ | CH₃ | CH₃ | CH₃ | H | CH₃ | H |
| D-265 | CH₃ | H | H | H | CH₃ | CH₃ | CH₃ |
| D-266 | CH₃ | H | H | H | H | CH₃ | CH₃ |
| D-267 | CH₃ | H | CH₃ | CH₃ | H | CH₃ | CH₃ |
| D-268 | H | H | CH₃ | CH₃ | H | CH₃ | CH₃ |
| D-269 | CH₃ | H | H | H | CH₃ | CH₃ | H |
| D-270 | CH₃ | H | H | H | H | CH₃ | H |
| D-271 | CH₃ | H | CH₃ | CH₃ | H | CH₃ | H |
| D-272 | H | H | CH₃ | CH₃ | H | CH₃ | H |
[Chem. 32]
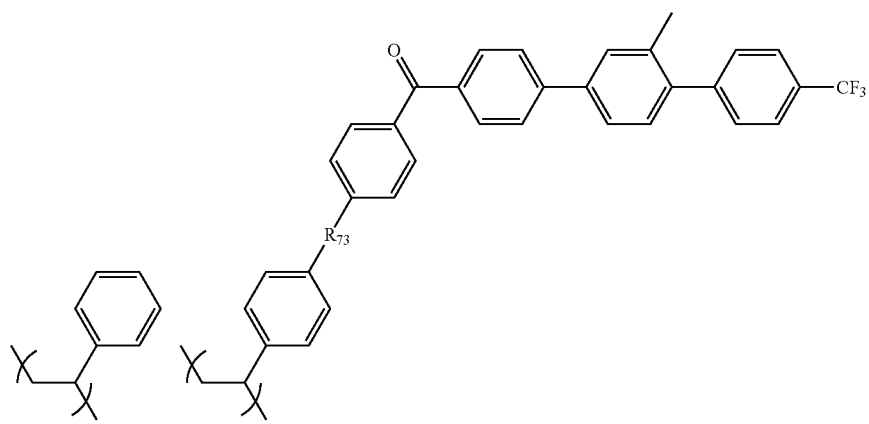
R₇₃
D-273
D-274
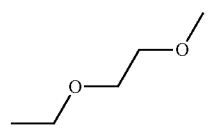
D-275
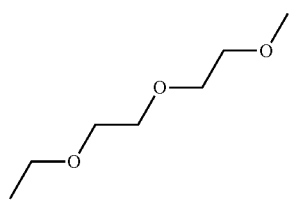

[Chem. 32]
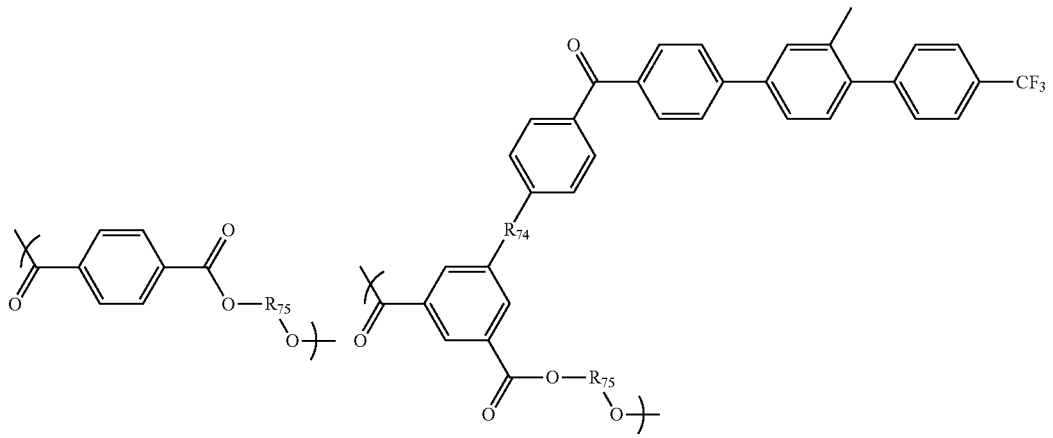
| | R74 | R75 |
|---|---|---|
| D-276 | 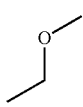 | 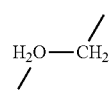 |
| D-277 | 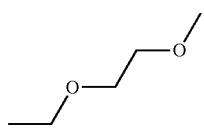 | 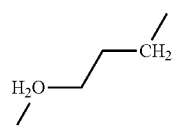 |
| D-278 | 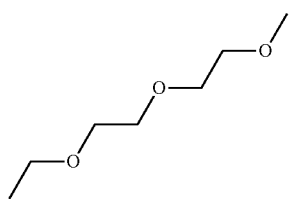 | 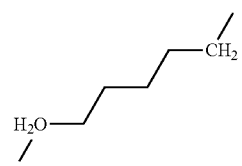 |
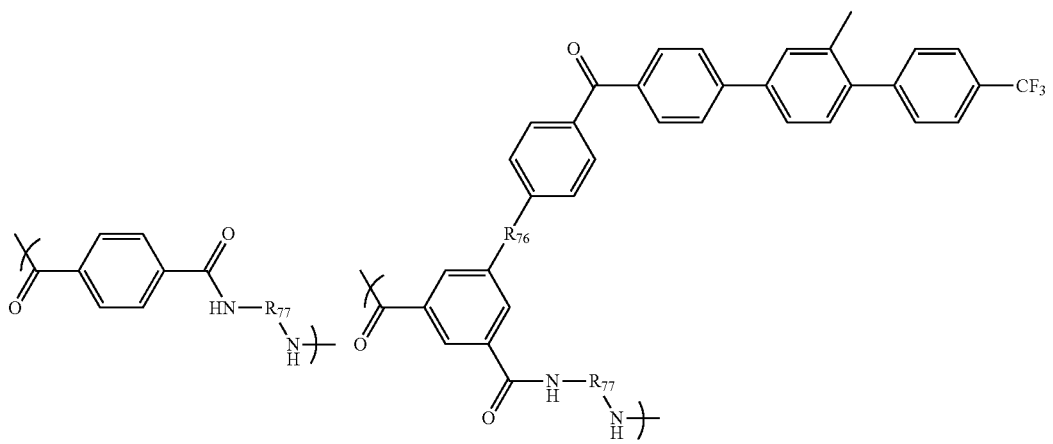
| | R76 | R77 |
|---|---|---|
| D-279 | 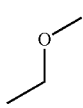 | 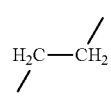 |

| | |
|---|---|
| D-280 | 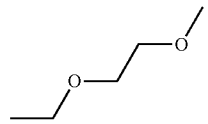 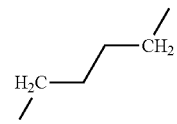 |
| D-281 | 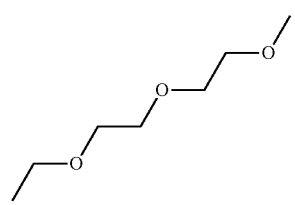 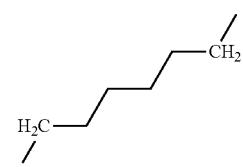 |
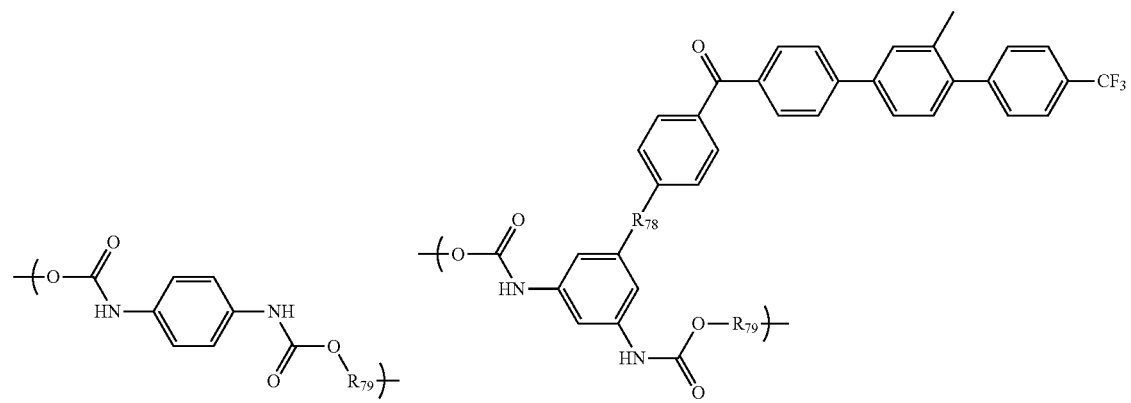
| R$_{78}$ | R$_{79}$ |
|---|---|
| D-282 | 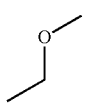 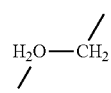 |
| D-283 | 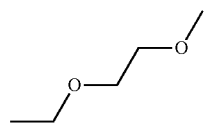 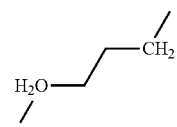 |
| D-284 | 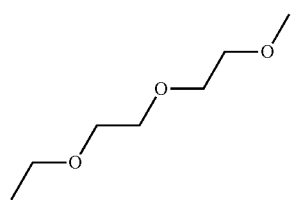 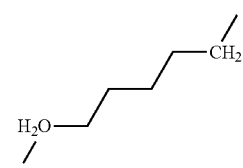 |

[Chem. 33]
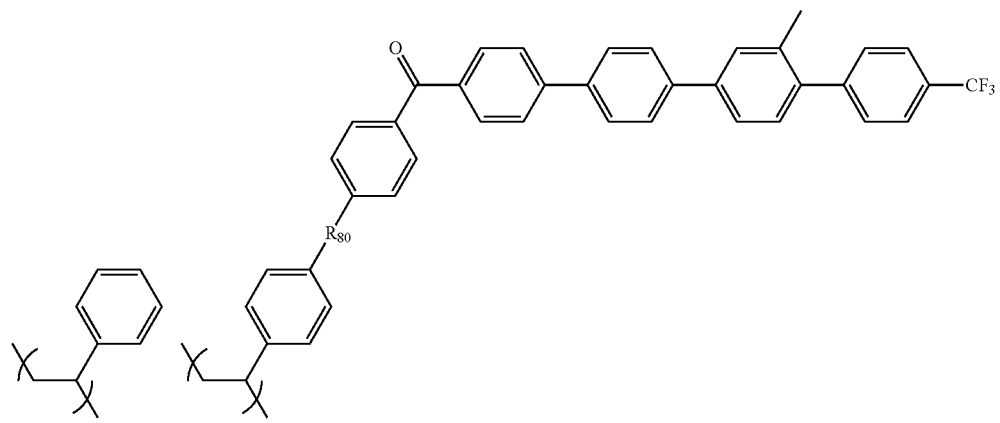
| | $R_{80}$ |
|---|---|
| D-285 |  |
| D-286 | 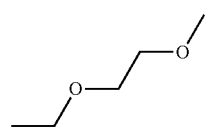 |
| D-287 | 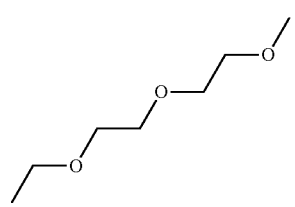 |
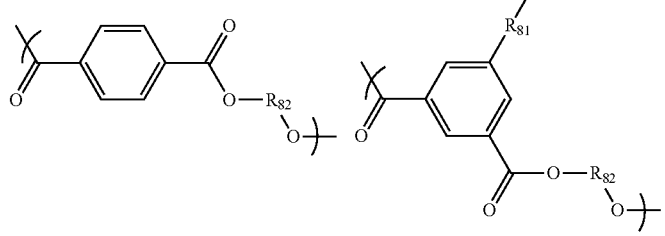
| | $R_{81}$ | $R_{82}$ |
|---|---|---|
| D-288 |  | 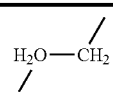 |
| D-289 | 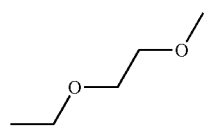 | 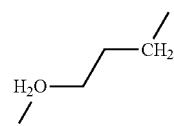 |

[Chem. 33]
| | $R_{83}$ | $R_{84}$ |
|---|---|---|
| D-290 |  | 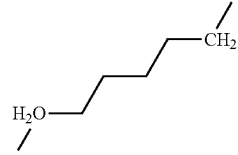 |
| D-291 |  | 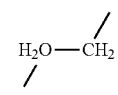 |
| D-292 | 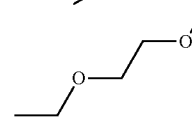 | 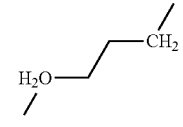 |
| D-293 | 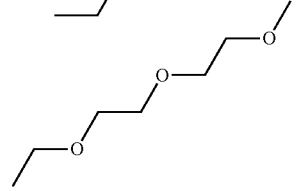 | 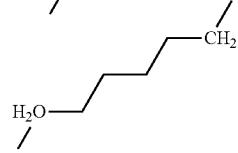 |
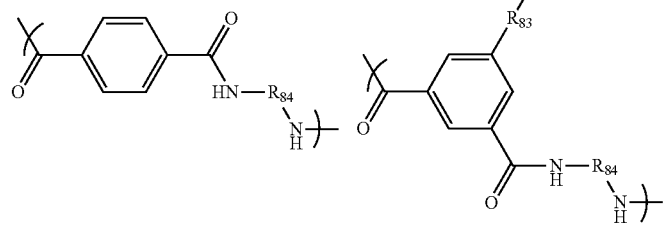
| | $R_{85}$ | $R_{86}$ |
|---|---|---|
| D-294 | 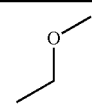 | 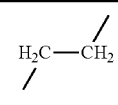 |
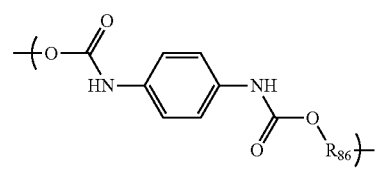

[Chem. 33]
D-295 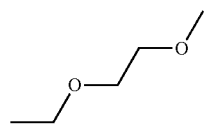 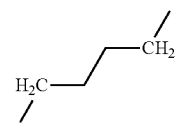
D-296 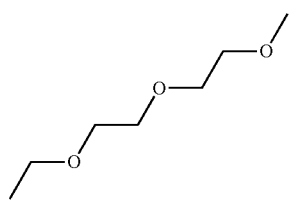 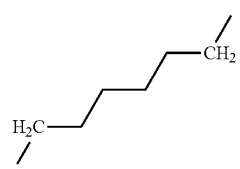
[Chem. 34]
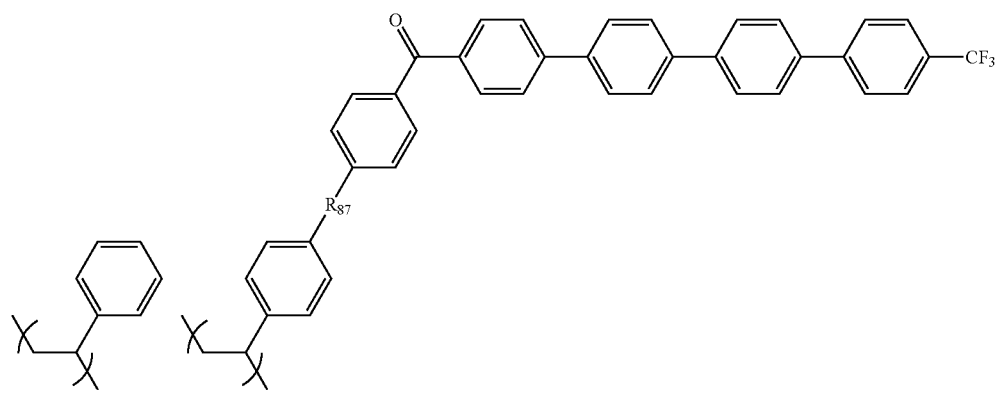
R_{87}
D-297 
D-298 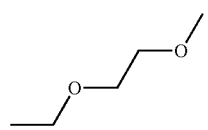
D-299 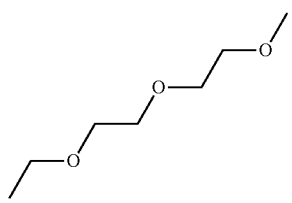

[Chem. 34]
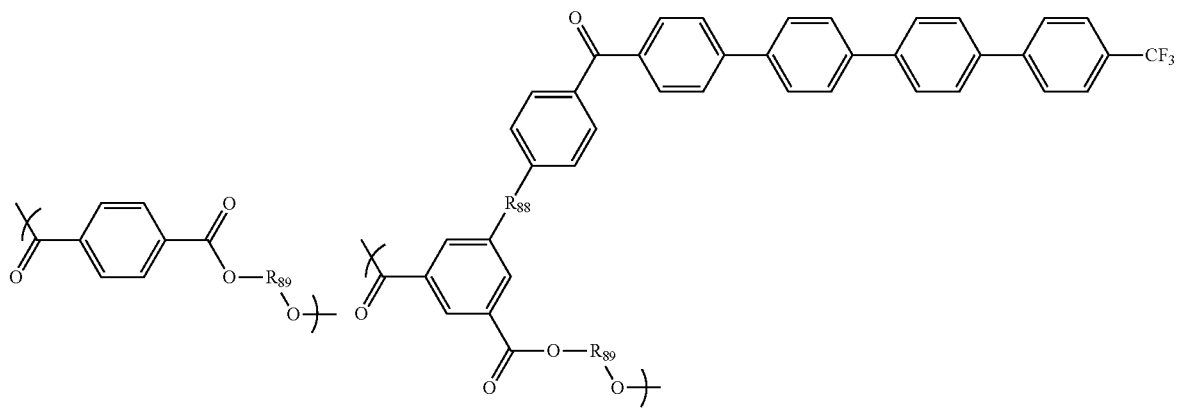
| | R88 | R89 |
|---|---|---|
| D-300 | 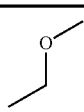 | 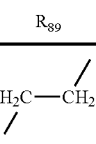 |
| D-301 | 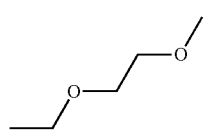 | 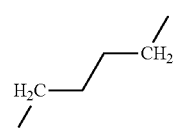 |
| D-302 | 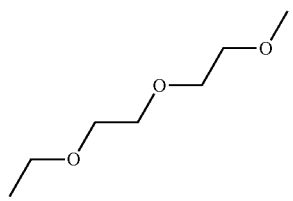 | 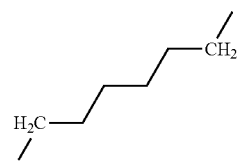 |
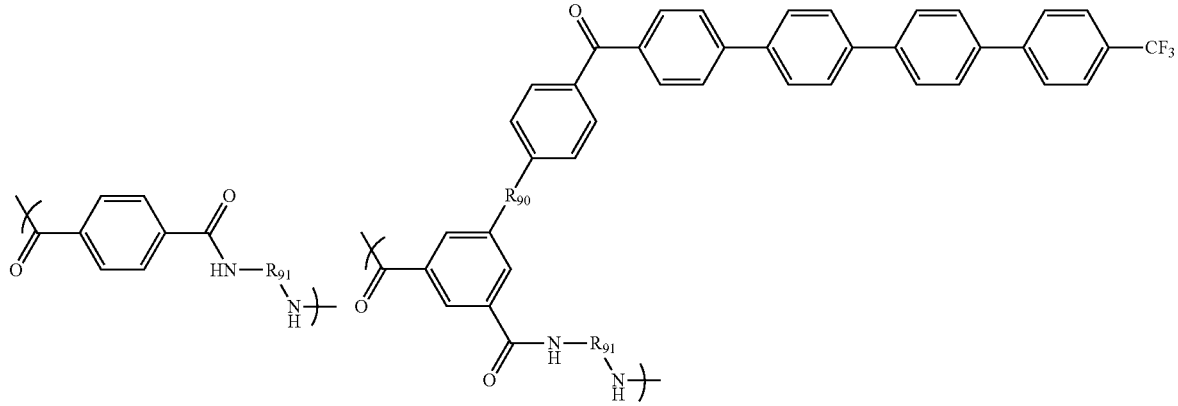
| | R90 | R91 |
|---|---|---|
| D-303 | 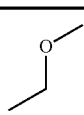 | 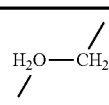 |
| D-304 | 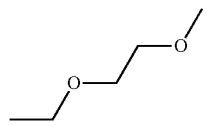 | 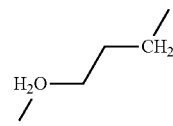 |

-continued
[Chem. 34]
| | $R_{92}$ | $R_{93}$ |
|---|---|---|
| D-305 | 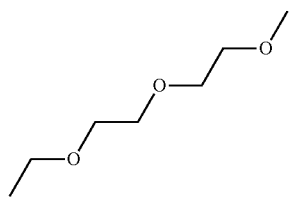 | 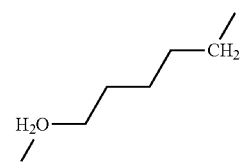 |
| | 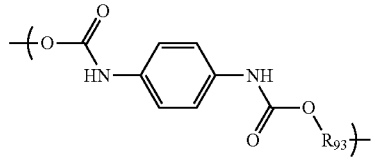 | 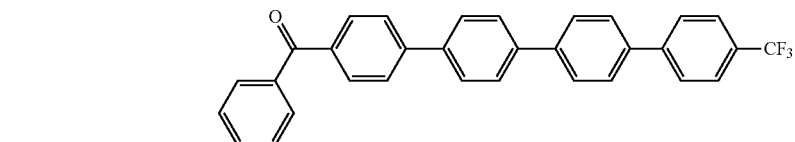 |
| D-306 | 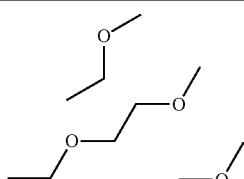 | 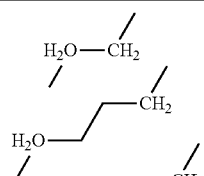 |
| D-307 | 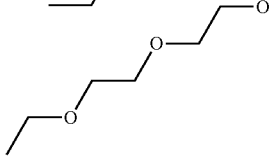 | |
| D-308 | 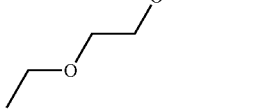 | |
[Chem. 35]
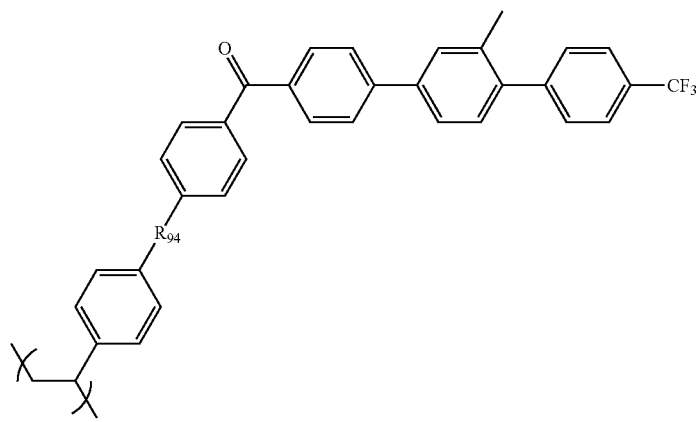
| | $R_{94}$ |
|---|---|
| D-309 |  |

-continued
[Chem. 35]
D-310
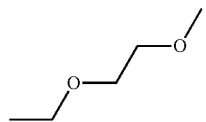
D-311
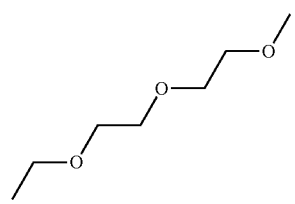
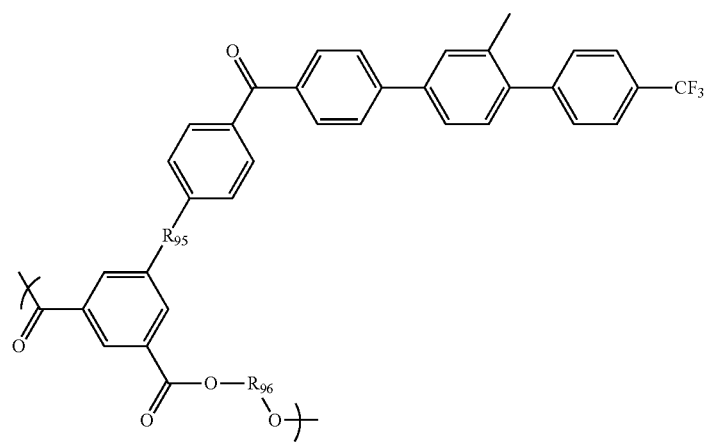
| | $R_{95}$ | $R_{96}$ |
|---|---|---|
| D-312 |  | 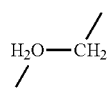 |
| D-313 | 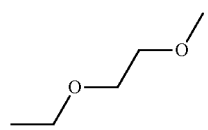 | 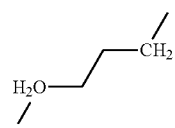 |
| D-314 | 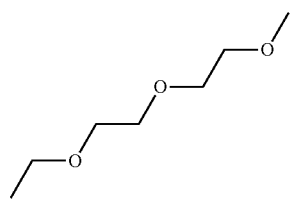 | 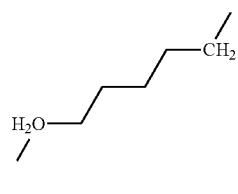 |

[Chem. 35]
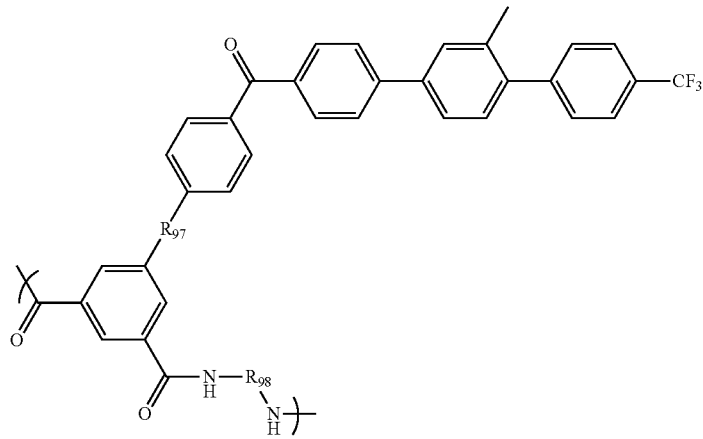
| | $R_{97}$ | $R_{98}$ |
|---|---|---|
| D-315 |  | |
| D-316 |  | |
| D-317 | 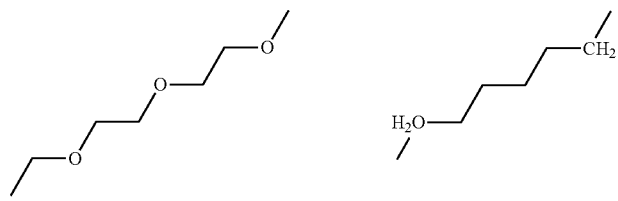 | |
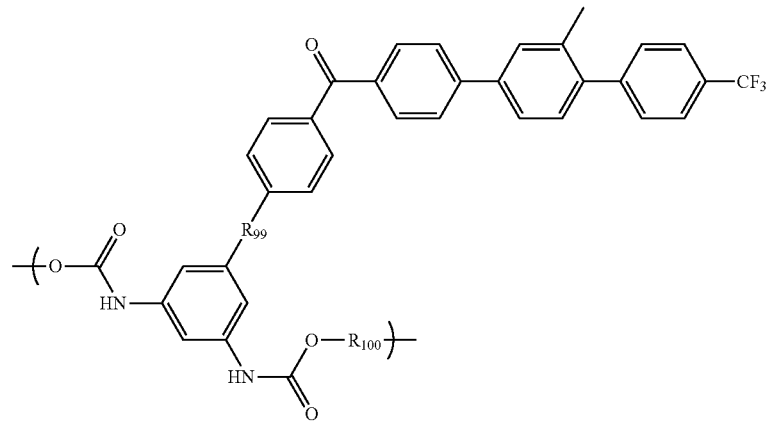
| | $R_{99}$ | $R_{100}$ |
|---|---|---|
| D-318 |  | |

-continued
[Chem. 35]
D-319 
D-320 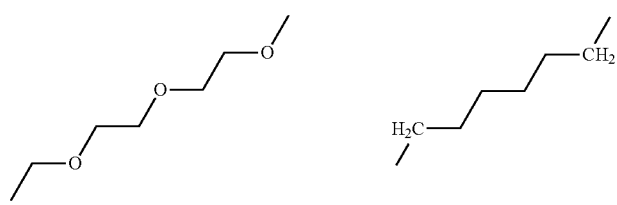
[Chem. 36]
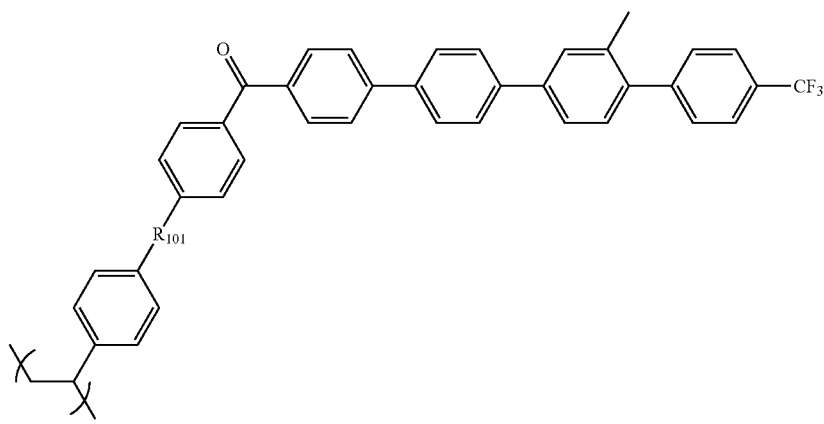
| | $R_{101}$ |
|---|---|
| D-321 |  |
| D-322 | 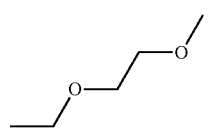 |
| D-323 | 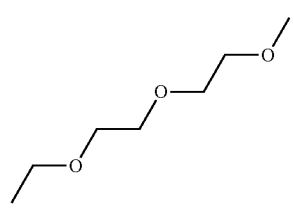 |

[Chem. 36]
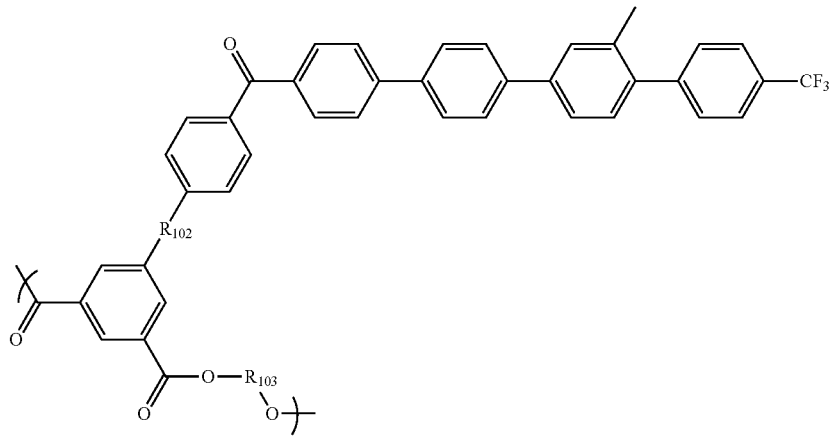
| | $R_{102}$ | $R_{103}$ |
|---|---|---|
| D-324 |  | 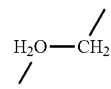 |
| D-325 | 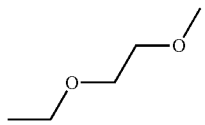 | 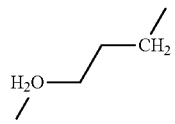 |
| D-326 | 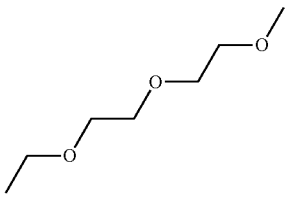 | 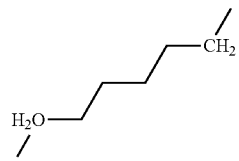 |
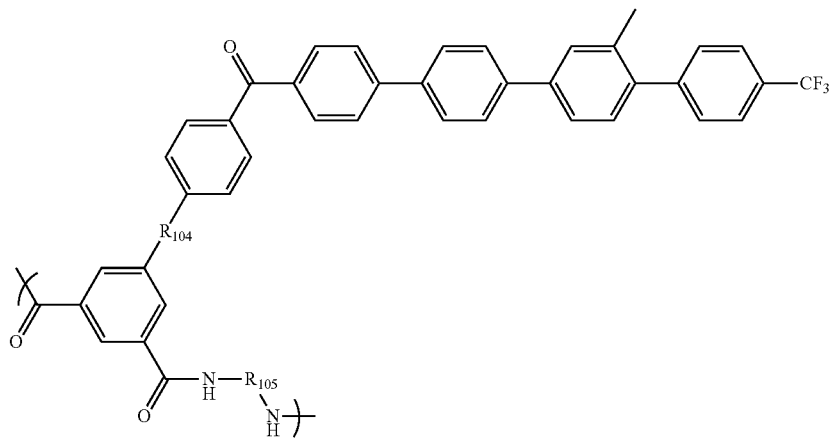
| | $R_{104}$ | $R_{105}$ |
|---|---|---|
| D-327 |  | 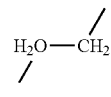 |

-continued
[Chem. 36]
| | | |
|---|---|---|
| D-328 | 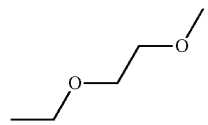 | 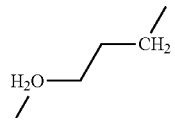 |
| D-329 | 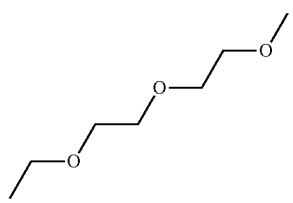 | 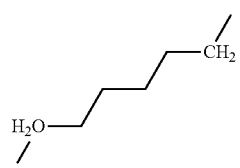 |
| | $R_{106}$ | $R_{107}$ |
|---|---|---|
| D-330 |  | 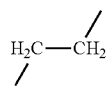 |
| D-331 | 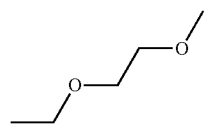 | 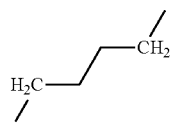 |
| D-332 | 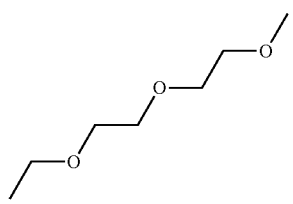 | 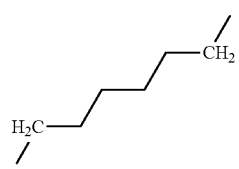 |

[Chem. 37]
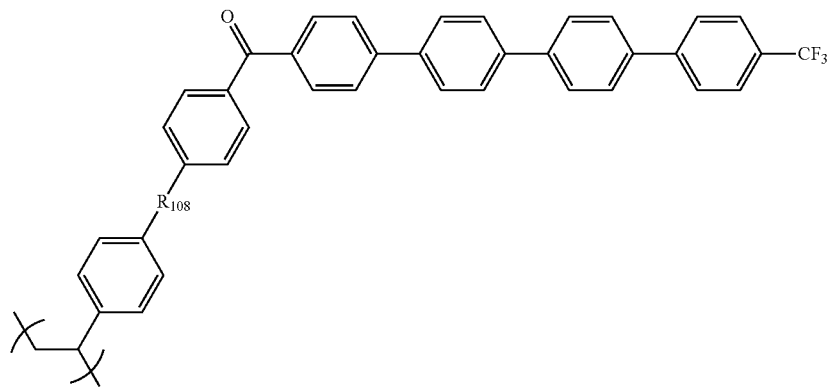
| | $R_{108}$ |
|---|---|
| D-333 | 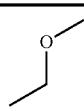 |
| D-334 | 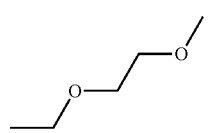 |
| D-335 | 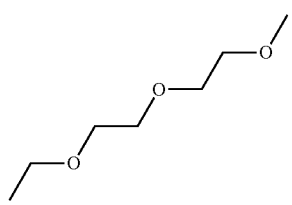 |
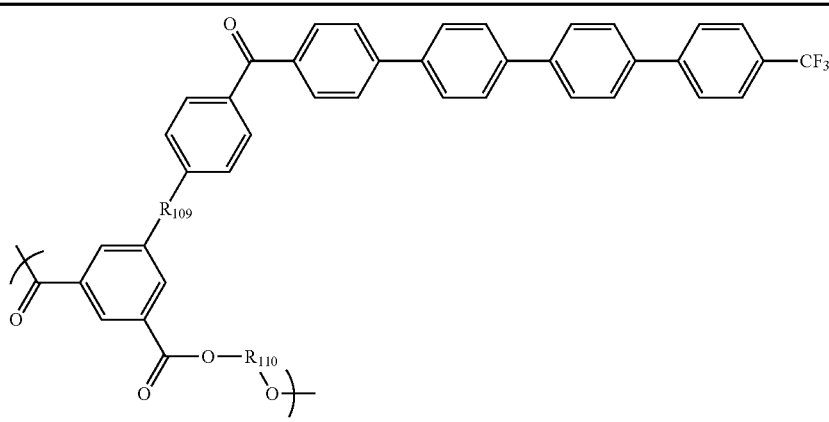
| | $R_{109}$ | $R_{110}$ |
|---|---|---|
| D-336 | 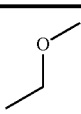 | 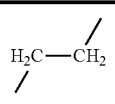 |
| D-337 | 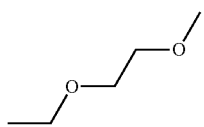 | 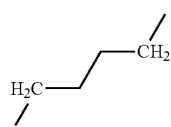 |

-continued
[Chem. 37]
D-338
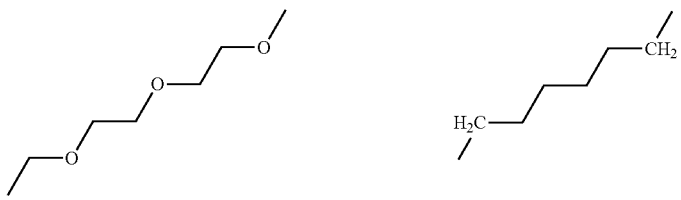
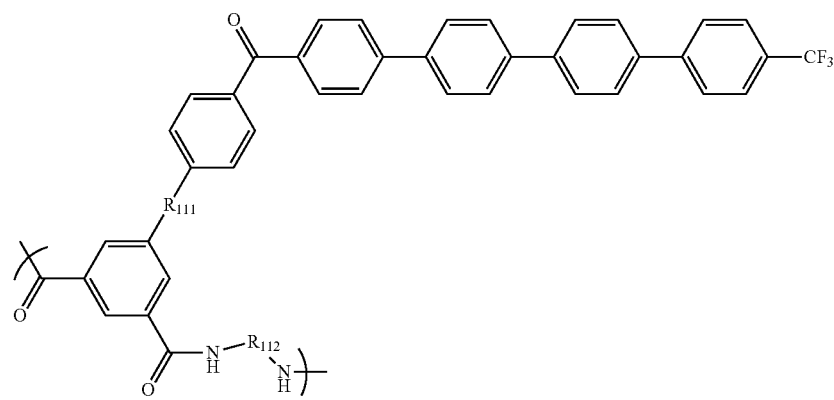
| $R_{111}$ | $R_{112}$ |
|---|---|
D-339
D-340
D-341
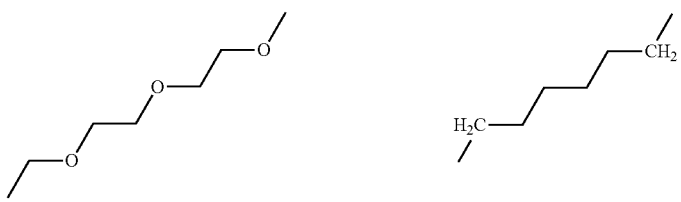

[Chem. 37]
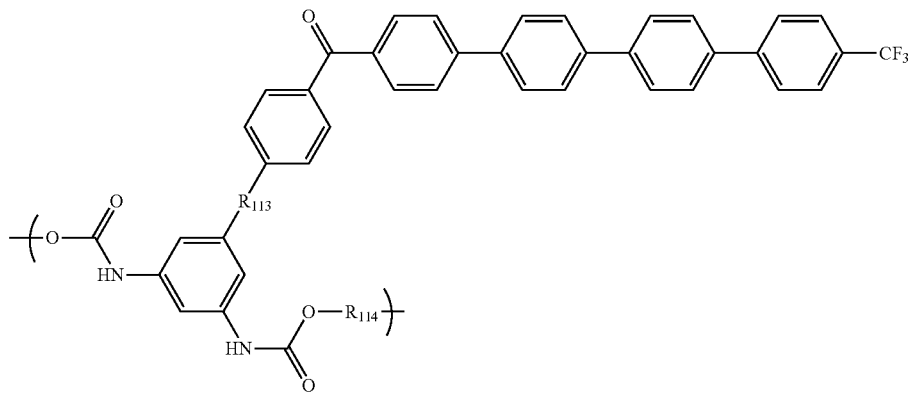
| | R₁₁₃ | R₁₁₄ |
|---|---|---|
| D-342 |  | 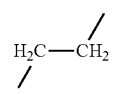 |
| D-343 | | |
| D-344 | 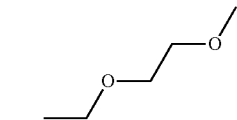 | 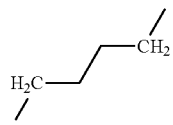 |

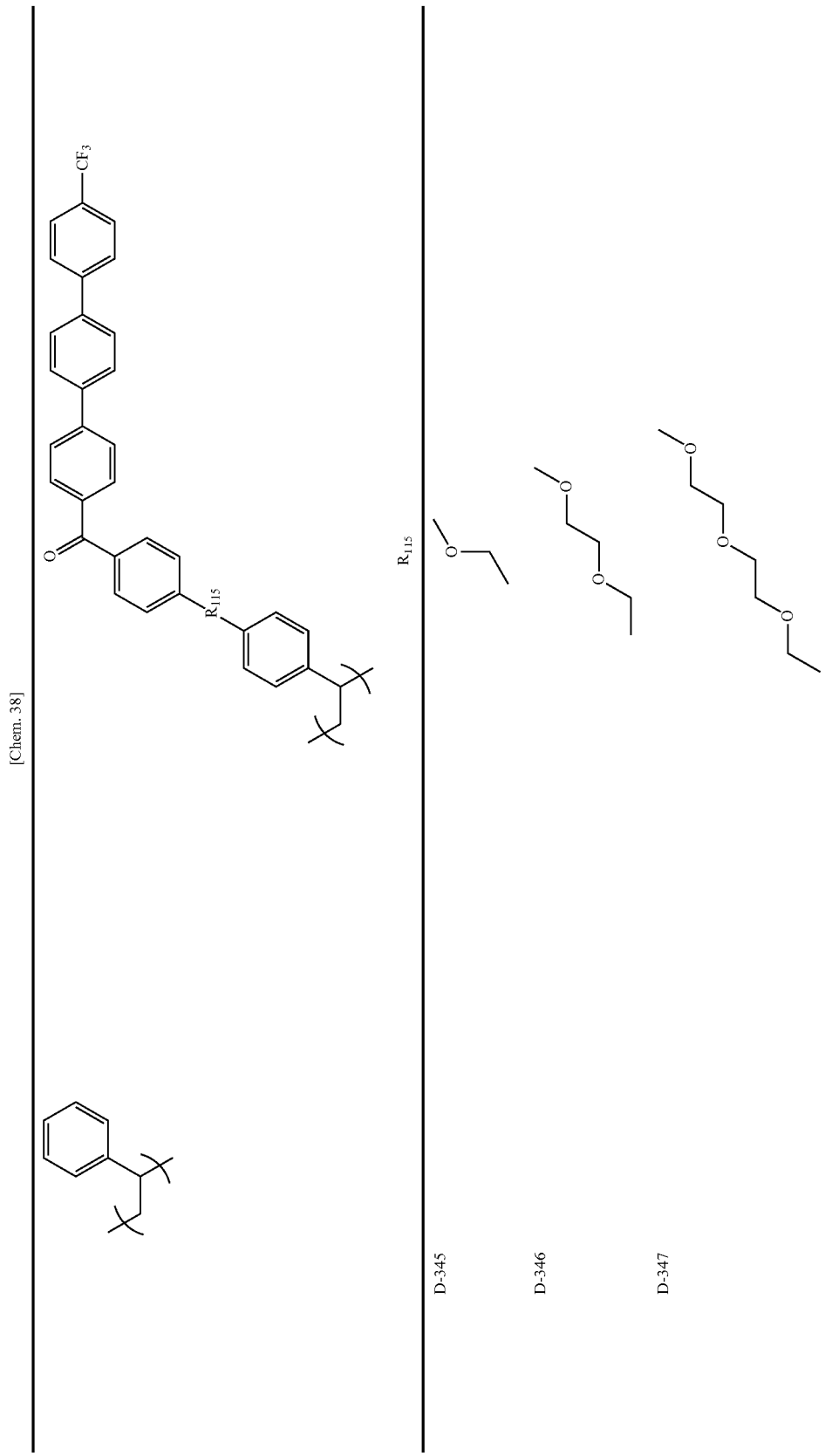

-continued
[Chem. 38]
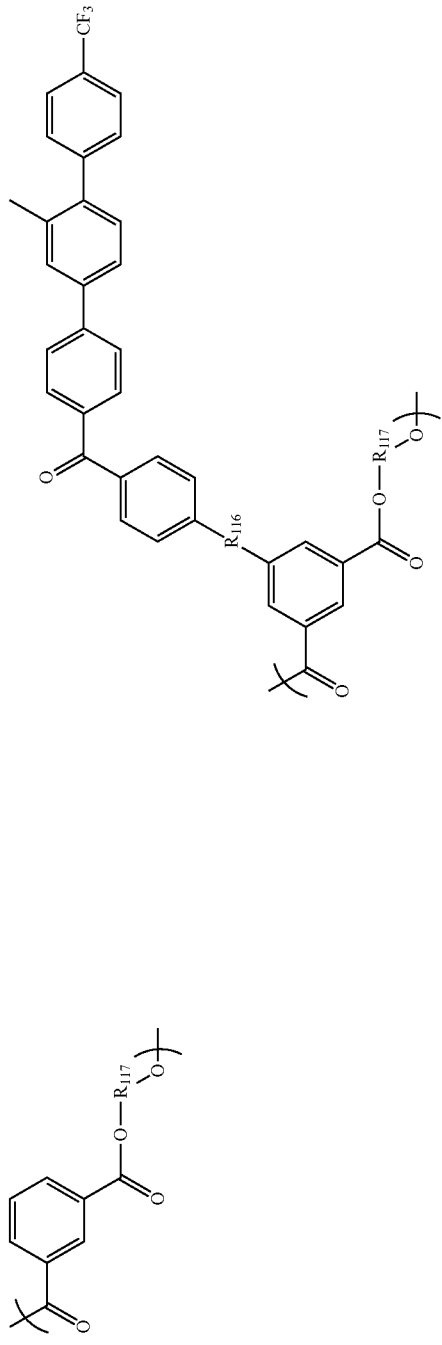
| | $R_{116}$ | $R_{117}$ |
|---|---|---|
| D-348 |  | 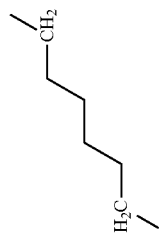 |
| D-349 | 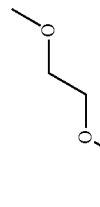 | |
| D-350 | 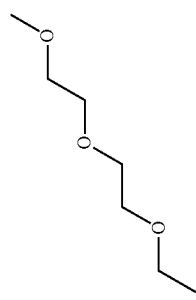 | |

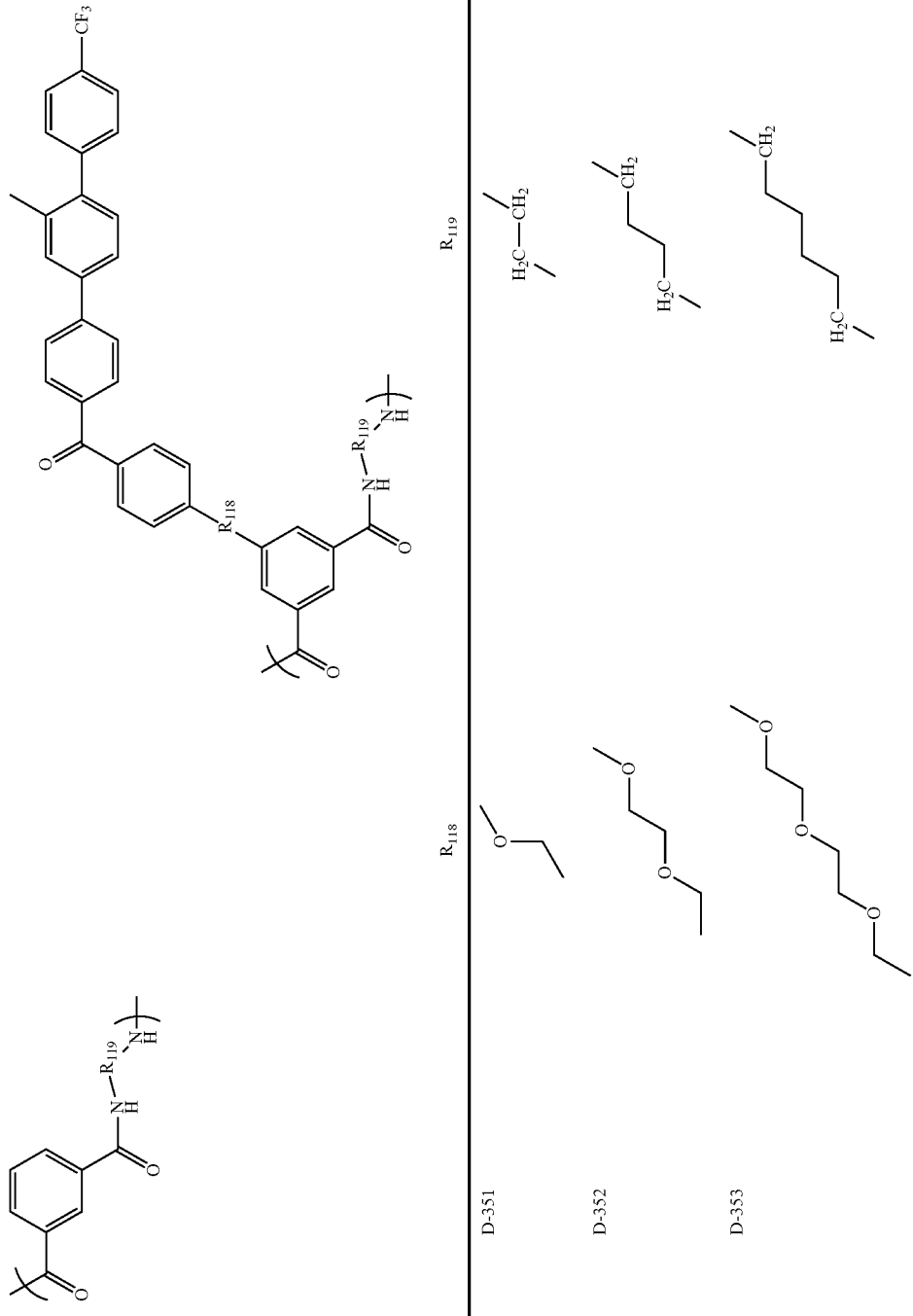

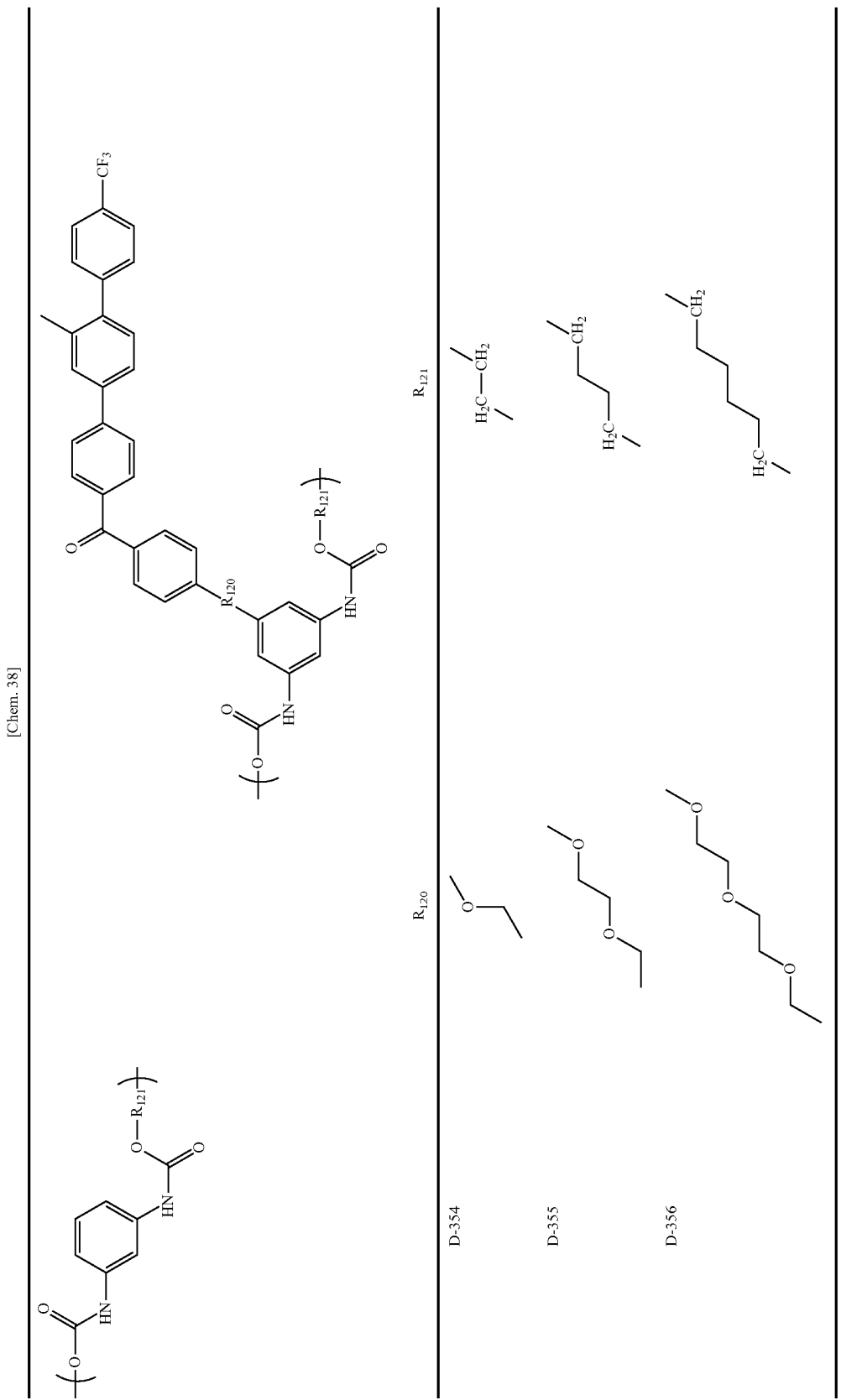

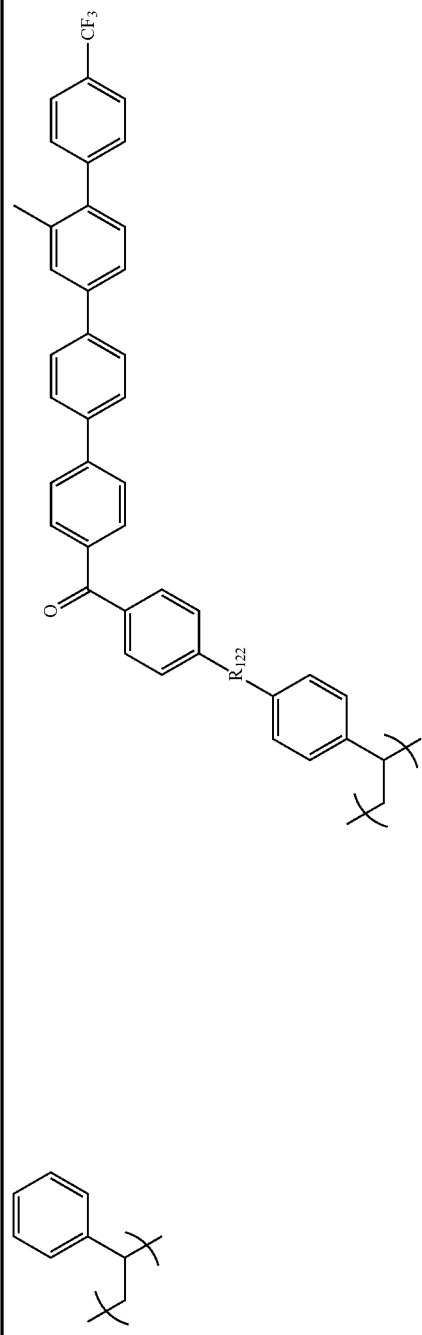

-continued
[Chem. 39]
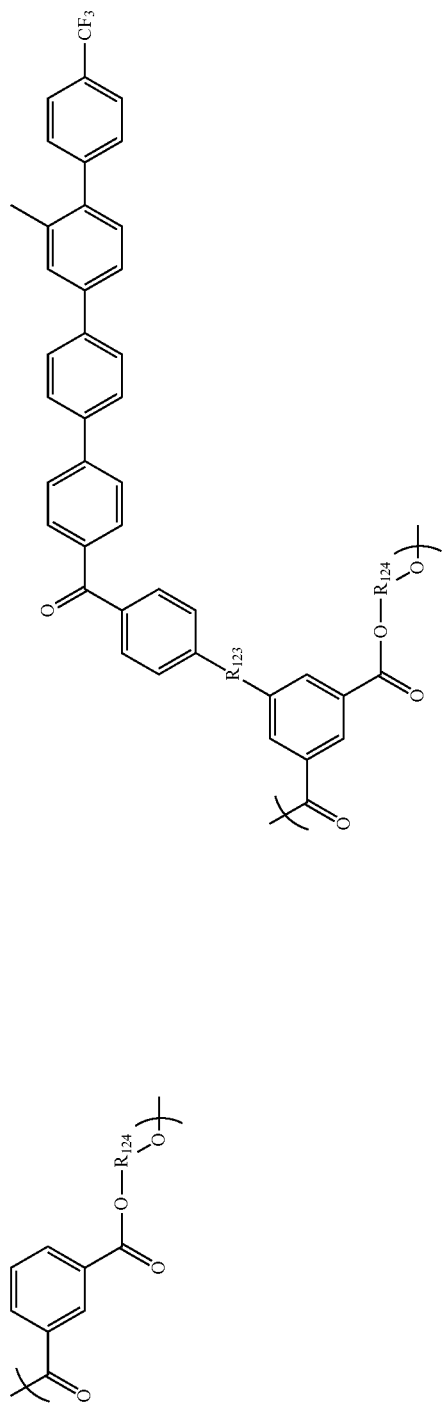
| | $R_{123}$ | $R_{124}$ |
|---|---|---|
| D-360 |  | 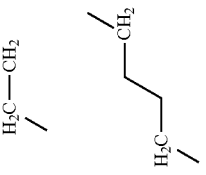 |
| D-361 | | |
| D-362 |  | 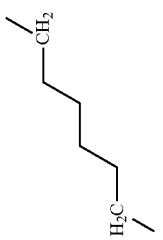 |

-continued
[Chem. 39]
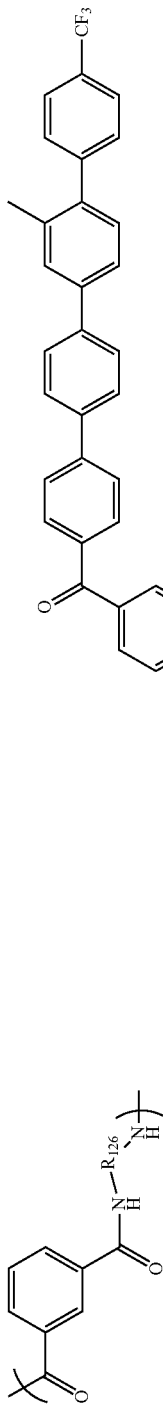
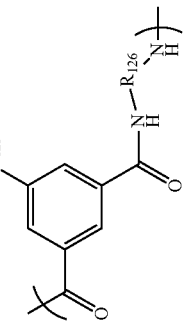
| | R_{125} | R_{126} |
|---|---|---|
| D-363 | 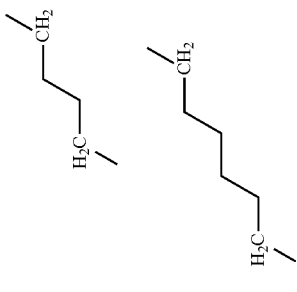 | 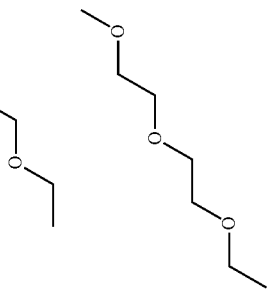 |
| D-364 | | |
| D-365 | | |

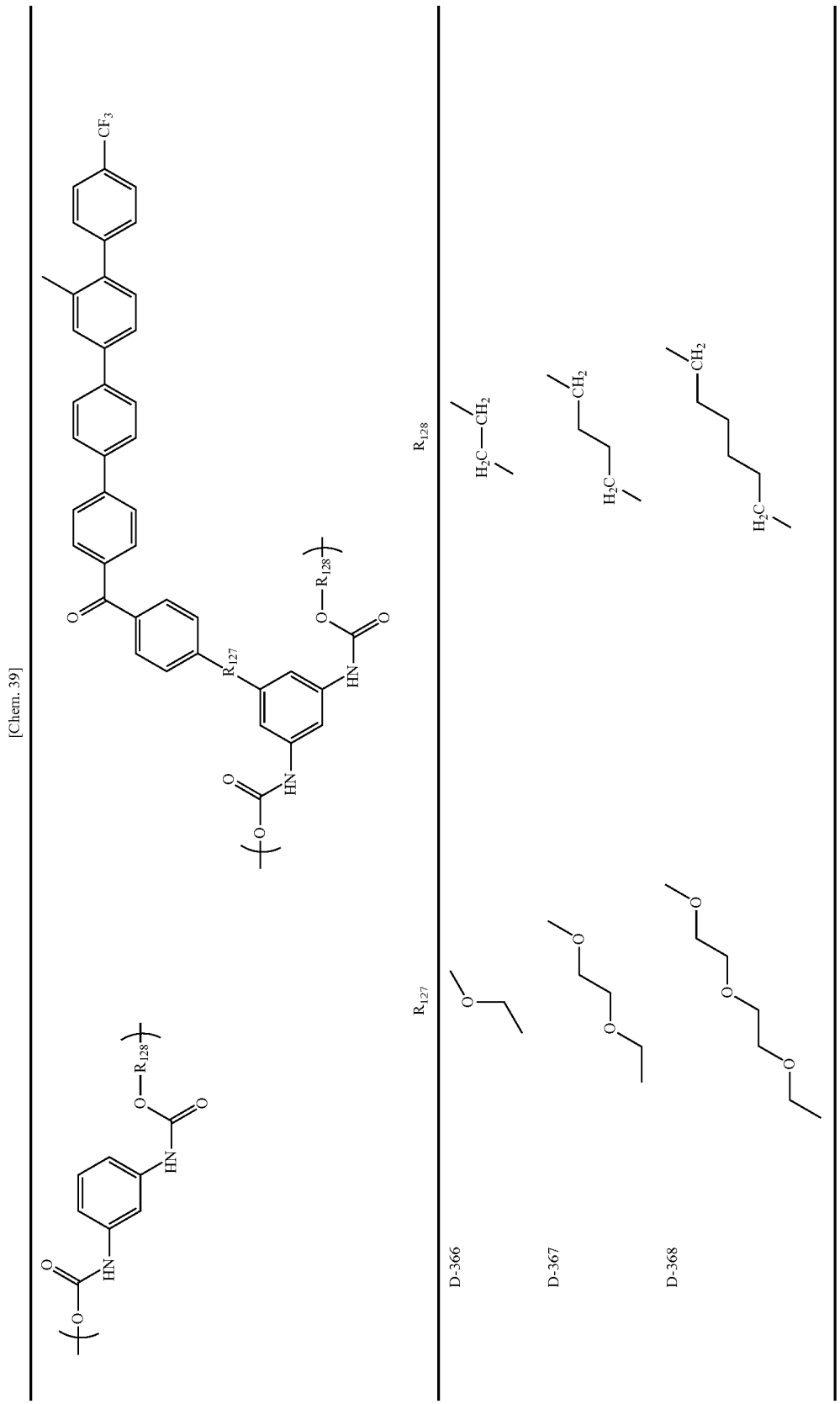

[Chem. 40]
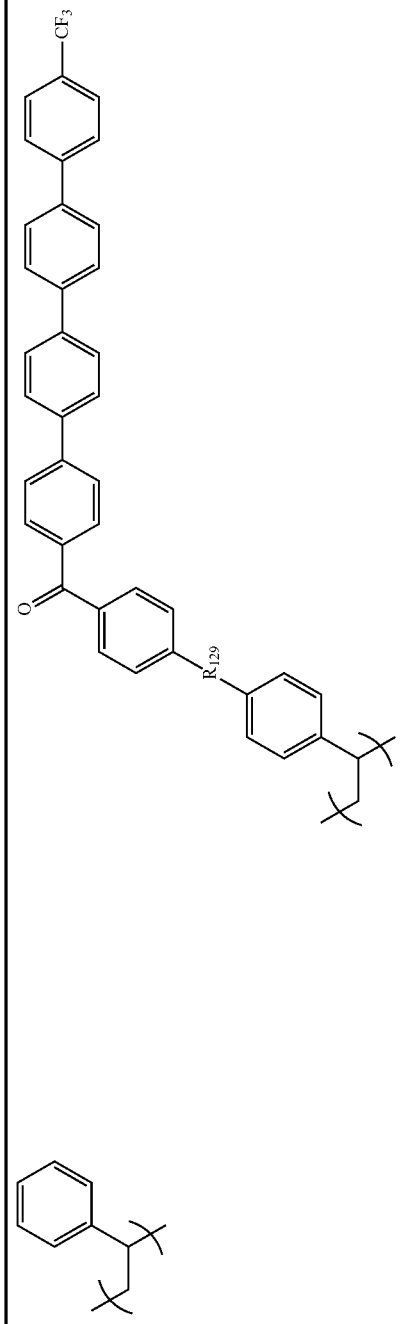
| | $R_{129}$ |
|---|---|
| D-369 | 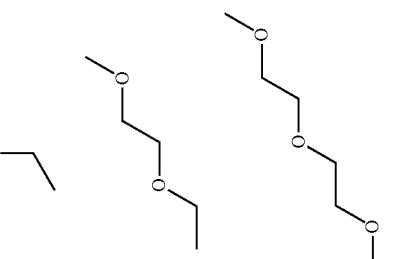 |
| D-370 | |
| D-371 | |

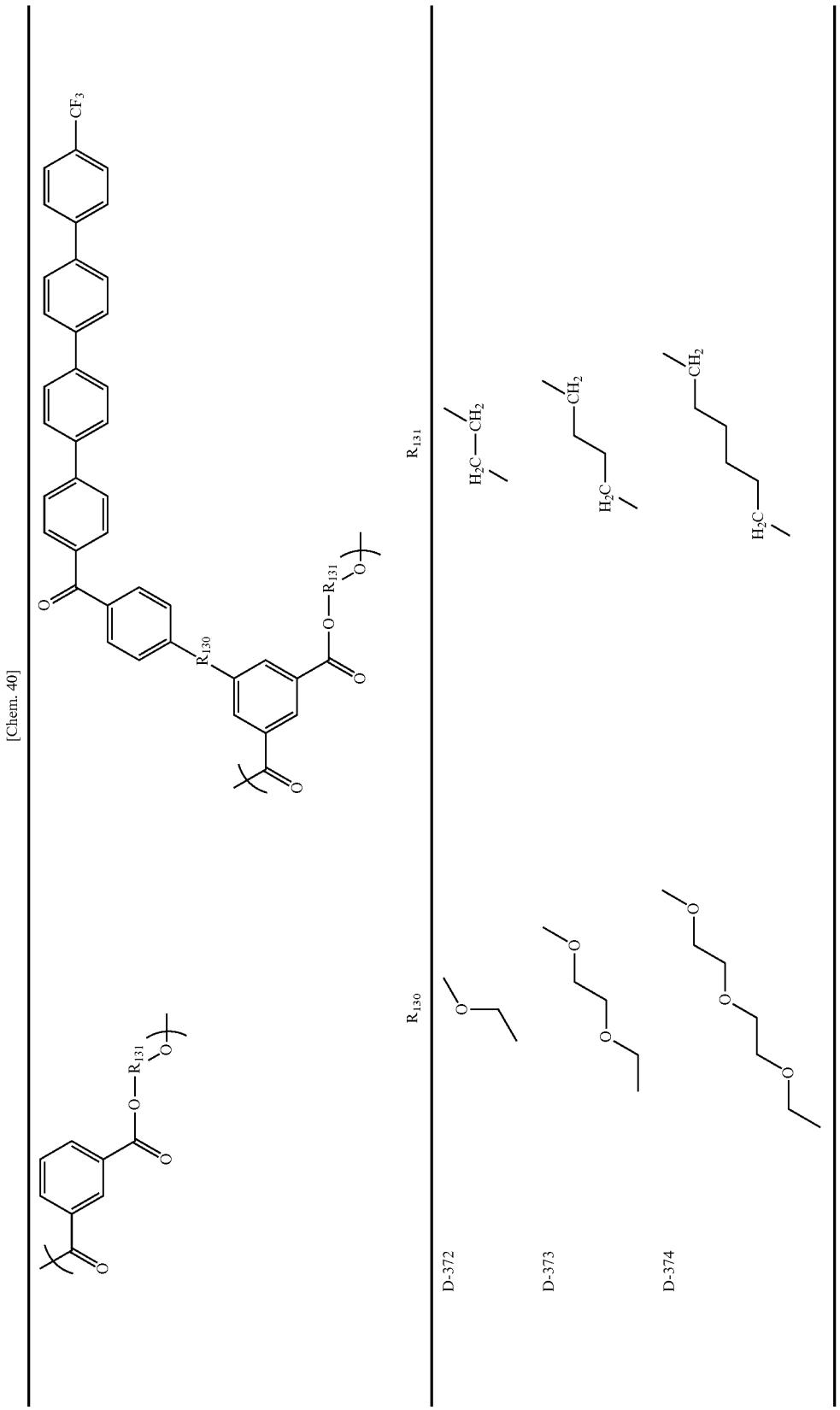

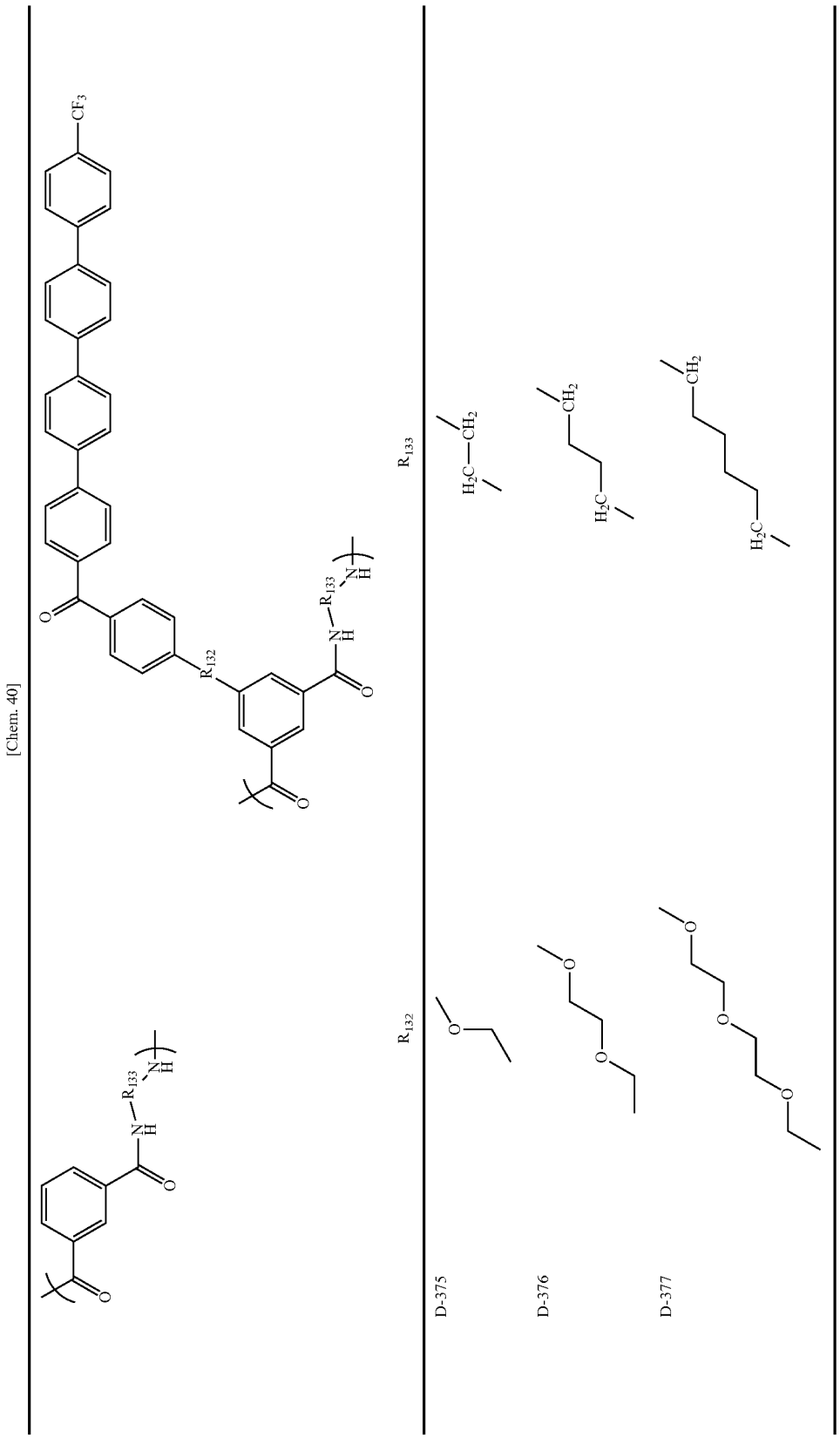

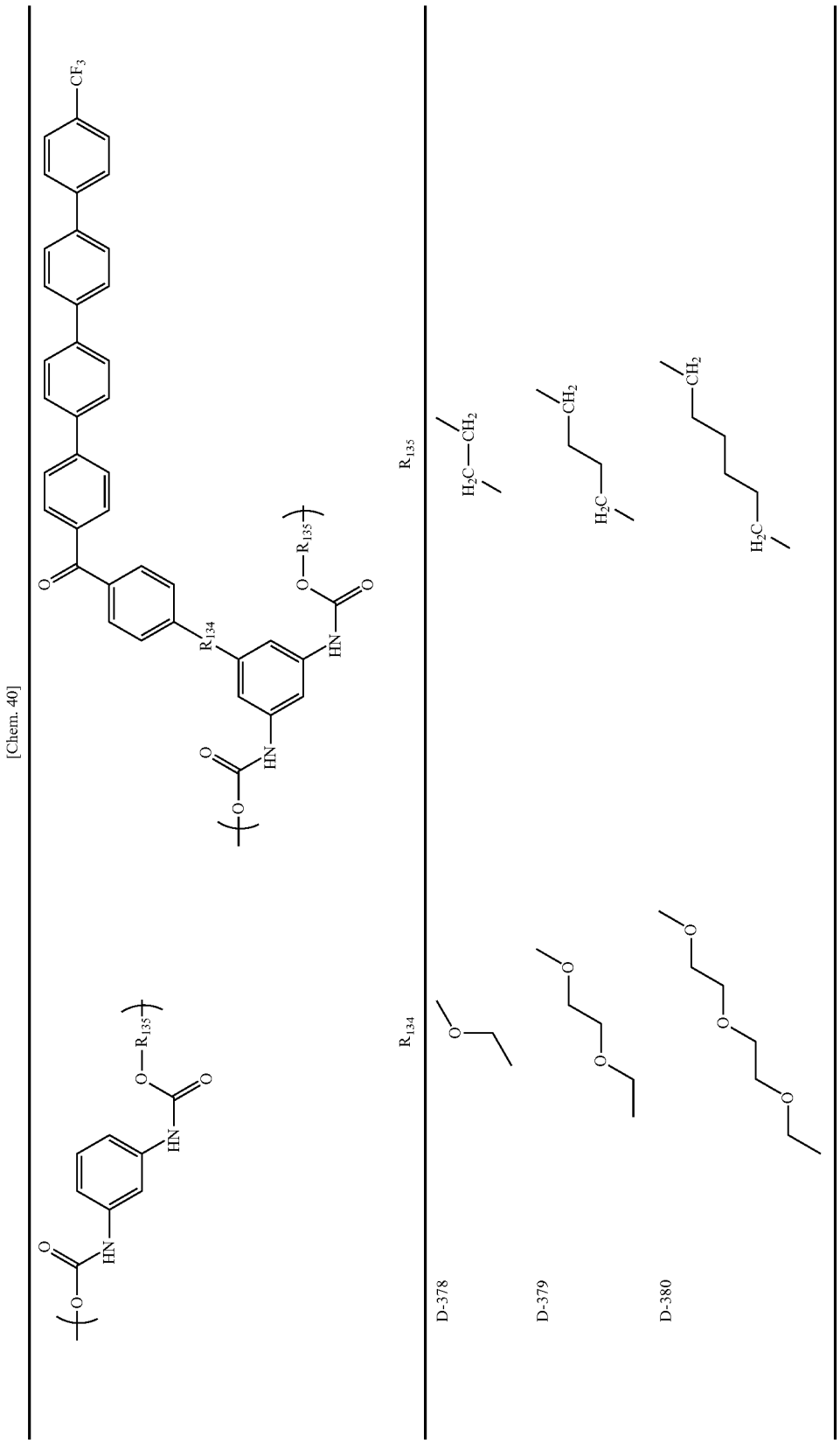

[Chem. 41]
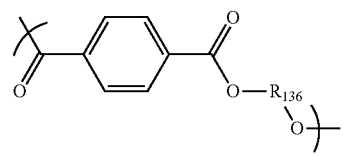
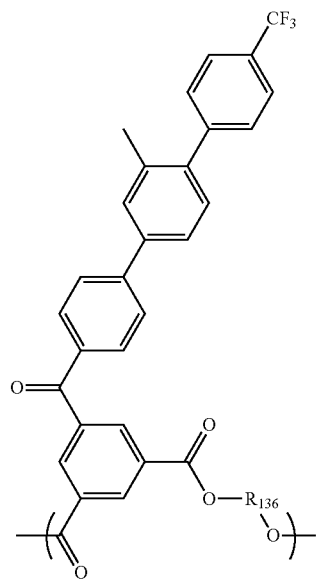
| | $R_{136}$ |
|---|---|
| D-381 | 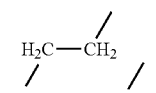 |
| D-382 | 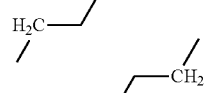 |
| D-383 |  |
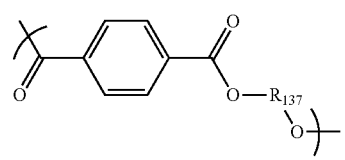
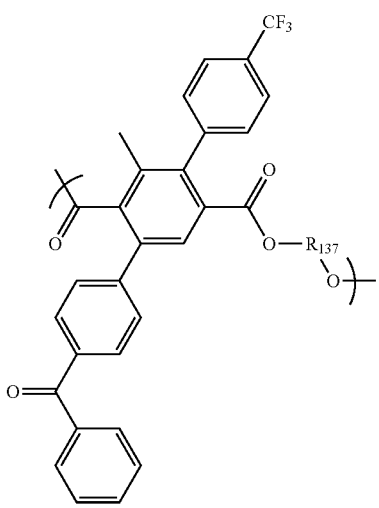
| | $R_{137}$ |
|---|---|
| D-384 | 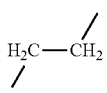 |

-continued
[Chem. 41]
D-385
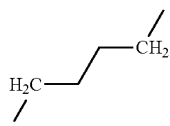
D-386
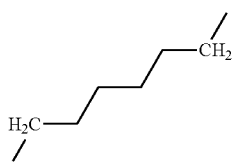
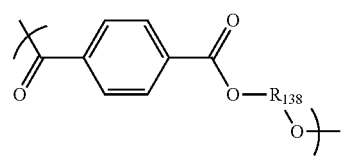  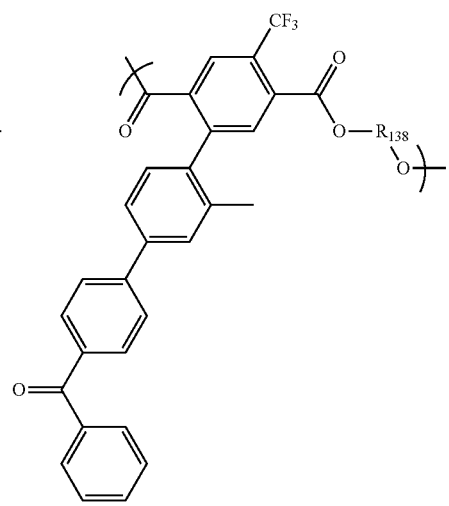
R₁₃₈
D-387
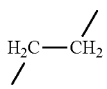
D-388
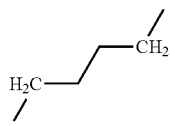
D-389
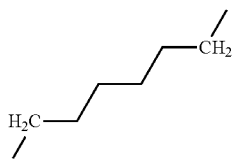

-continued
[Chem. 41]
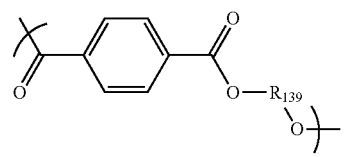
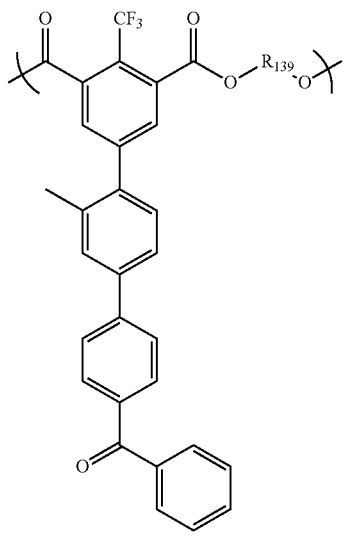
$R_{139}$
D-390
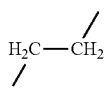
D-391
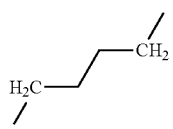
D-392
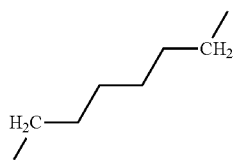

[Chem. 42]
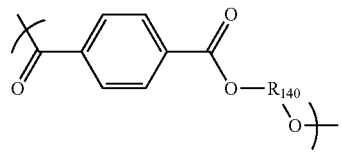
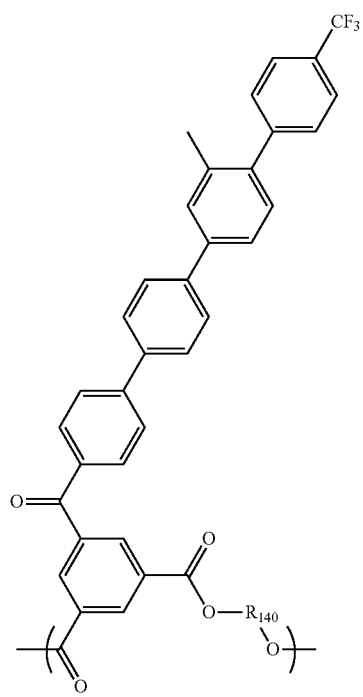
$R_{140}$
D-393
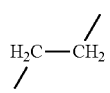
D-394
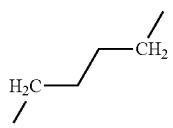
D-395
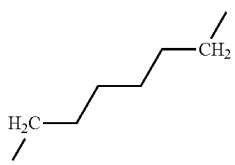

-continued
[Chem. 42]
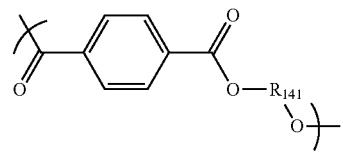
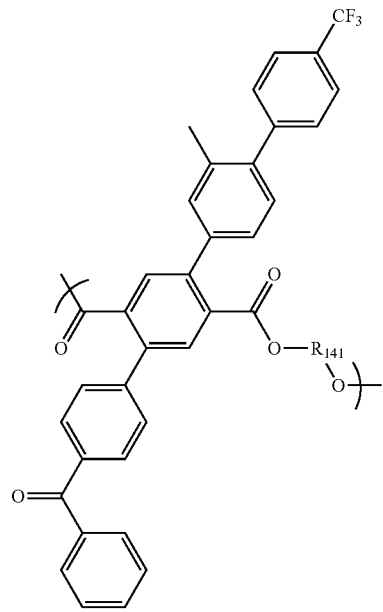
$R_{141}$
D-396
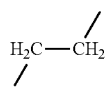
D-397
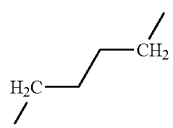
D-398
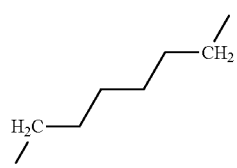

-continued
[Chem. 42]
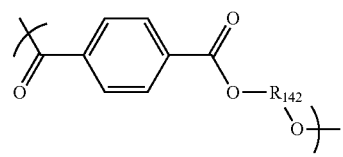
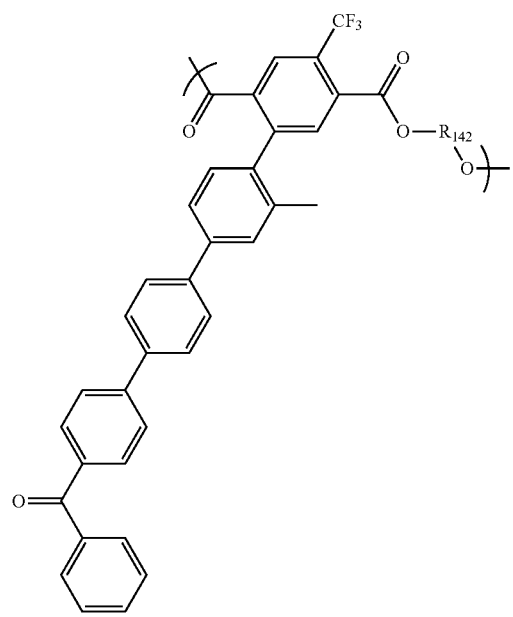
D-399
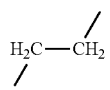
D-400
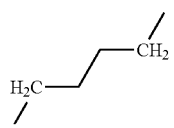
D-401
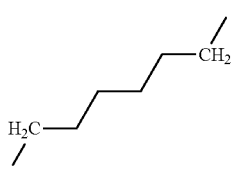

-continued
[Chem. 42]
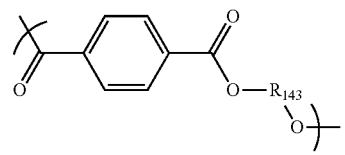
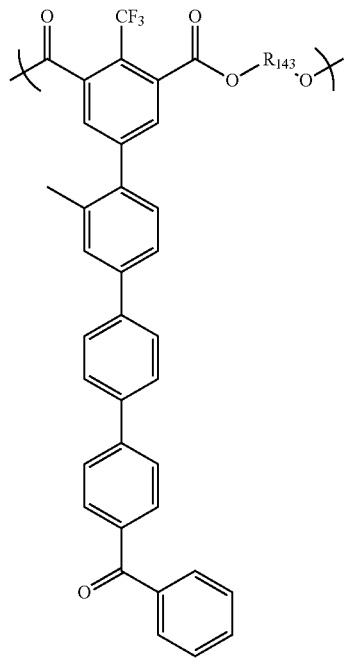
$R_{143}$
D-402
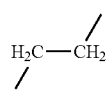
D-403
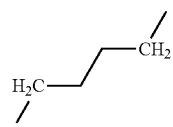
D-404
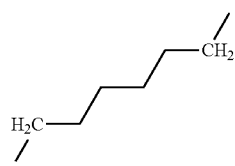

[Chem. 43]
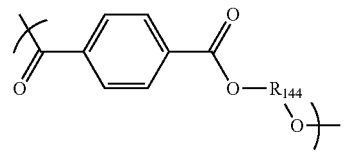
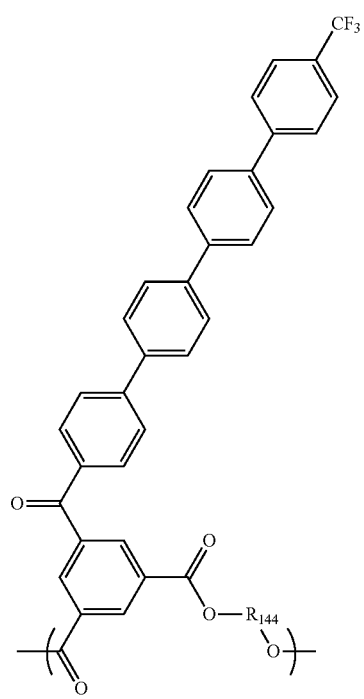
R_{144}
D-405
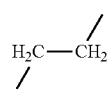
D-406
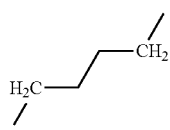
D-407
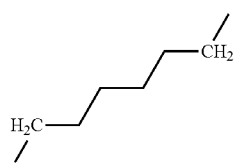

-continued
[Chem. 43]
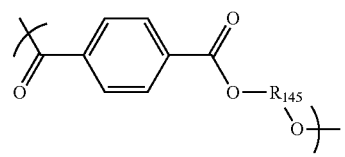
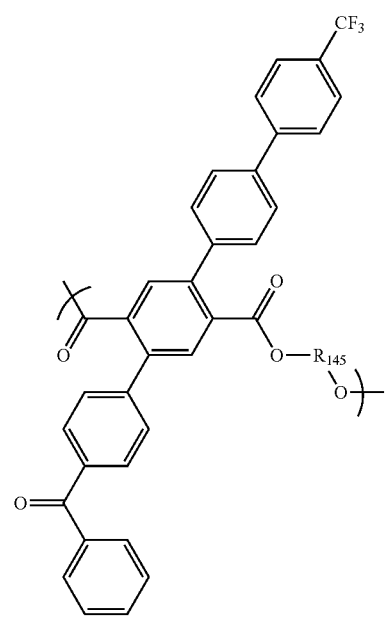
$R_{145}$
D-408
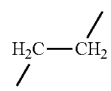
D-409
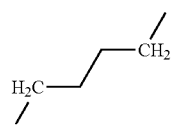
D-410
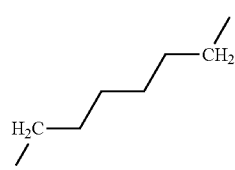

[Chem. 43]
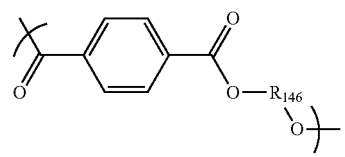 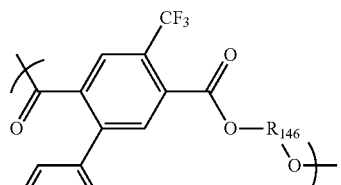
$R_{146}$
D-411
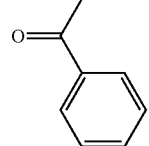
D-412
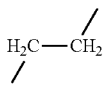
D-413
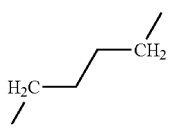

[Chem. 43]
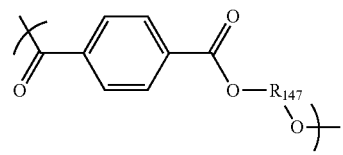
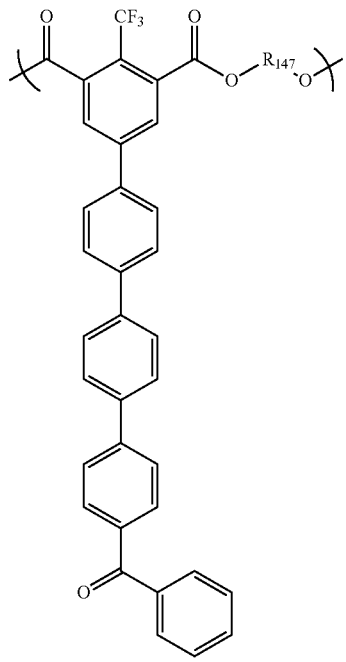
$R_{147}$
D-414
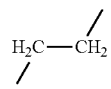
D-415
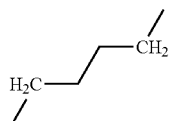
D-416
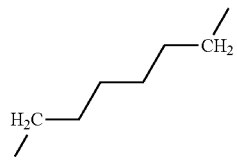

[Chem. 44]
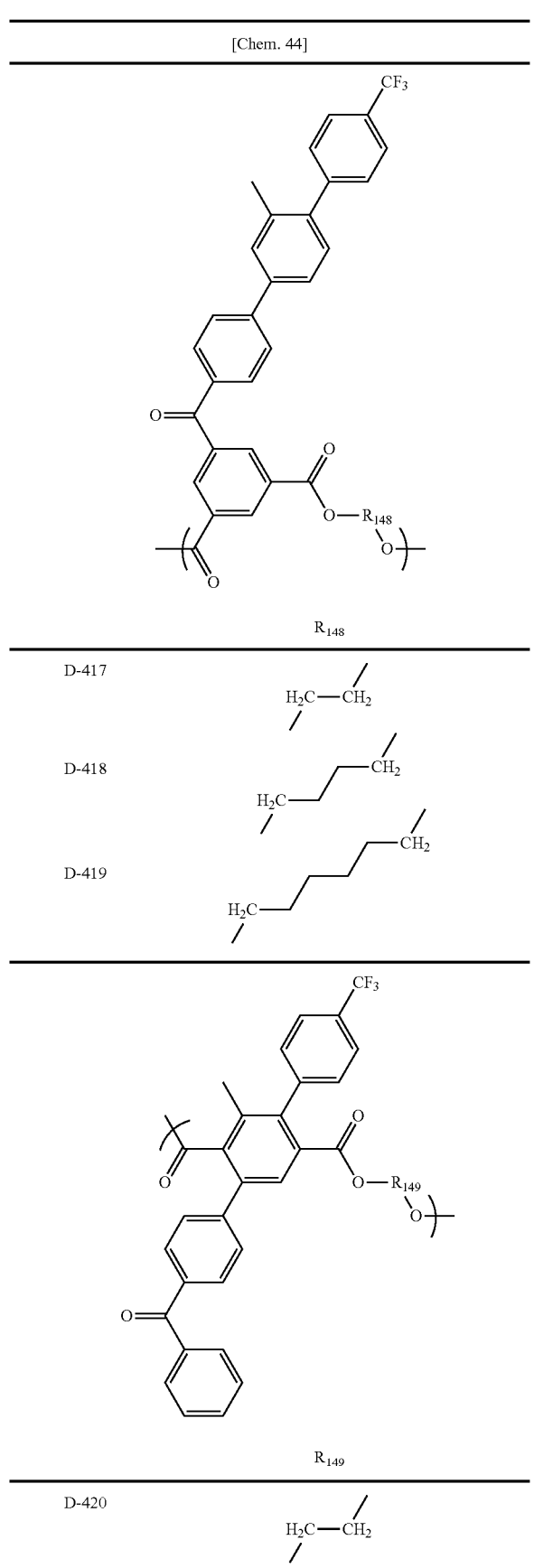
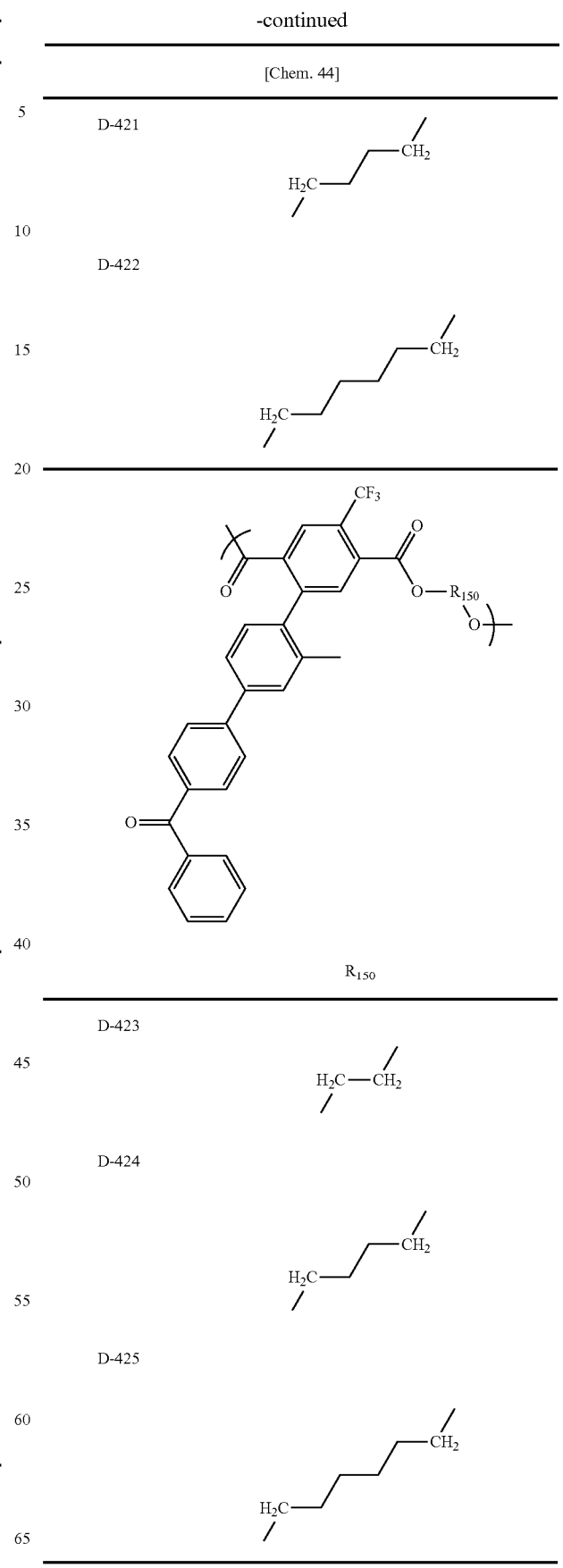

[Chem. 44]
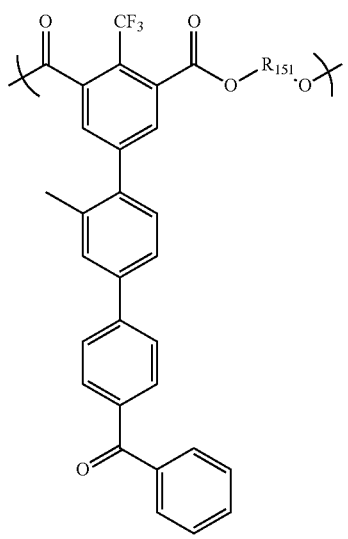
R$_{151}$
D-426
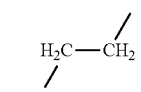
D-427
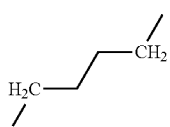
D-428
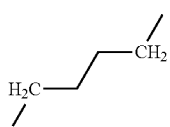
[Chem. 45]
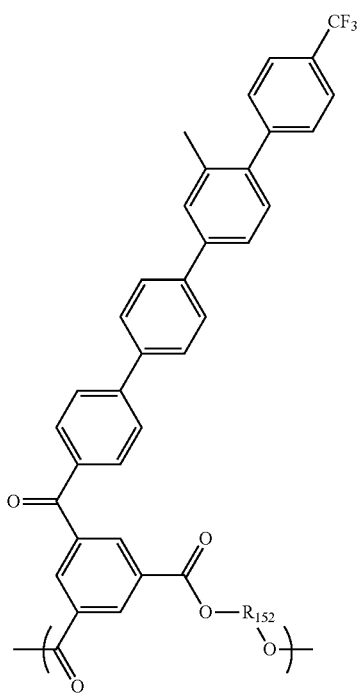
R$_{152}$
D-429
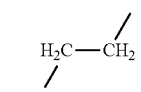
D-430
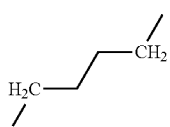
D-431
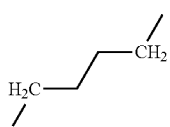

| [Chem. 45] | [Chem. 45] |
|---|---|
| 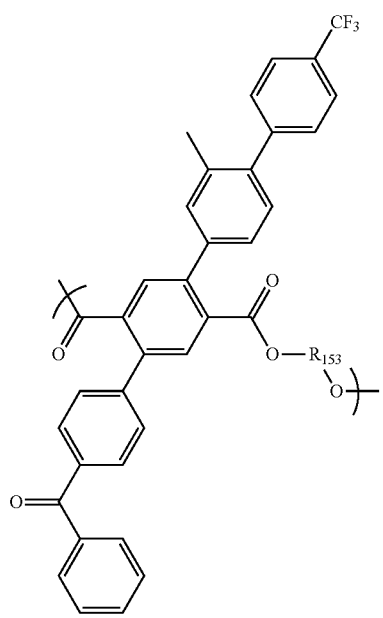 | 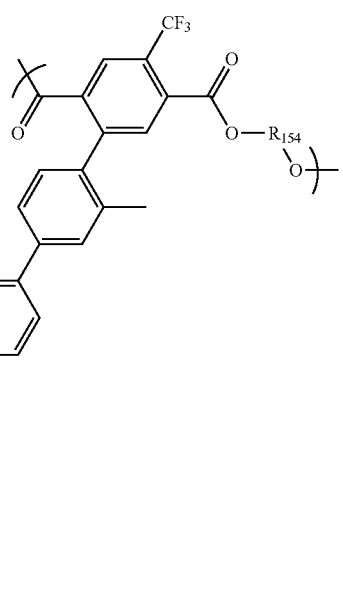 |
| $R_{153}$ | $R_{154}$ |
| D-432 | D-435 |
| $H_2C-CH_2$ | $H_2C-CH_2$ |
| D-433 | D-436 |
| | |
| D-434 | D-437 |
| | |

| 149 | 150 |
|---|---|
| -continued | |
| [Chem. 45] | [Chem. 46] |
| 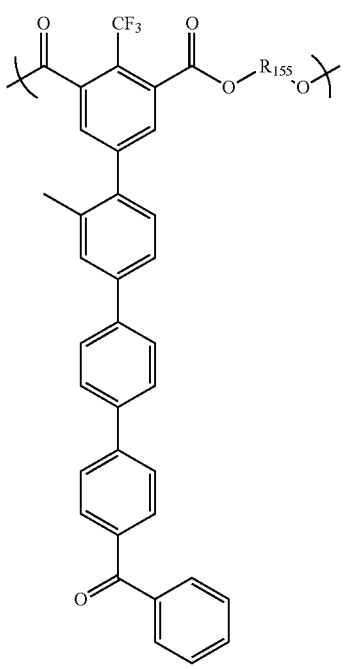 | 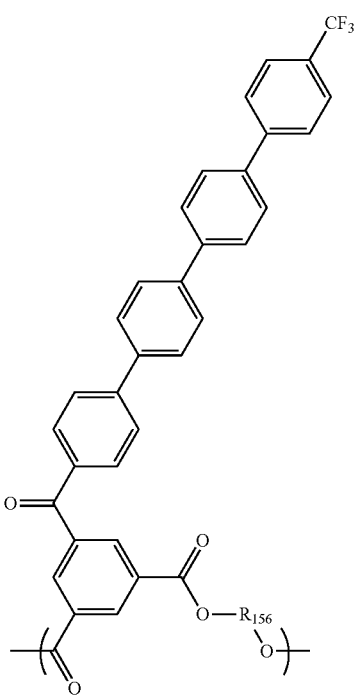 |
| R<sub>155</sub> | R<sub>156</sub> |
| D-438 | D-441 |
| 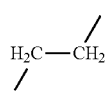 | 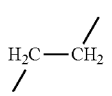 |
| D-439 | D-442 |
| 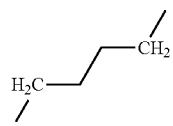 | 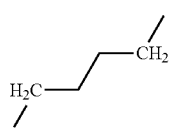 |
| D-440 | D-443 |
| 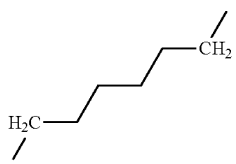 | 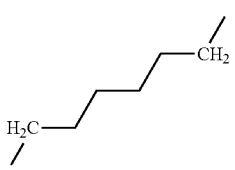 |

| 151 -continued | 152 -continued |
|---|---|
| [Chem. 46] | [Chem. 46] |
| 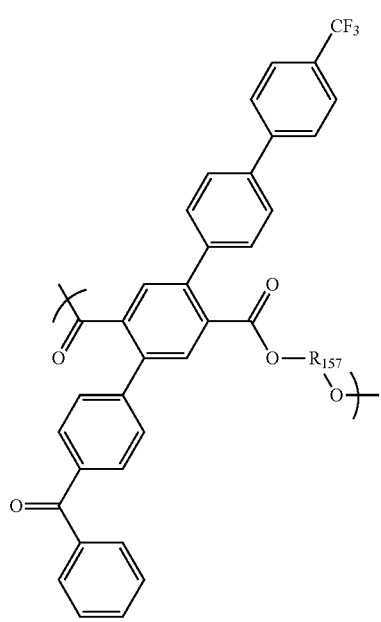 | 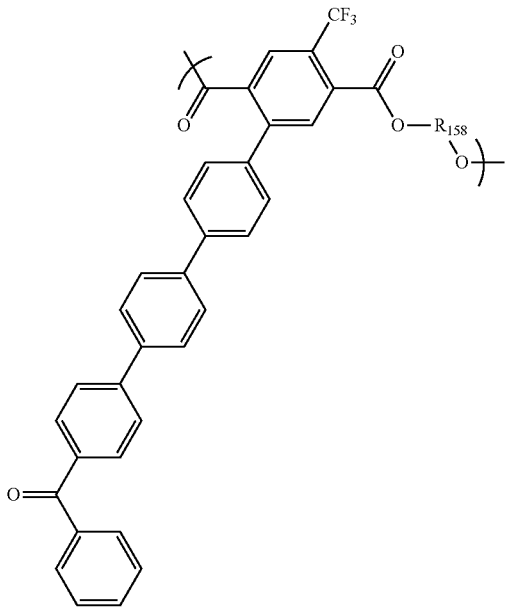 |
| R₁₅₇ | R₁₅₈ |
| D-444 | D-447 |
| 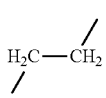 | 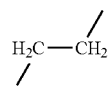 |
| D-445 | D-448 |
| 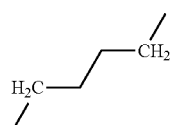 | 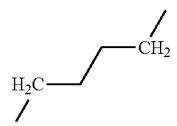 |
| D-446 | D-449 |
| 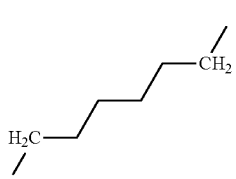 | |
| | R₁₅₉ |
| | D-450 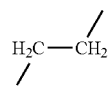 |

-continued
[Chem. 46]
D-451 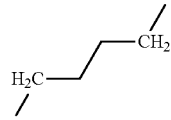
D-452 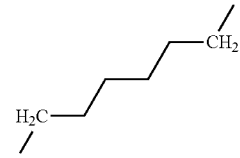
[Chem. 47]
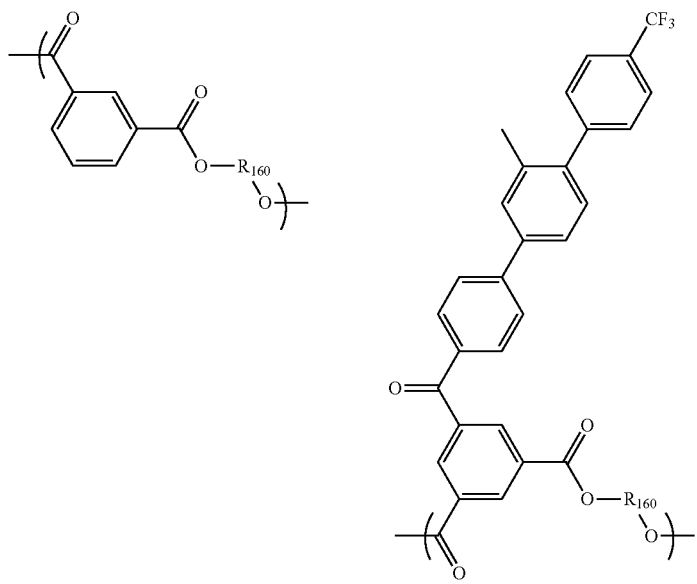
R$_{160}$
D-453 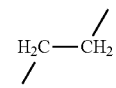
D-454 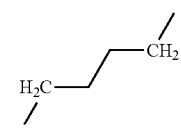
D-455 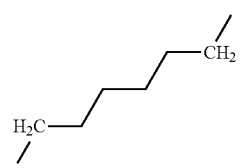

[Chem. 47]
| | |
|---|---|
| 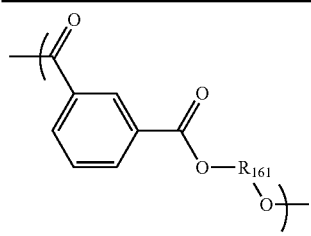 | 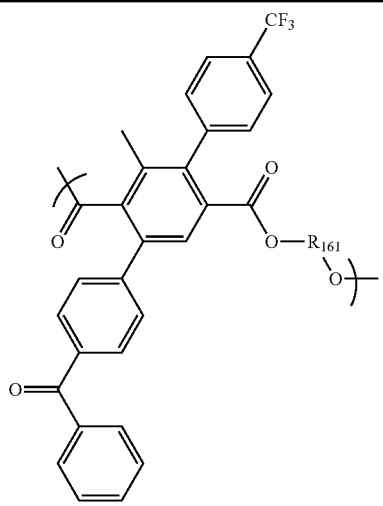 |
| | R<sub>161</sub> |
|---|---|
| D-456 | 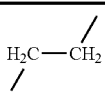 |
| D-457 | 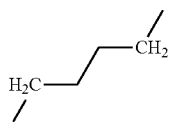 |
| D-458 | 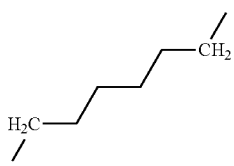 |
| | |
|---|---|
| 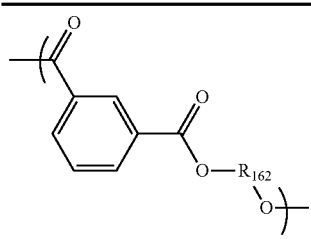 | 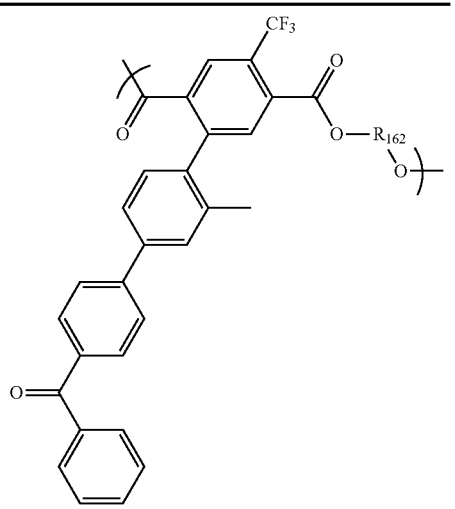 |
| | R<sub>162</sub> |
|---|---|
| D-459 | 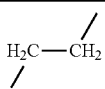 |

-continued
[Chem. 47]
D-460
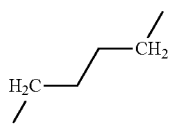
D-461
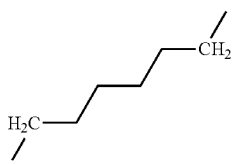
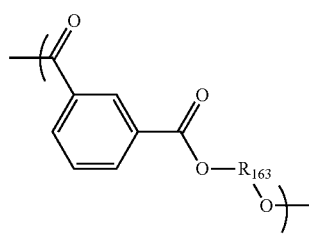
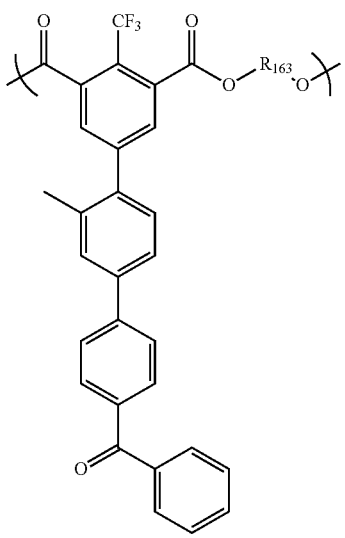
$R_{163}$
D-462
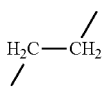
D-463
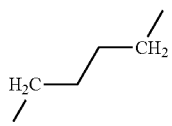
D-464
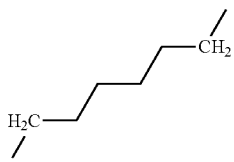

[Chem. 48]
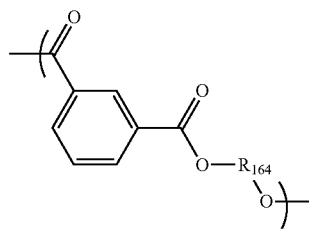
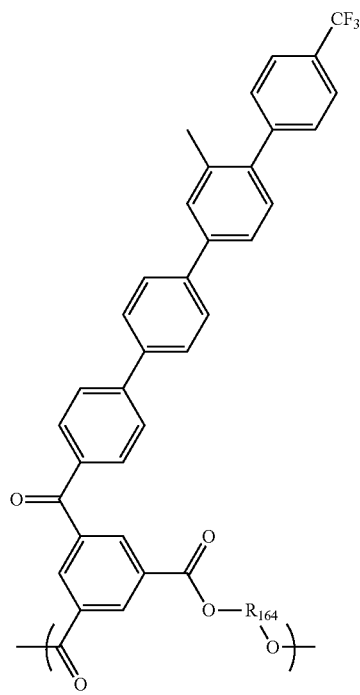
$R_{164}$
D-465
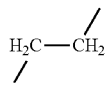
D-466
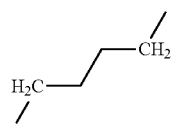
D-467
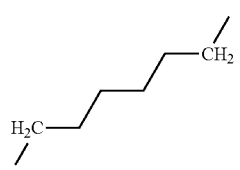

-continued
[Chem. 48]
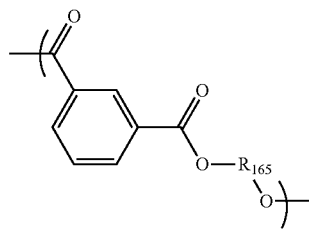
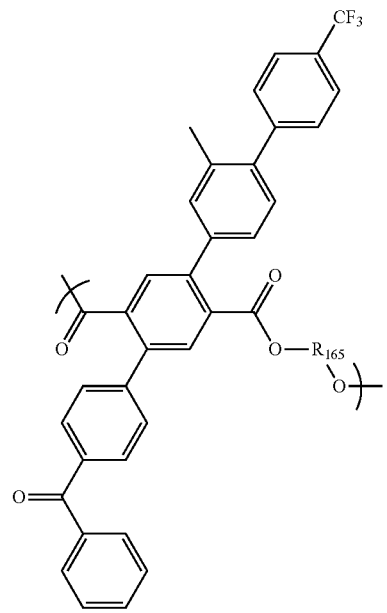
$R_{165}$
D-468
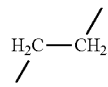
D-469
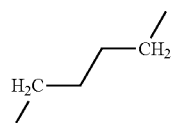
D-470
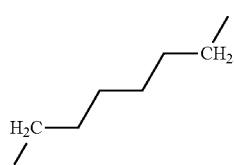

[Chem. 48]
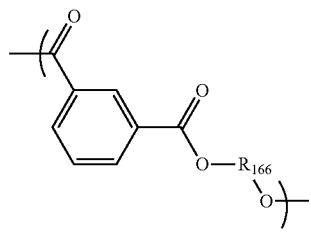 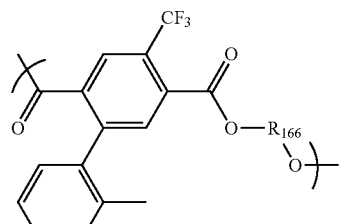
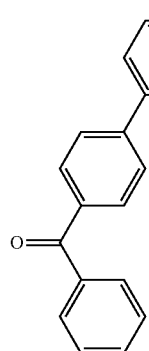
$R_{166}$
D-471
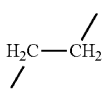
D-472
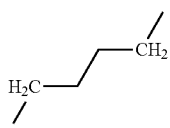
D-473
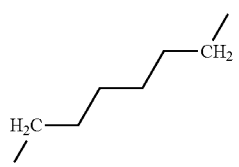

[Chem. 48]
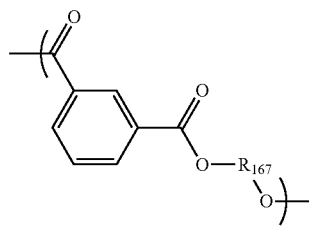 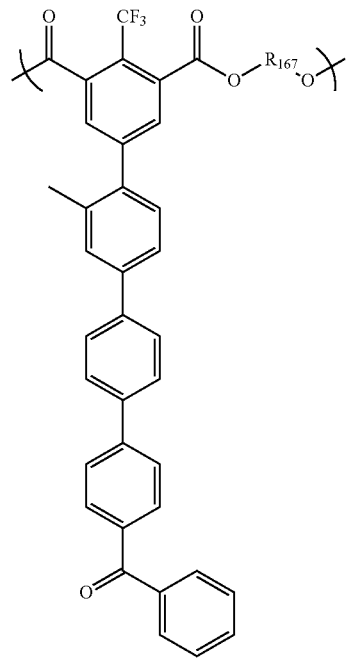
$R_{167}$
D-474
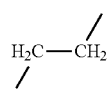
D-475
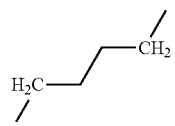
D-476
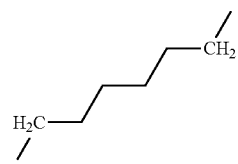

[Chem. 49]
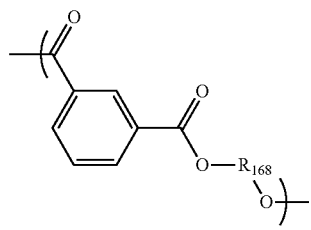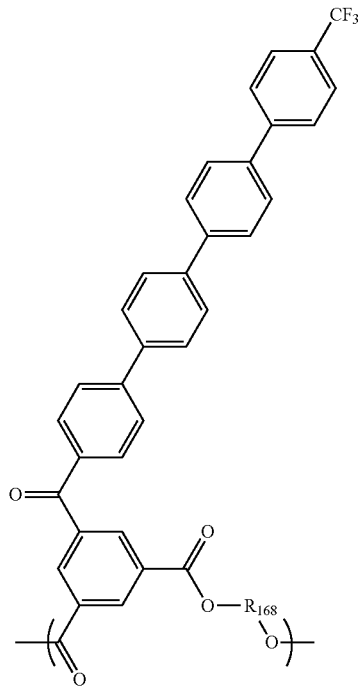
R_168
D-477
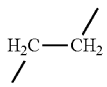
D-478
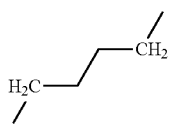
D-479
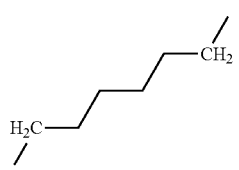

-continued
[Chem. 49]
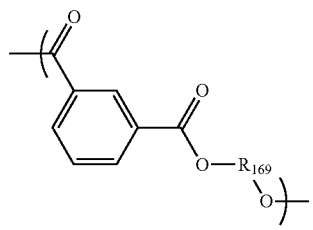
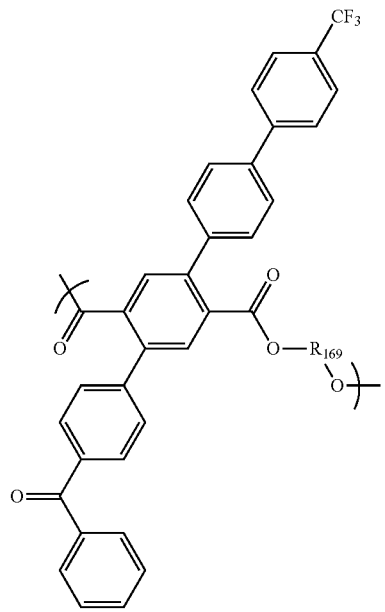
R169
D-480
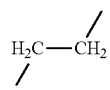
D-481
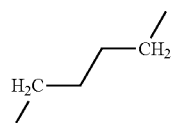
D-482
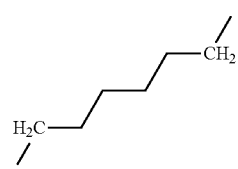

-continued
[Chem. 49]
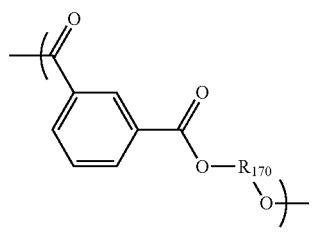
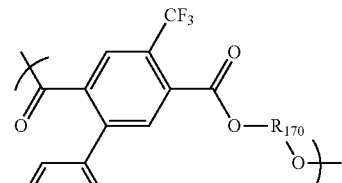
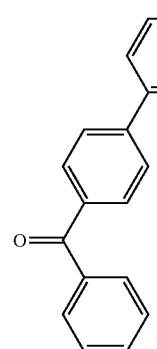
$R_{170}$
D-483
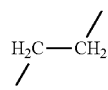
D-484
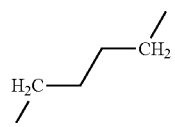
D-485
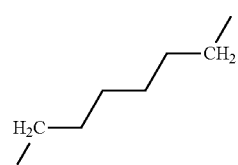

-continued
[Chem. 49]
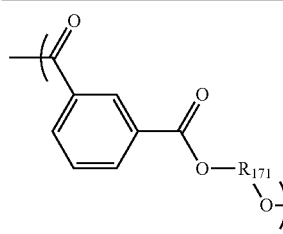 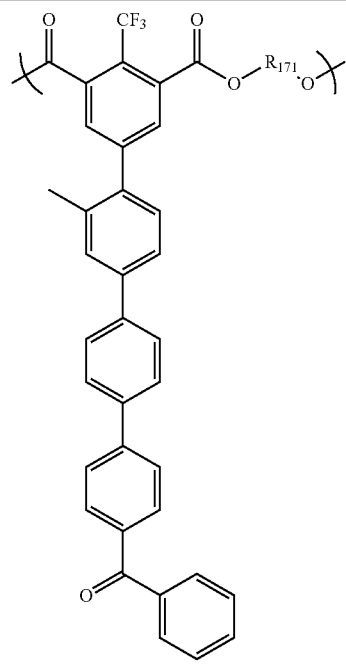
R₁₇₁
| | R₁₇₁ |
|---|---|
| D-486 | 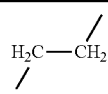 |
| D-487 | 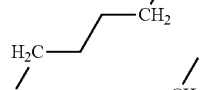 |
| D-488 | 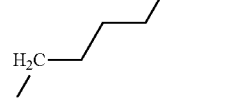 |
[Chem. 50]
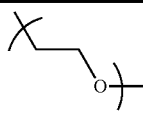 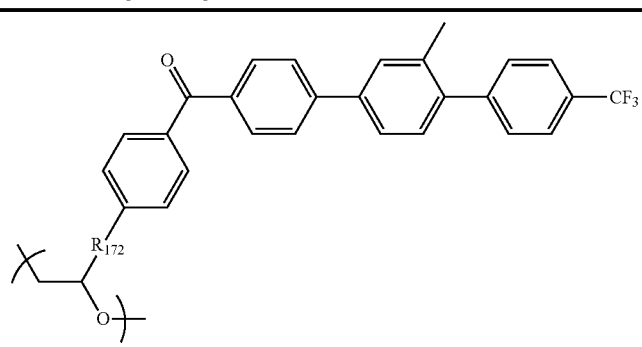
R₁₇₂
| | R₁₇₂ |
|---|---|
| D-489 |  |

-continued
[Chem. 50]
D-490 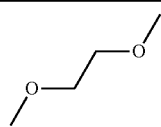
D-491 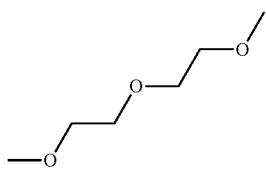
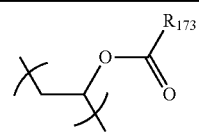  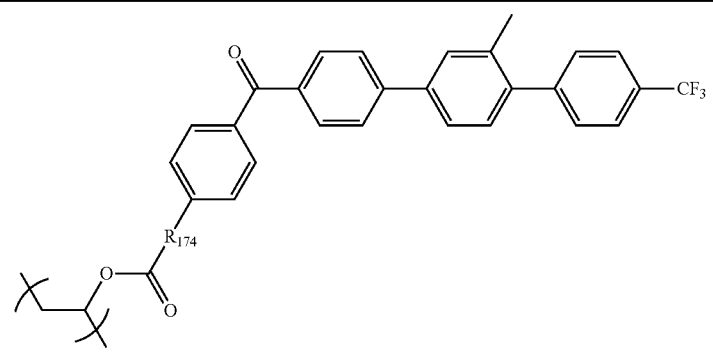
| | $R_{173}$ | $R_{174}$ |
|---|---|---|
| D-492 |  |  |
| D-493 | 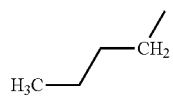 | 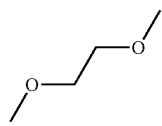 |
| D-494 | 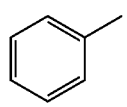 | 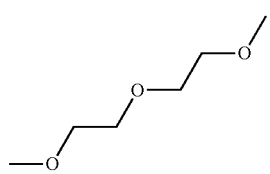 |
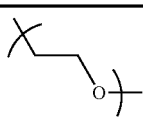  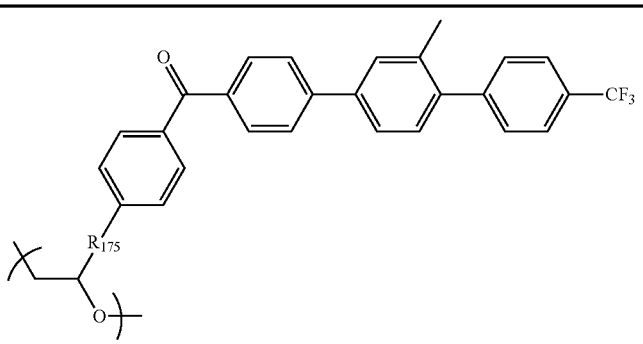
| | $R_{175}$ |
|---|---|
| D-495 |  |

-continued
[Chem. 50]
D-496
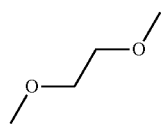
D-497
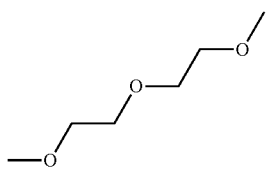
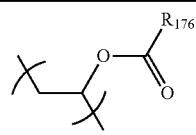
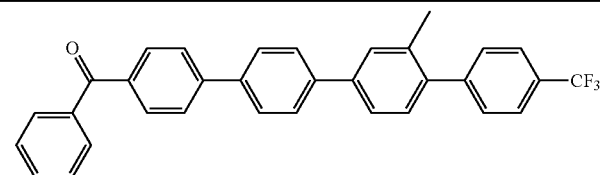
| | $R_{176}$ | $R_{177}$ |
|---|---|---|
| D-498 |  |  |
| D-499 | 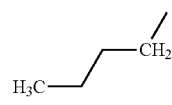 | 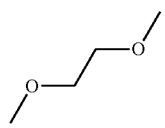 |
| D-500 | 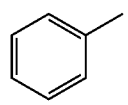 | 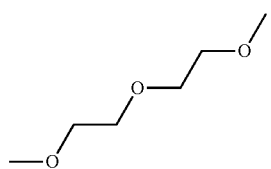 |
[Chem. 51]
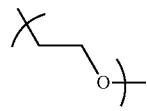
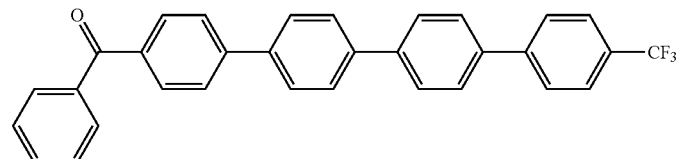
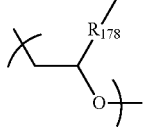
| | $R_{178}$ |
|---|---|
| D-501 |  |

-continued
[Chem. 51]
D-502 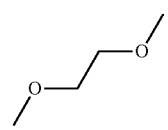
D-503 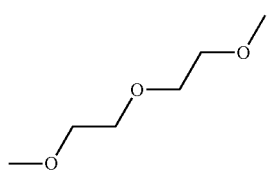
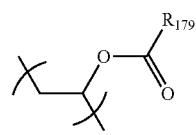 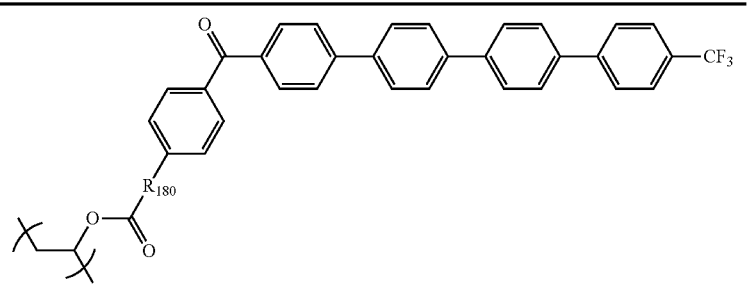
| | $R_{179}$ | $R_{180}$ |
|---|---|---|
| D-504 |  |  |
| D-505 | 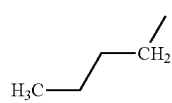 | 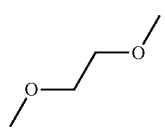 |
| D-506 | 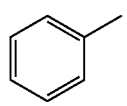 | 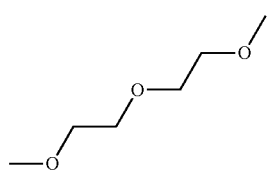 |
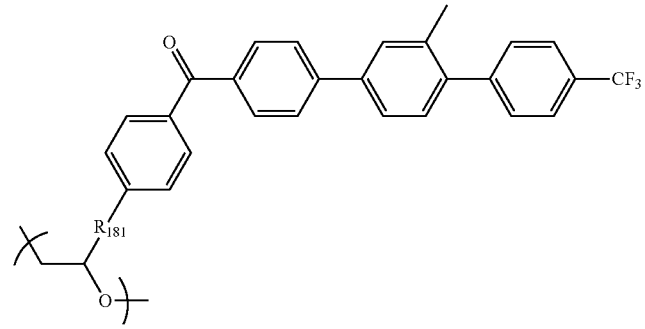
| | $R_{181}$ |
|---|---|
| D-507 |  |

-continued
[Chem. 51]
D-508 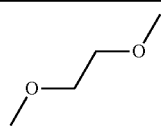
D-509 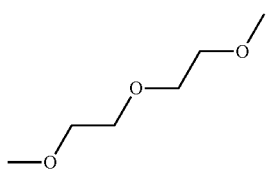
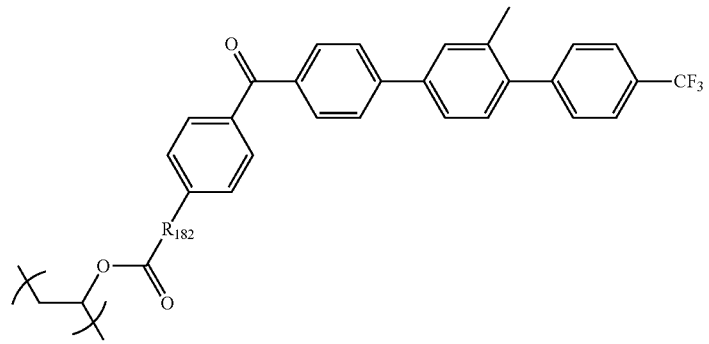
| | $R_{182}$ |
|---|---|
| D-510 |  |
| D-511 | 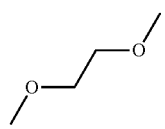 |
| D-512 | 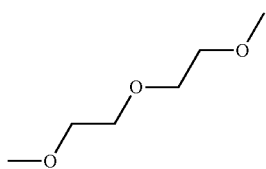 |
[Chem. 52]
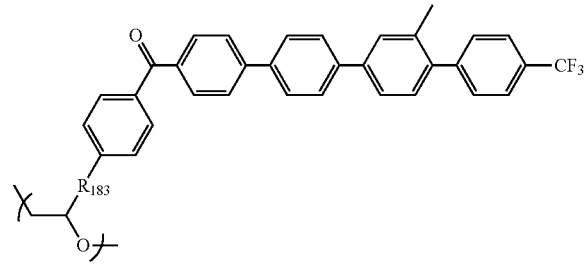
-continued
| | |
|---|---|
| D-514 | 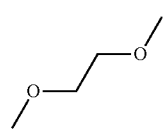 |
| D-515 | 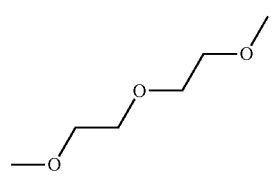 |
| | $R_{183}$ |
|---|---|
| D-513 | 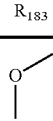 |

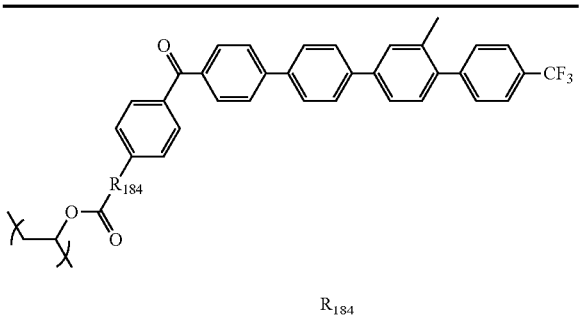

D-516

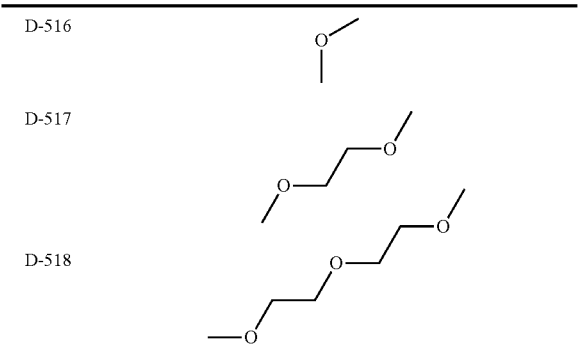

D-517

D-518

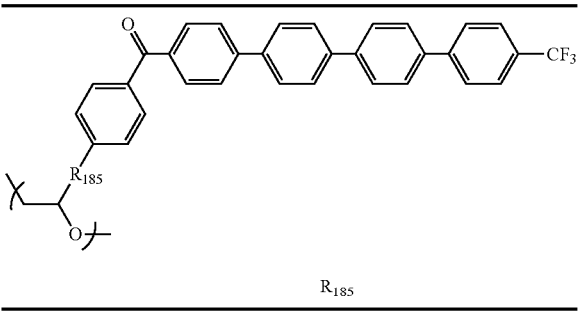

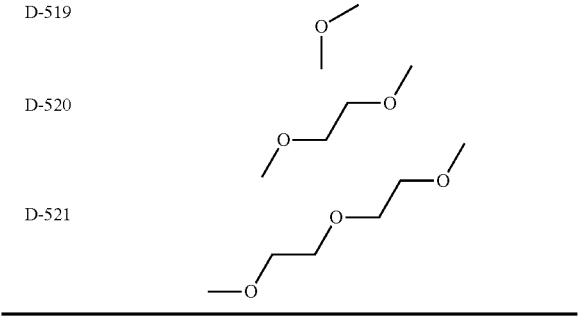

D-519

D-520

D-521

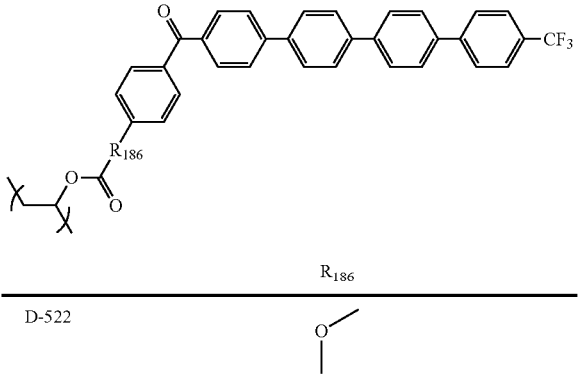

D-522

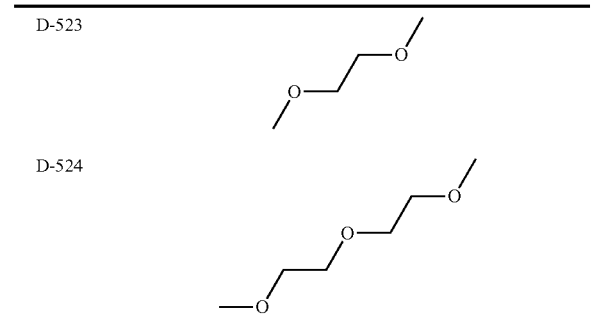

D-523

D-524

Recording Component Changing in Refractive Index or Reflected Light Intensity

The recording component changing in the reflected light intensity or refractive index, which is used in the non-resonant two-photon absorption recording material of the present invention, is described below.

In the non-resonant two-photon absorption recording material of the present invention, the non-resonant two-photon absorption recording material forming a recording layer preferably contains at least (a) a non-resonant polymer two-photon absorption compound and (b) a material capable of changing the reflected light intensity or refractive index between before and after two-photon recording, and it is more preferred that in the non-resonant two-photon absorption recording material forming a recording layer, the non-resonant polymer two-photon absorption compound is a material capable of changing the reflected light intensity or refractive index between before and after two-photon recording.

(Binder)

In the non-resonant two-photon absorption recording material of the present invention, a binder can be further used. The binder for use in the polymer composition of the present invention is not particularly limited and may be an organic polymer compound or an inorganic polymer compound. The organic polymer compound is preferably a solvent-soluble thermoplastic polymer, and one compound may be used alone or some compounds may be used in combination. A thermoplastic polymer well compatible with various components such as polymer two-photon absorption compound dispersed in the polymer composition is preferred.

Specific examples thereof include compounds described in paragraph 0022 of JP-A-2005-320502 (such as acrylate, α-alkyl acrylate ester, acidic polymer, interpolymer, polyvinyl ester, ethylene/vinyl acetate copolymer, saturated or unsaturated polyurethane, butadiene or isoprene polymer or copolymer, high molecular weight polyethylene oxide of polyglycol, epoxy compound, cellulose ester, cellulose ether, polycarbonate, norbornene-based polymer, polyvinylacetal, polyvinyl alcohol and polyvinylpyrrolidone), and also include a polystyrene polymer or a copolymer thereof, a polymer produced from a reaction product of a copolyester polymethylene glycol and an aromatic acid compound, or a mixture thereof, a poly-N-vinyl carbazole or a copolymer thereof, and a carbazole-containing polymer, described in the same paragraph as above. Other specific preferred examples include fluorine atom-containing polymers described in paragraphs 0023 to 0024 of the same patent publication.

Among these, an acrylate, an α-alkyl acrylate ester, a polystyrene, a polyalkylsytrene and a polystyrene copolymer are more preferred, and from the standpoint of enhancing the detection sensitivity, an acrylate, an α-alkyl acrylate, a polystyrene and a polystyrene copolymer are still more preferred. As for specific examples thereof, examples of the acrylate and α-alkyl acrylate ester include methyl(meth)acrylate, ethyl (meth)acrylate, propyl(meth)acrylate, butyl(meth)acrylate, isobutyl(meth)acrylate, pentyl(meth)acrylate, hexyl(meth) acrylate, octyl(meth)acrylate, 2-ethylhexyl(meth)acrylate, lauryl(meth)acrylate, stearyl(meth)acrylate and cyclohexyl (meth)acrylate; and examples of the benzene ring-containing (meth)acrylate include benzyl(meth)acrylate, phenoxyethyl (meth)acrylate, phenoxypolyethylene glycol(meth)acrylate and nonylphenol ethylene oxide adduct (meth)acrylate. Particularly preferred benzene ring-containing (meth)acrylates are a benzyl(meth)acrylate and phenoxyethyl(meth)acrylate. Only one kind of such a monomer may be used, or two or more kinds thereof may be used in combination. In the (meth) acrylate-based copolymer, other copolymerizable monomers capable of copolymerizing with an alkyl(meth)acrylate, a benzene ring-containing (meth)acrylate or a nitrogen-containing radical polymerizable monomer may be copolymerized, and examples of other copolymerizable monomers include alkyl vinyl ethers such as allyl glycidyl ether, methyl vinyl ether, ethyl vinyl ether, isobutyl vinyl ether, n-butyl vinyl ether, 2-ethyl hexyl vinyl ether, n-octyl vinyl ether, lauryl vinyl ether, cetyl vinyl ether and stearyl vinyl ether, alkoxyalkyl(meth)acrylates such as methoxyethyl(meth) acrylate and butoxyethyl(meth)acrylate, a glycidyl(meth) acrylate, a vinyl acetate, a vinyl propionate, an (anhydrous) maleic acid, an acrylonitrile, and a vinylidene chloride. A compound having a hydrophilic polar group may be also copolymerized, and examples of the polar group include —$SO_3M$, —$PO(OM)_2$, and —COOM (wherein M represents a hydrogen atom, an alkali metal or ammonium).

Examples of the polyalkylstyrene compound include polymethylstyrene, polyethylstyrene, polypropylstyrene, polybutylstyrene, polyisobutylstyrene, polypentylstyrene, hexylpolystyrene, polyoctylstyrene, poly-2-ethylhexylstyrene, polylaurylstyrene, polystearylstyrene, and polycyclohexylstyrene; and examples of the benzene ring-containing (meth) acrylate include polybenzylstyrene, polyphenoxyethylstyrene, polyphenoxy polyethylene glycol styrene and polynonylphenolstyrene. The position of the alkyl is preferably the α- or para-position. Only one kind of such a monomer may be used, or two or more kinds thereof may be used in combination. In the polystyrene copolymer, other copolymerizable monomers capable of copolymerizing with a conjugated diene compound, an alkylstyrene, a benzene ring-containing styrene or a nitrogen-containing radical polymerizable monomer may be copolymerized, and examples of other copolymerizable monomers include acetylene, butadiene, acrylonitrile, vinylidene chloride, polyethylene, allyl glycidyl ether, methyl vinyl ether, ethyl vinyl ether, isobutyl vinyl ether, n-butyl vinyl ether, 2-ethylhexyl vinyl ether, n-octyl vinyl ether, lauryl vinyl ether, cetyl vinyl ether and stearyl vinyl ether.

The binder used in combination with a polymer of the dye monomer is usually used for the purpose of enhancing the film-forming property of the composition before polymerization, the uniformity of film thickness, or the stability during storage.

The binder is preferably a solvent-soluble thermoplastic polymer, and the polymers may be used individually or in combination with each other.

The binder used in combination with a polymer of the dye monomer is preferably different in the refractive index from the polymerizable compound, and the polymerizable compound may have a larger refractive index or the binder may have a larger refractive index, but the refractive index of the polymerizable compound is preferably larger than that of the binder.

For this purpose, it is preferred that either one of the polymerizable compound and the binder contains at least one aryl group, aromatic heterocyclic group, chlorine atom, bromine atom, iodine atom or sulfur atom and the remaining one does not contain such a group or atom. More preferably, the polymerizable group contains at least one aryl group, aromatic heterocyclic group, chlorine atom, bromine atom, iodine atom or sulfur atom and the binder does not contain such a group or atom.

Preferred examples of the binder when the refractive index of the polymerizable compound is larger than the refractive index of the binder are described below.

Specific preferred examples of the low refractive index binder include an acrylate, an α-alkyl acrylate ester, an acidic polymer, an interpolymer (for example, polymethyl methacrylate, polyethyl methacrylate, and a copolymer of methyl methacrylate and another alkyl(meth)acrylate ester), a polyvinyl ester (e.g., polyvinyl acetate, polyvinyl acetate/acrylate, polyvinyl acetate/methacrylate, hydrolyzable polyvinyl acetate), an ethylene/vinyl acetate copolymer, a saturated or unsaturated polyurethane, a butadiene or isoprene polymer or copolymer, a high molecular weight polyethylene oxide of polyglycol having an average molecular weight of substantially from 4,000 to 1,000,000, an epoxidized product (for example, an epoxidized product having an acrylate or methacrylate group), a polyamide (e.g., N-methoxymethylpolyhexamethylene adipamide), a cellulose ester (e.g., cellulose acetate, cellulose acetate succinate, cellulose acetate butyrate), a cellulose ether (e.g., methyl cellulose, ethyl cellulose, ethylbenzyl cellulose), a polycarbonate, a polyvinylacetal (e.g., polyvinylbutyral, polyvinylformal), a polyvinyl alcohol, a polyvinylpyrrolidone, acid-containing polymers and copolymers disclosed in U.S. Pat. Nos. 3,458,311 and 4,273,857, and amphoteric polymer binders disclosed in U.S. Pat. No. 4,293,635. More preferred examples include a cellulose acetate butyrate polymer, a cellulose acetate lactate polymer, an acrylic polymer or interpolymer containing polymethyl methacrylate and copolymers of methyl methacrylate/ methacrylic acid and methyl methacrylate/acrylic acid, a terpolymer of methyl methacrylate/C2-C4 alkyl acrylate or methacrylate/acrylic or methacrylic acid, a polyvinyl acetate, a polyvinylacetal, a polyvinylbutyral, a polyvinylformal, and a mixture thereof.

A fluorine atom-containing polymer is also preferred as the low refractive index binder. The fluorine atom-containing polymer is preferably an organic solvent-soluble polymer containing a fluoroolefin as the essential component and containing, as the copolymerization component, one unsaturated monomer or two or more unsaturated monomers selected from an alkyl vinyl ether, an alicyclic vinyl ether, a hydroxy vinyl ether, an olefin, a haloolefin, an unsaturated carboxylic acid or an ester thereof, and a vinyl carboxylate. This polymer preferably has a mass average molecular weight of 5,000 to 200,000 and a fluorine atom content of 5 to 70 mass %.

Examples of the fluoroolefin used in the fluorine atom-containing polymer include tetrafluoroethylene, chlorotrifluoroethylene, vinyl fluoride and vinylidene fluoride. Examples of the alkyl vinyl ether as the other copolymerization component include ethyl vinyl ether, isobutyl vinyl ether and n-butyl vinyl ether. Examples of the alicyclic vinyl ether include cyclohexyl vinyl ether and its derivatives. Examples of the hydroxy vinyl ether include hydroxybutyl vinyl ether. Examples of the olefin and haloolefin include ethylene, propylene, isobutylene, vinyl chloride and vinylidene chloride.

Examples of the vinyl carboxylate include vinyl acetate and n-vinyl butyrate. Examples of the unsaturated carboxylic acid or an ester thereof include an unsaturated carboxylic acid such as (meth)acrylic acid and crotonic acid; C1-C18 alkyl esters of a (meth)acrylic acid, such as methyl(meth)acrylate, ethyl(meth)acrylate, propyl(meth)acrylate, isopropyl(meth)acrylate, butyl(meth)acrylate, hexyl(meth)acrylate, octyl(meth)acrylate and lauryl(meth)acrylate; C2-C8 hydroxyalkyl esters of a (meth)acrylic acid, such as hydroxyethyl(meth)acrylate and hydroxypropyl(meth)-acrylate; an N,N-dimethylaminoethyl(meth)acrylate; and an N,N-diethylaminoethyl(meth)acrylate. One of these radical polymerizable monomers may be used alone, or two or more kinds thereof may be used in combination. Furthermore, if desired, a part of the monomer may be replaced by another radical polymerizable monomer, for example, a vinyl compound such as styrene, α-methylstyrene, vinyltoluene and (meth)acrylonitrile. Also, other monomer derivatives such as carboxylic acid group-containing fluoroolefin and glycidyl group-containing vinyl ether may be used.

Specific examples of the above-described fluorine atom-containing polymer include "Lumifron" series having a hydroxyl group and being soluble in an organic solvent (for example, Lumifron LF200, weight average molecular weight: about 50,000, produced by Asahi Glass Company, Ltd.). In addition, organic solvent-soluble fluorine atom-containing polymers are commercially available from Daikin Kogyo Co., Ltd., Central Glass Co., Ltd., Penwalt and the like, and these can also be used.

Many of these binders form a non-three-dimensional crosslinked structure. The binder having a structure that forms a three-dimensional crosslinked structure is described below.

(Binder that Forms Three-Dimensional Crosslinked Structure)

Many of the above-described binders form a non-three-dimensional crosslinked structure, but in the optical recording material of the present invention, a binder that forms a three-dimensional crosslinked structure may be also used. The binder that forms a three-dimensional crosslinked structure is preferred in terms of enhancing he coatability, film strength and recording performance. Incidentally, the "binder that forms a three-dimensional crosslinked structure" is referred to as "matrix".

The matrix contains a component for forming the three-dimensional crosslinked structure, and this component for use in the present invention may contain a thermal crosslinking compound. As the crosslinking compound, a thermal crosslinking compound and a photocurable compound that is cured by using a catalyst or the like and irradiating the compound with light, may be used, and a thermal crosslinking compound is preferred.

The thermal crosslinking matrix for use in the present invention is not particularly limited and may be appropriately selected according to the purpose, but examples thereof include a urethane resin formed from an isocyanate compound and an alcohol compound, an epoxy compound formed from an oxirane compound, and a polymer obtained by polymerizing a melamine compound, a formalin compound, an ester compound of an unsaturated acid, such as (meth)acrylic acid or itaconic acid, or an amide compound. Above all, a polyurethane matrix formed from an isocyanate compound and an alcohol compound is preferred and in consideration of recording preservability, a polyurethane matrix formed from a polyfunctional isocyanate and a polyfunctional alcohol is most preferred.

Specific examples of the polyfunctional isocyanate and polyfunctional alcohol which can form a polyurethane matrix are described below.

Specific examples of the polyfunctional isocyanate include biscyclohexylmethane diisocyanate, hexamethylene diisocyanate, phenylene-1,3-diisocyanate, phenylene-1,4-diisocyanate, 1-methoxyphenylene-2,4-diisocyanate, 1-methylphenylene-2,4-diisocyanate, 2,4-tolylene diisocyanate, 2,6-tolylene diisocyanate, 1,3-xylylene diisocyanate, 1,4-xylylene diisocyanate, biphenylene-4,4'-diisocyanate, 3,3'-dimethoxybiphenylene-4,4'-diisocyanate, 3,3'-dimethylbiphenylene-4,4'-diisocyanate, diphenylmethane-2,4'-diisocyanate, diphenylmethane-4,4'-diisocyanate, 3,3'-dimethoxydiphenylmethane-4,4'-diisocyanate, 3,3'-dimethyldiphenylmethane-4,4'-diisocyanate, naphthylene-1,5-diisocyanate, cyclobutylene-1,3-diisocyanate, cyclopentylene-1,3-diisocyanate, cyclohexylene-1,3-diisocyanate, cyclohexylene-1,4-diisocyanate, 1-methylcyclohexylene-2,4-diisocyanate, 1-methylcyclohexylene-2,6-diisocyanate, 1-isocyanate-3,3,5-trimethyl-5-isocyanatomethylcyclohexane, cyclohexane-1,3-bis(methylisocyanate), cyclohexane-1,4-bis(methylisocyanate), isophorone diisocyanate, dicyclohexylmethane-2,4'-diisocyanate, dicyclohexylmethane-4,4'-diisocyanate, ethylene diisocyanate, tetramethylene-1,4-diisocyanate, hexamethylene-1,6-diisocyanate, dodecamethylene-1,12-diisocyanate, phenyl-1,3,5-triisocyanate, diphenylmethane-2,4,4'-triisocyanate, diphenylmethane-2,5,4'-triisocyanate, triphenylmethane-2,4',4"-triisocyanate, triphenylmethane-4,4',4"-triisocyanate, diphenylmethane-2,4,2',4'-tetraisocyanate, diphenylmethane-2,5,2',5'-tetraisocyanate, cyclohexane-1,3,5-triisocyanate, cyclohexane-1,3,5-tris(methylisocyanate), 3,5-dimethylcyclohexane-1,3,5-tris(methylisocyanate), 1,3,5-trimethylcyclohexane-1,3,5-tris(methylisocyanate), dicyclohexylmethane-2,4,2'-triisocyanate, dicyclohexylmethane-2,4,4'-triisocyanatelysine diisocyanate methyl ester, and a prepolymer with isocyanate at both ends obtained by reacting such an organic isocyanate compound in excess of the stoichiometric amount with a polyfunctional active hydrogen-containing compound. Among these, biscyclohexylmethane diisocyanate and hexamethylene diisocyanate are preferred. One of these may be used alone, or two or more kinds thereof may be used in combination.

The polyfunctional alcohol may be a polyfunctional alcohol alone or a mixture with other polyfunctional alcohols. Examples of the polyfunctional alcohol include glycols such as ethylene glycol, triethylene glycol, diethylene glycol, polyethylene glycol, propylene glycol, polypropylene glycol and neopentyl glycol; diols such as butanediol, pentanediol, hexanediol, heptanediol and tetramethylene glycol; bisphenols or compounds obtained by modifying such a polyfunctional alcohol with a polyethyleneoxy or polypropyleneoxy chain; glycerin; trimethylolpropane; and triols such as butanetriol, pentanetriol, hexanetriol and decanetriol or compounds obtained by modifying such a polyfunctional alcohol with a polyethyleneoxy or polypropyleneoxy chain.

The content of the matrix-forming component in the optical recording composition using the above-described dye monomer is preferably from 10 to 95 mass %, more preferably from 35 to 90 mass %.

The optical information medium and the manufacturing method thereof are described in detail by referring to each element constituting the optical recording medium.

[Substrate]

The optical recording medium of the present invention preferably has a substrate. As the substrate for use in the recording medium of the present invention, a substrate made of various materials employed as the substrate material of the conventional optical information recording medium may be arbitrarily selected and used. A disk-shaped substrate is preferably used as the substrate.

Specific examples of the substrate material include glass, polycarbonate, an acrylic resin such as polymethyl methacrylate, a vinyl chloride-based resin such as polyvinyl chloride and vinyl chloride copolymer, an epoxy resin, an amorphous polyolefin, a polyester, and a metal such as aluminum. These may be used in combination, if desired.

Among these materials, in view of humidity resistance, dimensional stability, low cost and the like, a thermoplastic resin such as amorphous polyolefin and polycarbonate is preferred, and a polycarbonate is more preferred.

In the case of using such a resin, the substrate can be produced by using injection molding. Also, the substrate may be produced by forming the resin in a film shape and punching out the film in a disc shape.

The thickness of the substrate is in general preferably from 0.02 to 2 mm, more preferably from 0.6 to 2 mm, still more preferably from 0.7 to 1.5 mm, yet still more preferably from 0.9 to 1.2 mm. Also, two recording mediums may be laminated together to make up a double-side recordable medium. In this case, the thickness of one substrate is from 0.2 to 0.7 mm, preferably from 0.3 to 0.6 mm, more preferably from 0.4 to 0.5 mm.

Furthermore, in order to enable high-speed recording/reproduction and increase the recording capacity per volume, the thickness of the substrate may be more greatly reduced than in a general optical disc, thereby imparting flexibility. In this case, the thickness of the substrate is from 0.02 to 0.4 mm, preferably from 0.05 to 0.35 mm, more preferably from 0.1 to 0.3 mm.

In the center of the substrate, a hole for chucking is generally provided. Also, a hub may be provided in place of a hole.

[Guide Layer]

A concentric or spiral guide layer may be provided so as to perform the radial position control by a tracking servo during recording of the optical medium. The guide layer is generally has a continuous or intermittent concavo-convex structure and in the conventional optical disc, one groove is continuously formed to run spirally from the inner circumference to the outer circumference of a disc-shaped medium. A preferred range of the groove depth is determined by the laser wavelength used for tracking. In the case of employing a push-pull system for the tracking, assuming that the laser wavelength used for tracking is X and the refractive index in the groove is n, the tracking signal obtained from the groove becomes maximum when the groove thickness is $\lambda/(8n)$, and becomes 0 when the groove depth is 0 and $\lambda/(4n)$. Therefore, the groove depth d is in the range of $0<d<\lambda/(4n)$. The groove depth d is preferably in the range of $\lambda/(12n)<d<\lambda/(6n)$, more preferably $d=\lambda/(8n)$.

The width of the guide groove may be set according to the track pitch, and in general, a high-intensity push-pull signal can be obtained by setting the width to about half of the track pitch.

In the guide layer, a structure capable of producing a clock signal for rotation synchronization during recording can be provided. In general, a wobble groove system of causing the groove to meander with an arbitrary frequency is employed. The recording apparatus can be controlled to a specified recording linear velocity by referring to the periodic signal fluctuation obtained from the wobble groove. Also, address information may be provided in the guide layer. In the case of a wobble groove system, a frequency modulation system of combining large and small frequencies with respect to the carrying frequency, thereby imparting arbitrary address information, a phase modulation system of imparting address information by changing the wobble phase, a system of superimposing the address information, and the like can be used. Also, a so-called land pre-pit system of providing a mark aside the groove and forming address information by its position may be used. In addition, information necessary for recording/reproduction control, such as calibration of recording power, corresponding linear velocity and signal polarity, may be also previously recorded in the guide information by using the same method as that for the address information.

The position in the depth direction at which the guide layer is provided may be any position as long as it is a position reproducible by the tracking laser, and in the case of providing the guide layer on the substrate surface, the substrate molding and the guide layer formation can be performed simultaneously by pressing a metal stamper having engraved therein a guide layer geometry at the molding of the substrate. Also, the guide layer may be formed by coating an ultraviolet-curable resin or the like on the molded substrate, pressing the stamper and then curing the resin. The guide layer can be formed in the same manner also in the case where the guide layer is provided adjacent each recording layer, provided as an intermediate layer between recording layers, or provided adjacent a cover layer. It is also possible that the metal stamper is heated to a temperature not lower than the softening point of the resin layer for providing the guide layer and then pressed to transfer the pattern.

[Reflecting Layer]

A reflecting layer can be provided adjacent the guide layer or recording layer so as to increase the reflected signal intensity.

The material for the reflecting layer may be selected from material species capable of providing for the required reflectance at the readout wavelength and, for example, a metal such as Mg, Se, Y, Ti, Zr, Hf, V, Nb, Ta, Cr, Mo, W, Mn, Re, Fe, Co, Ni, Ru, Rh, Pd, Ir, Pt, Cu, Ag, Au, Zn, Cd, Al, Ga, In, Si, Ge, Te, Pb, Po, Sn and Bi, and a semimetal may be used. Among these, Ag, Au and Al are preferred, because a high reflectance is obtained. One of these materials may be used alone, or a plurality thereof may be mixed and used. Also, a small amount of an additive element may be added for reforming.

The reflected light can be also produced by using a high refractive index or low refractive index material as the reflecting layer and thereby creating a refractive index difference from the adjacent layer. Examples of the high refractive index material include titanium oxide ($TiO_2$), cerium oxide ($CeO_2$), zirconium oxide ($ZrO_2$), niobium oxide ($Nb_2O_5$), tantalum oxide ($Ta_2O_5$), tungsten oxide ($WO_3$), zinc oxide ($ZnO$), and indium oxide ($In_2O_3$). Examples of the low refractive index material include aluminum fluoride ($AlF_3$), calcium fluoride ($CaF_2$), lithium fluoride ($LiF$), magnesium fluoride ($MgF_2$), and sodium fluoride ($NaF$). One of these materials may be used alone, or a plurality thereof may be mixed and used. Such an inorganic compound is film-formed by sputtering, deposition, ion plating, molecular beam epitaxy or other methods, whereby the reflecting layer can be formed.

In the case where the wavelength differs between the recording/readout laser and the tracking laser, it is also possible to establish a high reflectance for the tracking laser and a low reflectance for the recording/readout laser by using a wavelength-selective reflecting layer material and thereby reduce unnecessary reflected light. Specifically, in the case of using light at the 405 nm wavelength as the recording/readout laser and light at the 660 nm wavelength as the tracking laser, when Au exhibiting a high reflectance at a wavelength longer than 500 nm and abruptly decreasing in the reflectance at a wavelength shorter than 500 nm is used as the reflecting layer, the light of the tracking laser is strongly reflected to reduce the reflectance of the recording/readout light, whereby stray light due to reflection of the recording/readout light can be reduced.

[Intermediate Layer]

An intermediate layer for physically separating the recording layer and producing an interface capable of forming a recording mark by expansion is provided between adjacent recording layers.

The interface reflection between the recording layer and the intermediate layer occurs mainly due to the refractive index different between those two layers and therefore, a refractive index difference needs to be created between the recording layer and the intermediate layer. In the case where the intermediate layer is located on both sides of the recording layer in a multilayer structure, the recording layer may be formed to create the same refractive index difference from both intermediate layers and bring about occurrence of interface reflection from top and bottom of the recording layer or may be formed such that out of the intermediate layers located on both sides of the recording layer, the refractive index of the intermediate layer on one side is the same as that of the recording layer and the refractive index of the intermediate layer on another side is different from that of the recording layer, thereby bringing about occurrence of reflected light only from the interface on one side of the recording layer. In this case, the reflectance of the recording layer can be reduced in the fluctuation due to light interference as compared with the case of producing reflected light form the interfaces on both sides of the recording layer. Also, in this case, the intermediate layers on the top and bottom of the recording layer may be formed of different materials.

The refractive index difference between the recording layer and the intermediate layer is generally from 0.01 to 0.5, preferably from 0.04 to 0.4, more preferably from 0.08 to 0.25. If the refractive index difference is too small, necessary reflected light is not obtained, whereas if it is too large, the material used is limited.

If the thickness of the intermediate layer is too small, there is a problem that optical separation of adjacent recording layers from each other is difficult or so-called crosstalk between layers occurs, for example, by receiving a thermal effect, whereas if the thickness is too large, the number of recording layers can be hardly increased. For this reason, the thickness of the intermediate layer is from 2 to 20 µm, preferably from 4 to 15 µm, more preferably from 6 to 10 µm.

The intermediate layer is preferably transparent to light at the recording/readout wavelength and the tracking wavelength. The "transparent" means that the transmittance for light used in the recording and readout is 80% or more.

Respective intermediate layers may have the same film thickness or may be different in the film thickness. Considering that a smaller distance from the incident surface leads to a lower aberration of the optical system, it is also effective to make the intermediate layer close to the incident side thinner.

As the material for the intermediate layer, a thermoplastic resin, a thermosetting resin, an ultraviolet-curable resin, an electron beam-curable resin, a self-adhesive agent and the like can be used.

The ultraviolet-curable resin is composed of a urethane resin, an acrylic resin, a urethane acrylate resin, an epoxy resin, a fluoropolymer such as perfluoropolyether, a silicon-based polymer such as polydimethylsiloxane, or a mixture with a photopolymerization initiator or the like.

As the photopolymerization initiator, a known initiator can be used, and out of the photopolymerization initiators, examples of the radical photoinitiator include Darocur 1173, Irgacure 651, Irgacure 184 and Irgacure 907 (all produced by Ciba Specialty Chemicals Corporation). The content of the photopolymerization initiator is, for example, approximately from 0.5 to 5 mass % in an ultraviolet-curable resin agent composition (as solid content).

Also, the composition may contain, if desired, a non-polymerizable diluting solvent, a photopolymerization initiation aid, an organic filler, a polymerization inhibitor, an antioxidant, an ultraviolet absorber, a light stabilizer, a defoaming agent, a leveling agent, a pigment, a silicon compound and the like. Examples of the non-polymerizable diluting solvent include isopropyl alcohol, n-butyl alcohol, methyl ethyl ketone, methyl isobutyl ketone, isopropyl acetate, n-butyl acetate, ethyl cellosolve, and toluene. Examples of the ultraviolet absorber include benzotriazole-based, benzophenone-based, oxalic acid anilide-based and cyano acrylate-based compounds.

The ultraviolet-curable resin layer can be formed by a known film-forming method. For example, air doctor coating, blade coating, rod coating, knife coating, squeeze coating, impregnation coating, reverse roll coating, transfer roll coating, gravure coating, kiss roll coating, cast coating, curtain coating, calender coating, extrusion coating, spray coating, spin coating, hot-melt coating, vapor deposition or extrusion may be used.

As the self-adhesive agent used for the self-adhesive layer, for example, an acrylic, rubber-based or silicon-based self-adhesive agent can be used. In view of transparency and durability, an acrylic self-adhesive agent is preferred.

An acrylic copolymer obtained by copolymerizing, as a main monomer, a low Tg monomer such as butyl acrylate, ethyl acrylate and 2-ethylhexyl acrylate with a polyfunctional group monomer such as acrylic acid, methacrylic acid, hydroxyethyl methacrylate, hydroxyethyl acrylate, acrylamide and acrylonitrile is crosslinked, for example, by an isocyanate-based, melamine-based, epoxy-based or urethane-based crosslinking agent, whereby the acrylic self-adhesive agent can be obtained. Other photocurable oligomers•monomers, polymerization initiators, diluting solvents, tackifiers, antioxidants, sensitizers, crosslinking agents, ultraviolet absorbers, polymerization inhibitors, fillers, thermoplastic resins•dyes•pigments, and the like can be cured or added. Such a self-adhesive composition is coated on a separator.

As the separator, a release-treated plastic film or paper having a thickness of 25 to 100 µm, such as polyester film, polypropylene film, polyethylene film, polycarbonate film, polystyrene film and triacetyl cellulose film, can be used. Among these, a biaxially stretched polyester film is preferred, because a smoother surface is readily obtained and the productivity is excellent. The separator surface coming into contact with the self-adhesive agent layer is subjected to a treatment with a release agent. Examples of the release agent include a simple substance, a modification product, a mixture and the like of a silicone resin, a fluororesin, a polyvinyl alcohol resin and an alkyl group-containing resin. Among these, a silicone resin making it easy to lightly separate the adhesive layer may be preferably used, and in particular, a silicone resin cured with heat, ultraviolet ray, electron beam or the like may be more preferably used, because the silicone resin is less likely to transfer and adhere to the adhesive layer.

The self-adhesive layer can be coated on the separator by a known film-forming method. For example, air doctor coating, blade coating, rod coating, knife coating, squeeze coating, impregnation coating, reverse roll coating, transfer roll coating, gravure coating, kiss roll coating, cast coating, curtain coating, calender coating, extrusion coating, spray coating, spin coating, or hot-melt coating may be used. The composition coated is dried and cured, for example, by irradiation with an active energy ray, whereby an intermediate layer of a self-adhesive agent is formed. It is also possible that the coating is stacked on the medium in the state of not completely finishing the curing and after stacking, curing is completed by heating, irradiation with an ultraviolet ray, or other methods.

The intermediate layer may be film-formed directly on the medium or may be stacked on the medium after previously preparing a laminate structure with the recording layer. In the case of using a self-adhesive layer for the intermediate layer, the recording layer and the intermediate layer are press-bonded by a known method described, for example, in JP-A-209328 and JP-A-2011-81860, whereby the laminate can be formed. Furthermore, a laminate containing two or more recording layers and two or more intermediate layers can be also formed by stacking the laminates one on another. This laminate can be stacked on the medium by arranging the self-adhesive layer to face the substrate, guide layer, reflecting layer, cover sheet, spacer layer, or the already formed recording layer or intermediate layer and pressure-contacting it by a roller or the like.

[Recording Layer]

In the recording layer of the present invention, when irradiated with recording light, the dye moiety absorbs recording light to generate heat and the polymer moiety deforms due to the heat to form a convex geometry on the interface with the adjacent layer, whereby information is recorded.

The geometry change for obtaining a signal intensity necessary for recording/readout requires a recording layer having a certain extent of thickness to achieve expansion, and the thickness is preferably from 50 nm to 5 more preferably from 100 nm to 3 μm, still more preferably from 200 nm to 2 μm.

In the recording layer, an additive such as binder, antifading agent, exothermic agent, plasticizer and refractive index adjusting agent may be added, if desired.

Examples of the binder include a natural organic polymer substance such as gelatin, cellulose derivative, dextran, rosin and rubber; and a synthetic organic polymer including a hydrocarbon-based resin such as polyethylene, polypropylene, polystyrene and polyisobutylene, a vinyl-based resin such as polyvinyl chloride, polyvinylidene chloride and polyvinyl chloride•polyvinyl acetate copolymer, an acrylic resin such as polymethyl acrylate and polymethyl methacrylate, a polyvinyl alcohol, a chlorinated polyethylene, an epoxy resin, a butyral resin, a rubber derivative, and an initial condensate of a thermosetting resin, such as phenol•formaldehyde resin.

The antifading agent includes an organic oxidant and a singlet oxygen quencher. As the organic oxidant used as the antifading agent, the compounds described in JP-A-10-151861 are preferred. As the singlet oxygen quencher, those described in publications such as already known patent specifications can be utilized. Specific examples thereof include JP-A-58-175693, JP-A-59-81194, JP-A-60-18387, JP-A-60-19586, JP-A-60-19587, JP-A-60-35054, JP-A-60-36190, JP-A-60-36191, JP-A-60-44554, JP-A-60-44555, JP-A-60-44389, JP-A-60-44390, JP-A-60-54892, JP-A-60-47069, JP-A-63-209995, JP-A-4-25492, JP-B-1-38680, JP-B-6-26028, German Patent No. 350399, and Bulletin of the Chemical Society of Japan, page 1141, October 1992.

Examples of the plasticizer include triethylene glycol dicaprylate, triethylene glycol bis(2-ethylhexanoate), tetraethylene glycol diheptanoate, diethyl sebacate, dibutyl suberate, tris(2-ethylhexyl)phosphate, tricresyl phosphate, and dibutyl phthalate.

As the refractive index adjusting agent, for example, various polymer materials or a fine particle of a transparent inorganic material such as $SiO_2$ and $TiO_2$ can be used.

The recording layer can be formed by a known film-forming method. For example, air doctor coating, blade coating, rod coating, knife coating, squeeze coating, impregnation coating, reverse roll coating, transfer roll coating, gravure coating, kiss roll coating, cast coating, curtain coating, calender coating, extrusion coating, spray coating, spin coating, hot-melt coating, vapor deposition or extrusion may be used.

In the case of using solvent coating, the components of the recording layer are dissolved or dispersed in a coating solvent. The coating solvent may be selected by taking into consideration the solubility, decomposability, coating suitability and the like of the components of the recording layer, and, for example, one member or a mixture of a plurality of members selected from an alcohol-based solvent such as methyl alcohol, ethyl alcohol, propyl alcohol, butyl alcohol, allyl alcohol, furfuryl alcohol, methyl cellosolve, ethyl cellosolve and tetrafluoropropanol; an aliphatic or alicyclic hydrocarbon-based solvent such as hexane, heptane, octane, decane, cyclohexane, methyl cyclohexane, dimethyl cyclohexane, trimethyl cyclohexane and propyl cyclohexane; an aromatic hydrocarbon-based solvent such as toluene, xylene and benzene; a halogenated hydrocarbon-based solvent such as carbon tetrachloride and chloroform; an ether-based solvent such as diethyl ether, dibutyl ether, diisopropyl ether, dioxane and tetrahydrofuran; a ketone-based solvent such as acetone; an ester-based solvent such as ethyl acetate; and water, is used. Such a solvent and the components of the recording layer are mixed and then, for example, stirred, treated with an ultrasonic wave or heated, whereby the coating solvent is prepared. The solvent used can be removed by evaporation at the drying. Heating or pressurization may be used for the removal by evaporation.

The recording layer may be formed directly on the substrate or may be stacked on the substrate after previously preparing a laminate structure with the intermediate layer. In the case of using a self-adhesive layer for the intermediate layer, the recording layer is formed by coating on the separator or a release adding layer and then laminated with the intermediate layer by a known method described, for example, in JP-A-2005-209328 and JP-A-2011-81860, whereby a laminate of the recording layer and the intermediate layer can be formed.

The number of recording layers may be one or more, and the number of layers may be increased by stacking the recording layers with the intervention of the intermediate layer.

[Spacer Layer]

A concavo-convex geometry is provided in the guide layer and in turn, the reflected light on the guide layer has a frequency component and affects the recording/reproduction signal. Therefore, a spacer layer for spatially separating the guide layer from a recording layer closest to the guide layer and reducing the effect of reflected light on the guide layer can be provided.

The thickness of the spacer layer is from 5 to 100 μm, preferably from 10 to 50 μm, more preferably from 20 to 40 μm.

As the material for the spacer layer, a thermoplastic resin, a thermosetting resin, an ultraviolet-curable resin, an electron beam-curable resin, a self-adhesive agent and the like can be used. Also, the material may be the same material as the intermediate layer.

[Cover Layer]

From the standpoint of protecting the recording layer, a cover layer may be provided on the light incident surface side relative to the recording layer. If the cover layer is too thin, a surface scratch or contamination on the surface of the cover layer is detected with a good contrast. On the other hand, as the distance from the incident surface to the recording layer is increased, the aberration of the optical system becomes higher. Therefore, the thickness of the cover layer has a suitable range. Specifically, the thickness of the cover layer is generally from 0.01 to 0.2 mm, preferably from 0.02 to 0.1 mm, more preferably from 0.03 to 0.07 mm.

As the method to form the cover layer, for example, a method of forming an ultraviolet-curable resin composition on the surface and curing the composition, and a method of attaching the film through an adhesive, a self-adhesive agent or the like may be used.

The ultraviolet-curable resin is composed of a urethane resin, an acrylic resin, a urethane acrylate resin, an epoxy resin, a fluoropolymer such as perfluoropolyether, a silicon-based polymer such as polydimethylsiloxane, or a mixture with a photopolymerization initiator or the like.

As the photopolymerization initiator, a known initiator can be used, and out of the photopolymerization initiators, examples of the radical photoinitiator include Darocur 1173, Irgacure 651, Irgacure 184 and Irgacure 907 (all produced by Ciba Specialty Chemicals Corporation). The content of the photopolymerization initiator is, for example, approximately from 0.5 to 5 mass % in an ultraviolet-curable resin agent composition (as solid content).

Also, the composition may contain, if desired, a non-polymerizable diluting solvent, a photopolymerization initiation aid, an organic filler, a polymerization inhibitor, an antioxidant, an ultraviolet absorber, a light stabilizer, a defoaming agent, a leveling agent, a pigment, a silicon compound and the like. Examples of the non-polymerizable diluting solvent include isopropyl alcohol, n-butyl alcohol, methyl ethyl ketone, methyl isobutyl ketone, isopropyl acetate, n-butyl acetate, ethyl cellosolve, and toluene. Examples of the ultraviolet absorber include benzotriazole-based, benzophenone-based, oxalic acid anilide-based and cyano acrylate-based compounds.

Also, in the ultraviolet-curable composition, a thermal polymerization inhibitor, an antioxidant typified by hindered phenol, hindered amine and phosphite, a plasticizer, a silane coupling agent typified by epoxy silane, mercapto silane and (meth)acryl silane, and the like may be blended, if desired, as other additives for the purpose of improving various properties. For such an additive, those having excellent solubility for the curable component and not inhibiting the ultraviolet transmission are preferably selected and used.

This ultraviolet-curable resin may be used as an adhesive in the case of laminating a film.

As the self-adhesive agent used for the self-adhesive layer, for example, an acrylic, rubber-based or silicone-based self-adhesive agent can be used. In view of transparency and durability, an acrylic self-adhesive agent is preferred.

An acrylic copolymer obtained by copolymerizing, as a main monomer, a low Tg monomer such as butyl acrylate, ethyl acrylate and 2-ethylhexyl acrylate with a polyfunctional group monomer such as acrylic acid, methacrylic acid, hydroxyethyl methacrylate, hydroxyethyl acrylate, acrylamide and acrylonitrile is crosslinked, for example, by an isocyanate-based, melamine-based, epoxy-based or urethane-based crosslinking agent, whereby the acrylic self-adhesive agent can be obtained. Other photocurable oligomers•monomers, polymerization initiators, diluting solvents, tackifiers, antioxidants, sensitizers, crosslinking agents, ultraviolet absorbers, polymerization inhibitors, fillers, thermoplastic resins•dyes•pigments, and the like can be cured or added. Such a self-adhesive composition is coated on a separator.

As the separator, a release-treated plastic film or paper having a thickness of 25 to 100 µm, such as polyester film, polypropylene film, polyethylene film, polycarbonate film, polystyrene film and triacetyl cellulose film, can be used. Among these, a biaxially stretched polyester film is preferred, because a smoother surface is readily obtained and the productivity is excellent. The separator surface coming into contact with the self-adhesive agent layer is subjected to a treatment with a release agent. Examples of the release agent include a simple substance, a modification product, a mixture and the like of a silicone resin, a fluororesin, a polyvinyl alcohol resin and an alkyl group-containing resin. Among these, a silicone resin making it easy to lightly separate the adhesive layer may be preferably used, and in particular, a silicone resin cured with heat, ultraviolet ray, electron beam or the like may be more preferably used, because the silicone resin is less likely to transfer and adhere to the adhesive layer.

The self-adhesive layer can be coated on the separator by a known film-forming method. For example, air doctor coating, blade coating, rod coating, knife coating, squeeze coating, impregnation coating, reverse roll coating, transfer roll coating, gravure coating, kiss roll coating, cast coating, curtain coating, calender coating, extrusion coating, spray coating, spin coating, or hot-melt coating may be used. The composition coated is dried and cured, for example, by irradiation with an active energy ray to form a self-adhesive layer. Thereafter, a film material may be stacked on the self-adhesive layer by a laminator, whereby a cover layer with a self-adhesive layer can be formed.

In the case of laminating a film, the film used is not particularly limited as long as it is a transparent material, but a polycarbonate, an acrylic resin such as polymethyl methacrylate, a vinyl chloride-based resin such as polyvinyl chloride and vinyl chloride copolymer, an epoxy resin, an amorphous polyolefin, a polyester, and a cellulose triacetate are preferably used. Among these, a polycarbonate, an amorphous polyolefin or a cellulose triacetate are preferably used.

Here, the "transparent" means that the transmittance for light used in the recording and readout is 80% or more.

[Hardcoat Layer]

In order to prevent contact with an objective lens of the recording/reproducing apparatus, scratch due to handling, or contamination such as fingerprint, a hardcoat layer may be provided on the light incident surface. The hardcoat layer may be previously formed on the cover layer surface, or the layer may be prepared in the form of an ultraviolet-curable resin composition and, in the process of producing a disc, formed by coating the composition on the surface by spin coating or the like and then curing it.

The hardcoat layer is generally composed of a urethane resin, an acrylic resin, a urethane acrylate resin, an epoxy resin, a fluoropolymer such as perfluoropolyether, a silicon-based polymer such as polydimethylsiloxane, or a mixture with an $SiO_2$ fine particle, a photopolymerization initiator or the like.

As the photopolymerization initiator, a known initiator can be used, and out of the photopolymerization initiators, examples of the radical photoinitiator include Darocur 1173, Irgacure 651, Irgacure 184 and Irgacure 907 (all produced by Ciba Specialty Chemicals Corporation). The content of the photopolymerization initiator is, for example, approximately from 0.5 to 5 mass % in a hardcoat agent composition (as solid content).

Also, the hard coat agent composition may further contain, if desired, a non-polymerizable diluting solvent, a photopolymerization initiation aid, an organic filler, a polymerization inhibitor, an antioxidant, an ultraviolet absorber, a light stabilizer, a defoaming agent, a leveling agent, a pigment, a silicon compound and the like. Examples of the non-polymerizable diluting solvent include isopropyl alcohol, n-butyl alcohol, methyl ethyl ketone, methyl isobutyl ketone, isopropyl acetate, n-butyl acetate, ethyl cellosolve, and toluene. Examples of the ultraviolet absorber include benzotriazole-based, benzophenone-based, oxalic acid anilide-based and cyano acrylate-based compounds.

As the hardcoat material, specifically, the compounds described in JP-A-2004-292430 and JP-A-2005-112900, and commercially available products, for example, HC-3 (produced by DIC Corporation), may be also used.

The hardcoat layer may serve also as the above-described cover layer, and in this case, the layer can be formed by forming the hardcoat layer to a thickness necessary as the cover layer.

[Preparation of Recording Medium]

Respective constituent elements described above are combined as desired and sequentially stacked, whereby the optical information recording medium of the present invention can be manufactured.

The optical information recording medium of the present invention preferably has a recording layer composed of a non-resonant two-photon absorption recording material containing a non-resonant two-photon absorption compound and is more preferably an optical recording medium having a substrate, a guide layer, a reflecting layer, a spacer layer and a laminate structure consisting of a recording layer sandwiched by intermediate layers, in order, from the back side relative to incident light and a cover layer and a hardcoat layer on the incident light surface side.

Figure 2:
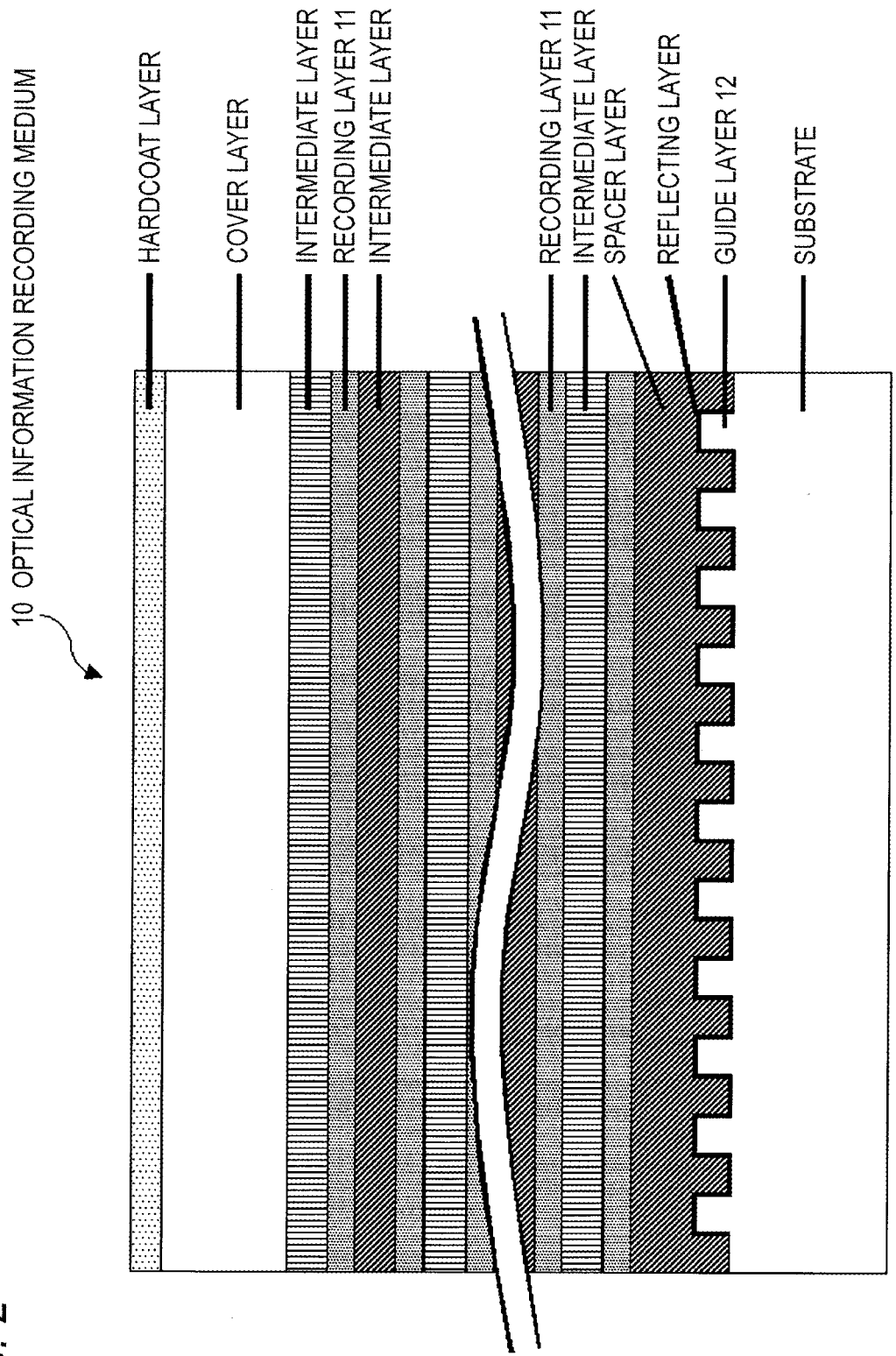
FIG. 2 is a view showing the outline of one example of the optical information recording medium using the two-photon absorption recording material of the present invention.

FIG. 2 shows one example of the optical information recording medium of the present invention. The optical information recording medium 10 shown in FIG. 2 has a guide layer 12, a reflecting layer, a spacer layer, an intermediate layer and a recording layer 11 in this order on a substrate. The recording layer has a configuration of being sandwiched by intermediate layers. Also, the medium has a cover layer and a hardcoat layer on the incident light surface side.

[Formation of Identification Information]

Marking by barcode or the like can be applied to a part of the medium for the purpose of providing identification information and the like on each recording medium.

As for the marking method, a method involving thermal fracture by delivering a laser beam into the reflecting layer used in the conventional optical disc described in Japanese Patent No. 3,143,454 and 3,385,285, and a method such as laser irradiation or printing of the recording layer may be used.

[Cartridge]

The recording medium may be housed in a cartridge for the purpose of protecting the recording medium from a scratch due to falling or handling or imparting light resistance. In this case, a cartridge used for the conventional optical disc can be utilized.

The configuration of the recording/reproducing apparatus is described below. As shown in FIG. 1, the recording/reproducing apparatus 1 is an apparatus performing recording•reproduction of information in an optical information recording medium 10 held by a spindle 50.

The recording/reproducing apparatus 1 has an objective lens 21 facing the optical information recording medium 10 and has, on the optical axis of the objective lens 21, DBS (dichroic beam splitter) 22, a λ/4 plate 23a, a beam expander 24 for correcting aberration, PBS (polarizing beam splitter) 25a, a λ/2 plate 26a, PBS 25b and a mirror 27 in order from the objective lens 21.

In the direction passing the mirror 27 and intersecting with the optical axis direction of the objective lens 21, a λ/2 plate 26b, a collimating lens 28, a pinhole 29, a condensing lens 30, a modulator 31, and a recording laser 32 are arranged in order.

Also, in the reflection direction of PBS 25b, a λ/2 plate 26c, a collimating lens 33, and a readout laser 34 are arranged in order, and in the reflection direction of PBS 25a, a beam splitter 35 is arranged. In one direction split by the beam splitter 35, a condensing lens 36, a pinhole 37, and a readout light receiving element 38 are arranged, and in another direction, a condensing lens 39, a cylindrical lens 40, and a readout focus light receiving element 41 are arranged.

In the direction passing DBS 22 and intersecting with the optical axis direction of the objective lens 21, a λ/4 plate 23b and PBS 25c are arranged. In the direction orthogonal to the optical axis direction of the objective lens 21 on one side of PBS 25c, a λ/2 plate 26 d, a collimating lens 42, and a laser light source 43 for the guide layer are arranged in order, and in the direction parallel to the optical axis direction of the objective lens 21 on another side of PBC 25c, a condensing lens 44, a cylindrical lens 45, and a light receiving element 46 for guide light are arranged in order.

The objective lens 21 is a lens converging the guide light on the guide layer and converging the recording light and the readout light on one of a plurality of recording layers 11. The objective lens 21 is moved in the optical axis direction by a lens actuator 47 that is driven by a control unit 60, to focus the guide light on the guide layer 12 and focus the recording light and the readout light on an arbitrary recording layer 11. Also, the objective lens 21 is moved in the direction parallel to the optical axis by the lens actuator 47, whereby the tracking position of the recording light and the reading light can be controlled.

The beam expander 24 is an optical element caused to change the converged or diverged state of light incident on the objective lens 21 by the control unit 60 and fulfills a function of correcting the depth and spherical aberration of the recording layer 11 undertaking the recording and reproduction.

The λ/4 plates 23a and 23b are an optical element for converting linearly polarized light into circularly polarized light and converting circularly polarized light into linearly polarized light in accordance with the rotational direction thereof and fulfills a function of making the direction of the linearly polarized light of light incident on the optical information recording medium 10 and the direction of the linearly polarized light of reflected light to differ by 90°.

Each of the λ/2 plates 26a, 26b, 26c and 26d is an optical element for rotating the polarizing direction of the linearly polarized light incident on the plate and can control the transmittance on passing the PBS by controlling the polarizing direction to the predetermined direction.

Each of PBS 25a and 25b is an optical element for reflecting and separating particular polarized light and fulfills a function of allowing the recording light emitted from the recording laser 32 and the reading light emitted from the readout laser 38 to pass through and travel toward the optical information recording medium 10 and at the same time, reflecting the readout light returned from the optical information recording medium 10 to cause its traveling toward the beam splitter 35.

Similarly, PBS 25c allows light from the laser light source 43 for the guide layer to pass through and travel toward the optical information recording medium 10 and reflects the reflected light to allow its travel toward the light receiving element 46 for guide light.

The beam splitter 35 is an optical element for splitting light in a predetermined splitting ratio irrespective of the polarization state of light and fulfills a function of distributing the readout light guided by the PBS 25a to the readout focus light receiving element 41 and the readout light receiving element 38.

DBS 22 is an optical element for reflecting light in a specific wavelength region and transmitting light in other wavelength regions, and a splitter capable of transmitting the recording light and readout light and reflecting the laser light for the guide layer is used. In this embodiment, this splitter is disposed to direct the laser light for the guide layer entering from the side toward the optical information recording medium 10.

The readout laser 34 is a 405 nm-CW (Continuous Wave) laser. The beam of the readout laser 34 is preferably narrowed to be equal to or smaller than the recording spot and therefore, it is preferred to use a laser capable of emitting light having a wavelength the same as or shorter than that of the recording laser 32. The output of the readout laser 34 is controlled by the control unit 60.

The laser 43 for the guide layer is a 650 nm-CW laser. The light from the laser 43 for the guide layer is collected by the objective lens 21 and concentrated on the guide layer 12 of the optical information recording medium 10. The laser light for the guide layer can be split by DBS 22 by making the recording light and the readout light to differ from each other. The output of the laser 43 for the guide layer is controlled by the control unit 60.

The recording laser 32 is a 405 nm-pulsed laser. To efficiently cause a multi-photon absorption reaction in the recording layer 11, a pulsed laser having a peak power greater than that of the CW laser is preferably used as the recording laser 32. The output of the recording laser 32 is controlled by the control unit 60. The peak power preferred as the recording laser is preferably from 1 to 100 W on the surface of the optical information recording medium 10. If the peak power is less than 1 W, the photon density in the recording spot is reduced to cause a problem that an efficient multi-photon absorption reaction does not occur, whereas if the peak power exceeds 100 W e, the average output of the recording layer becomes high and there arises a problem that the recording pulsed laser used for recording becomes large-sized. Therefore, the average output of the recording laser is preferably 100 mW or less on the optical information recording medium. The average output of the pulsed laser is determined by the product of the peak power, the pulse width and the oscillation cycle. The preferred peak power is from 1 to 100 W and therefore, for achieving an average power of 100 mW or less, the product of the pulse width and the oscillation cycle is preferably from 0.001 to 0.1. The pulse oscillation cycle preferred as the recording laser is preferably 50 MHz or more so as to ensure a sufficient recording speed. When a more preferred oscillation cycle of 500 MHz is selected as the sufficient oscillation cycle, the pulse width at a peak power of 1 to 100 W may be selected in the range of 200 psec to 2 psec or less, respectively, so as to give an average power of 100 mW or less.

The modulator 31 is a device for removing a part of the pulsed light out of the pulsed laser light emitted from the recording laser 32 to temporally modulate the pulsed laser light and encode the information. As the modulator 42, an acousto-optic modulator (AOM), a Mach-Zehnder (MZ) optical modulator, and other electro-optic modulators (EOM) may be used. When such an acousto-optic modulator or electro-optic modulator is used as the modulator 31, ON•OFF of light can be performed at an extremely high speed as compared with using a mechanical shutter. The control unit 60 outputs, to the modulator 31, the signal encoded in accordance with the information to be recorded, whereby the operation of the modulator 31 is controlled.

Each of the light receiving elements 46 and 41 for guide light utilizes a quadrant photodetector or the like and is an element for obtaining a focus controlling signal by an astigmatic method or the like. Specifically, the control unit 60 controls the beam expander 24 or the lens actuator 47 to minimize astigmatism generated by passing through the condensing lenses 39 and 44 and the cylindrical lenses 40 and 45, whereby focusing can be performed The readout light receiving element 38 is an element for receiving the readout light including the reproduced information, and the signal detected by the readout light receiving element 38 is output to the control unit 60 and then demodulated into the information in the control unit 60. The light received by the readout focus light receiving element 41 has passed through the cylindrical lens 40, so that when the light quantity distribution is output to the control unit 60, the control amount for the focusing servo of the recording light and the readout light can be obtained by an astigmatic method in the control unit 60.

The pinhole plate 37 is arranged in the vicinity of the focal point of light condensed by the condensing lens 36 and constitutes a confocal optical system, whereby unnecessary light can be cut by passing only the reflected light from a predetermined depth position of the optical information recording medium 10.

The control unit 60 controls the lens actuator 47 by the astigmatism of laser light for the guide layer detected by the guide light receiving element 46 and controls the position in the optical axis direction of the objective lens 21 to adjust the focal position of the guide light to a position on the guide layer. Also, the unit controls the lens actuator 21 by a push-pull method (DPP method) using a differential signal detected by the guide light receiving element 46 or a differential phase detection (DPD Method) using a differential phase signal to control the position in the direction orthogonal to the optical axis of the objective lens 21 and adjust the tracking position. Furthermore, the unit controls the beam expander 24 by astigmatism of the readout light detected by the readout focus light receiving element 38 and thereby controls the focal position of the recording/readout light to focus on a predetermined recording layer 11.

The recording/reproducing apparatus 1 has the same configuration of the conventionally known optical recording/regenerating apparatus, in addition to the above-described configuration. For example, the apparatus has an actuator for moving the recording light, the readout light and the optical information recording medium 10 relatively to each other in the planar direction of the recording layer 11 so as to record many recording spots in the plane of the recording layer 11 of the optical information recording medium 10.

The recording/reproducing method by the thus-configured recording/reproducing apparatus 1 is described below.

At the recording of information, in the recording/reproducing apparatus 1, pulsed laser light is emitted from the recording laser 32, and information is encoded on the pulsed laser light by removing a part of the pulsed light by the modulator 31. The information-encoded light passes PBS 25b, the λ/2 plate 26a and PBS 25a, converged by the beam expander 24 to control the diverged state, then passes the λ/4 plate 23a and DBS 22, and converged on a predetermined recording layer 11 by the objective lens 21. At the same time with irradiation with the pulsed laser light, the readout laser 34 emits CW laser light, and the CW laser light is reflected by PBS 25b and then converged by the objective lens 21, similarly to the recording laser light. The CW laser light returned from the optical information recording medium 10 passes the objective lens 21, DBS 22, the λ/4 plate 23a and the beam expander 24, is reflected by PBS 25a, and enters the readout light receiving element 38 through the condensing lens 36 and the pinhole plate 37.

The control unit 60 calculates focal positions of the guide light, the recording beam and the readout light based on the signal received from the guide light receiving element 46 and the readout focus light receiving element 41 and drives the lens actuator 21 and the beam expander 24, thereby controlling the position of the objective lens and controlling the recording light and readout light to focus on a predetermined recording layer 11.

As a result, according to the intensity of light (in the case of a two-photon absorption reaction, in proportion to the square of the intensity of light), a light absorption reaction occurs more frequently in the closer vicinity to the focal point where the intensity of the light is strong, and the recording layer is changed in accordance with this reaction.

At the readout of information, the apparatus stops the recording laser 32 and drives the readout laser 34 to irradiate the optical information recording medium 10 with CW laser light. At this time, similarly to the recording of information, the CW laser light (readout light) returned from the optical information recording medium 10 is reflected by the PBS 25a and enters the readout light receiving element 38 and the readout focus light receiving element 41.

In this way, the control unit 60 can demodulate the information from the modulation obtained by the difference between the intensity of reflected light in the recorded portion and the intensity of reflected light in the non-recorded portion. That is, the information can be read out.

In the foregoing pages, the embodiment of the present invention is described, but the present invention is not limited to the embodiment described above and can be implemented by making appropriate modification therein.

Material Capable of Changing Intensity of Reflected Light Between Before and After Two-Photon Recording The material capable of changing the intensity of reflected light between before and after two-photon recording, which is used in the non-resonant two-photon absorption recording material of the present invention, includes, for example, a polymer compound encompassing the polymer two-photon absorption compound of the present invention.

The polymer compound is preferably a compound having no linear absorption at the two-photon recording wavelength.

As for the polymer compound, the same compounds as those described above as the binder in the two-photon absorption recording material may be also appropriately used.

EXAMPLES

Specific Examples of the present invention are described below based on the experimental results. Of course, the present invention is not limited to these Examples.

Example 1

Synthesis Method of Compound D-1

Compound D-1 was synthesized by the following method.

[Chem. 53]

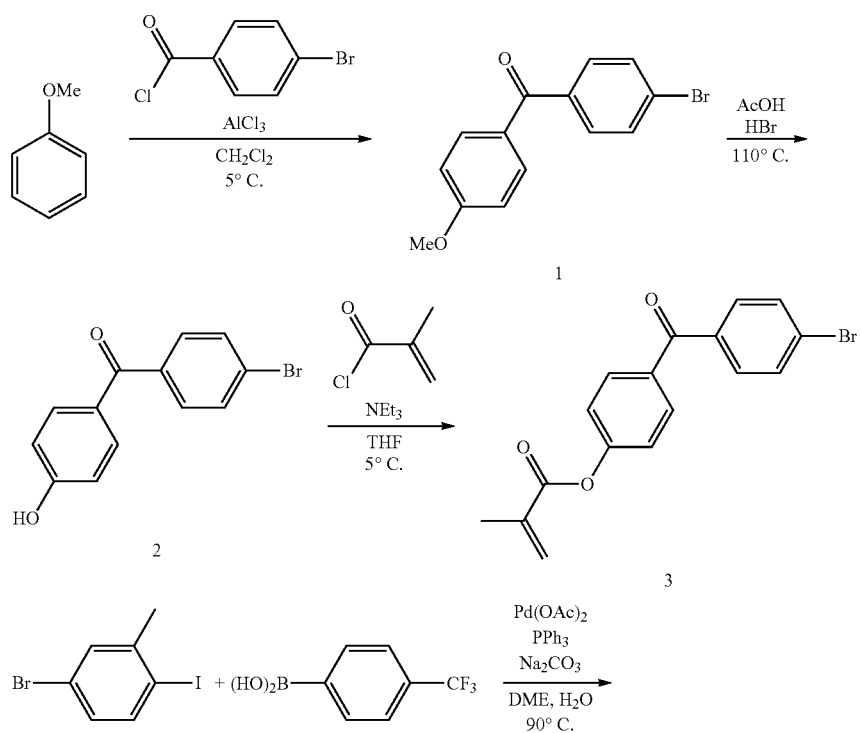

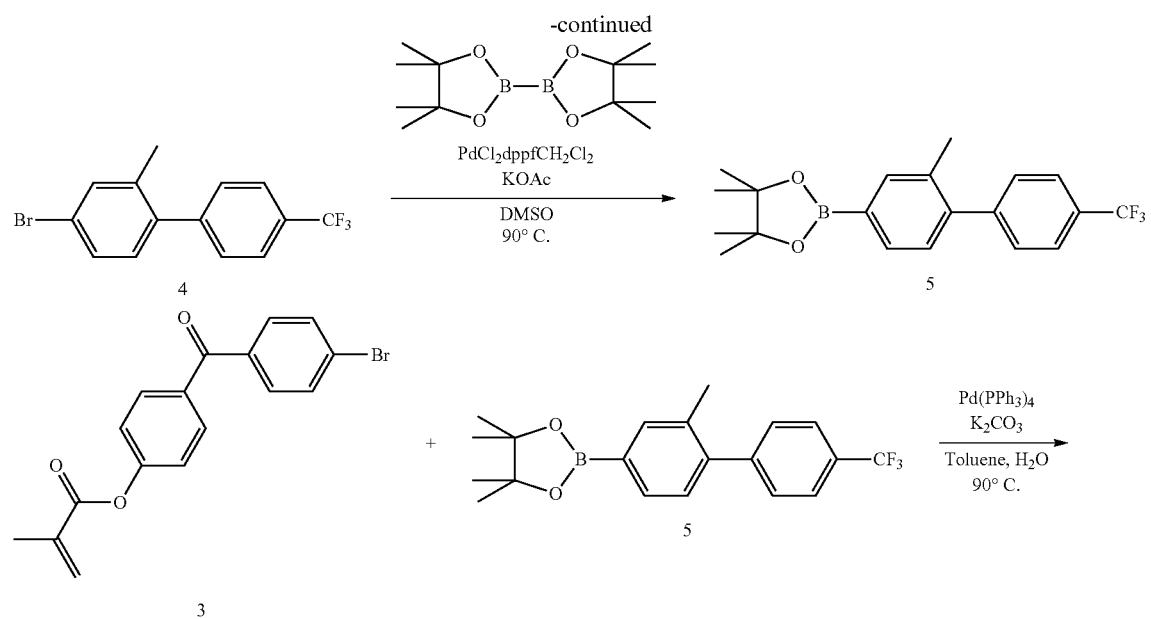
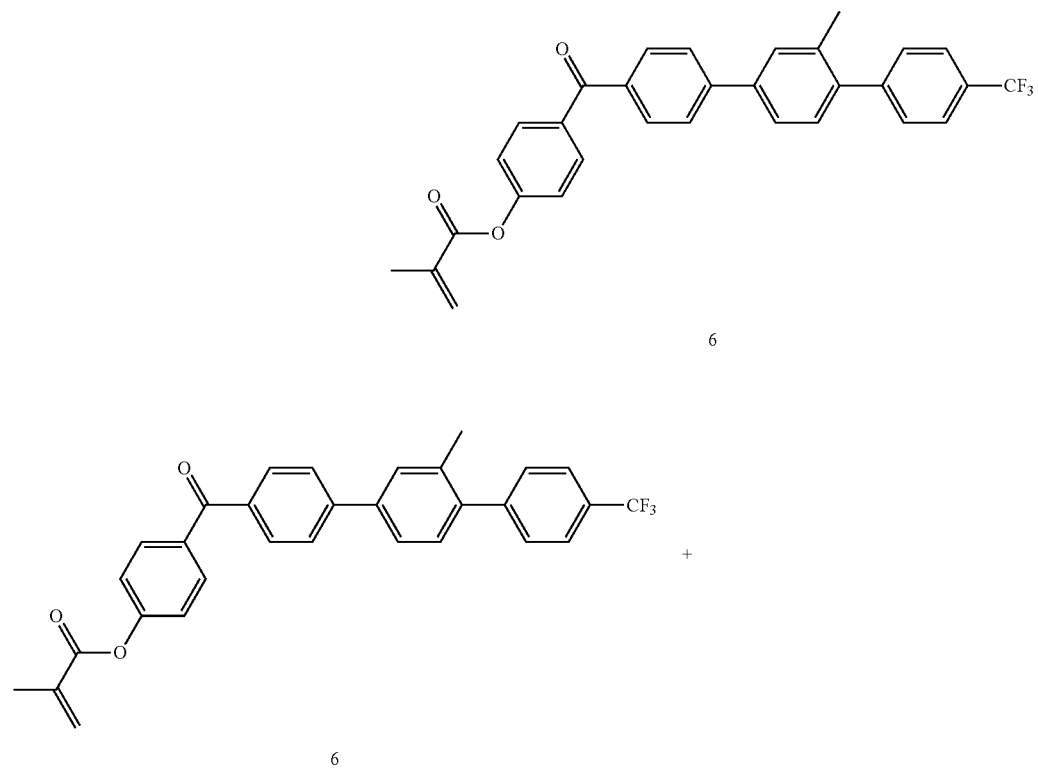
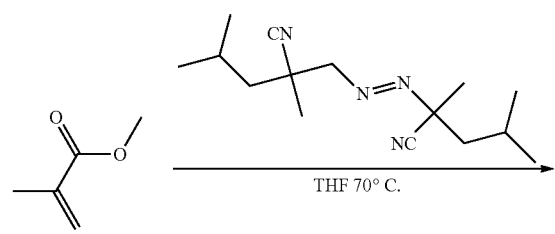

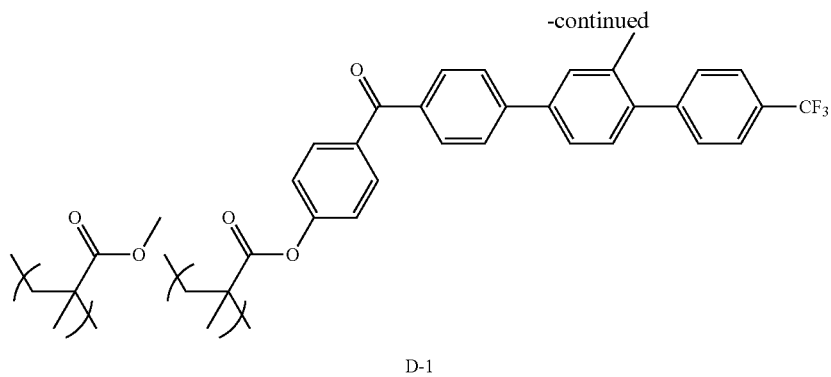

D-1

Synthesis of Raw Material Compound 1

27.0 g (250 mmol) of anisole and 42.9 g (200 mmol) of 4-bromobenzoyl chloride were dissolved in 500 ml of methylene chloride, and after cooling to an internal temperature of 5° C., 33.4 g (250 mmol) of aluminum chloride were added in 6 parts, followed by stirring for 8 hours in a nitrogen atmosphere. The reaction solution was poured in water, then extracted with methylene chloride, and evaporated to dryness in a rotary evaporator to quantitatively obtain white Compound 2. Compound 1 obtained was confirmed to be the target product by $^1$H NMR.

Synthesis of Raw Material Compound 2

140 ml of hydrobromic acid and 220 ml of acetic acid were added to 35.0 g (120 mmol) of Raw Material Compound 1, and the mixture was stirred at an internal temperature of 110° C. for 12 hours and a half. After allowing to cool to room temperature, the reaction solution was poured in water and stirred at room temperature for 20 minutes. The precipitate was filtered, then washed with pure water and hexane: ethyl acetate=5:1 and dried under reduced pressure to quantitatively obtain white Compound 3. Compound 2 obtained was confirmed to be the target product by $^1$H NMR.

Synthesis of Raw Material Compound 3

9.74 g (35.1 mmol) of Raw Material Compound 2 was dissolved in 70 ml of tetrahydrofuran and after adding 7.10 g (70.2 mmol) of triethylamine, the mixture was cooled to an internal temperature of 5° C. Thereafter, the system was stirred for 2 hours in a nitrogen atmosphere while adding dropwise 3.67 g (35.1 mmol) of methacrylic acid chloride. The reaction solution was poured in water and stirred at room temperature for 20 minutes. The precipitate deposited was separated by filtration and dried at room temperature to quantitatively obtain white Compound 3. Compound 3 obtained was confirmed to be the target product by $^1$H NMR.

Synthesis of Raw Material Compound 4

350 ml of 1,2-dimethoxyethane and 70 ml of water were added to 63.5 g (214 mmol) of 5-bromo-2-iodotoluene, 44.7 g (235 mmol) of para-trifluoromethylphenylboronic acid, 2.40 g (10.7 mmol) of palladium acetate and 68.0 g (642 mmol) of sodium carbonate, and the mixture was stirred at an external temperature of 90° C. for 72 hours in a nitrogen atmosphere. After allowing to cool to room temperature, the reaction solution was extracted with ethyl acetate, concentrated in a rotary evaporator and purified on a silica gel column (hexane) to obtain 57.9 g (yield: 86%) of white Compound 4. Compound 4 obtained was confirmed to be the target product by $^1$H NMR.

Synthesis of Raw Material Compound 5

400 ml of dimethylsulfoxide was added to 57.9 g (184 mmol) of Raw Material Compound 4, 56.1 g (221 mmol) of bispinacolatodiboron, 4.25 g (5.20 mmol) of [1, r-bis(diphenylphosphino)ferrocene]palladium(II) dichloride dichloromethane adduct and 54.2 g (552 mmol) of potassium acetate, and the mixture was stirred at an internal temperature of 90° C. for 5 hours in a nitrogen atmosphere. After allowing to cool to room temperature, the reaction solution was extracted with ethyl acetate, concentrated in a rotary evaporator and then purified on a silica gel column (hexane: ethyl acetate=10:1) to obtain 57.5 g (yield: 86%) of white Compound 5. Compound 5 obtained was confirmed to be the target product by $^1$H NMR.

Synthesis of Raw Material Compound 6

170 ml of toluene and 20 ml of water were added to 14.8 g (42.9 mmol) of Raw Material Compound 3, 18.6 g (51.5 mmol) of Raw Material Compound 5, 2.48 g (2.15 mmol) of tetrakistriphenylphosphine palladium, 17.8 g (129 mmol) of potassium carbonate and 1 mg of dibutylhydroxytoluene, and the mixture was stirred at an external temperature of 90° C. for 12 hours in a nitrogen atmosphere. After allowing to cool to room temperature, the reaction solution was extracted with ethyl acetate, concentrated in a rotary evaporator, purified on a silica gel column (ethyl acetate: hexane=1:5), recrystallized from ethyl acetate/hexane, separated by filtration and dried to obtain 6.8 g (yield: 32%) of white Compound 6. Compound 6 obtained was confirmed to be the target product by $^1$H NMR.

$^1$H NMR (CDCl3) 7.92 (d, 4H), 7.76 (dd, 2H), 7.71 (d, 2H), 7.59-7.55 (m, 2H), 7.50 (d, 2H), 7.34 (d, 1H), 7.29 (dd, 2H), 6.41 (s, 1H), 5.82 (t, 111), 2.37 (s, 3H).

Synthesis of D-1

5 g of tetrahydrofuran was stirred at an external temperature of 70° C. in a nitrogen atmosphere. Thereto, 2.00 g (4.00 mmol) of Raw Material Compound 6 dissolved in 26.7 g of tetrahydrofuran, 11.6 g (116 mmol) of methyl methacrylate and 29.8 mg (0.12 mmol) of 2,2'-azobis(2,4-dimethylvaleronitrile) were added dropwise over 2 hours, followed by stirring for 8 hours. After allowing to cool to room temperature, the reaction solution was diluted with acetone, recrystallized from acetone/hexane, separated by filtration and dried to obtain 4.77 g of Compound D-1. The composition of the polymer obtained was confirmed by $^1$H NMR, and the molecular weight was measured by GPC (compositional ratio: Raw Material Compound 6/methyl methacrylate=12/88 (by mol), Mw=367,000).

Synthesis of D-3

3.99 g of methyl ethyl ketone was stirred at an external temperature of 70° C. in a nitrogen atmosphere. Thereto, 1.88 g (3.76 mmol) of Raw Material Compound 6 dissolved in 35.9 g of methyl ethyl ketone, 5.15 g (36.2 mmol) of butyl methacrylate and 49.7 mg (0.20 mmol) of 2,2'-azobis(2,4-dimethylvaleronitrile) were added dropwise over 3 hours, followed by stirring for 4 hours. After allowing to cool to room temperature, the reaction solution was diluted with acetone, recrystallized from water/methanol, separated by filtration and dried to obtain Compound D-3. The composition of the polymer obtained was confirmed by $^1$H NMR, and the molecular weight was measured by GPC (compositional ratio: Raw Material Compound 6/butyl methacrylate=13.5/86.5 (by mol), Mw=32,000).

Example 2

Synthesis of Comparative Compound R-1

[Chem. 54]

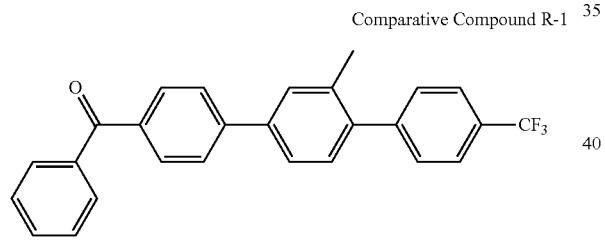

Comparative Compound R-1

Synthesis of Comparative Compound R-1

Compound R-1 was synthesized by the following method.

[Chem. 55]

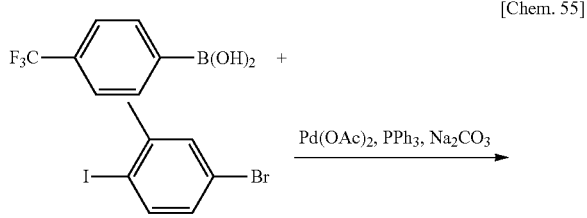

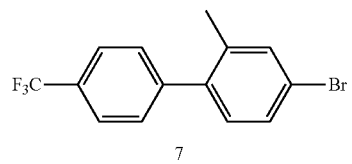

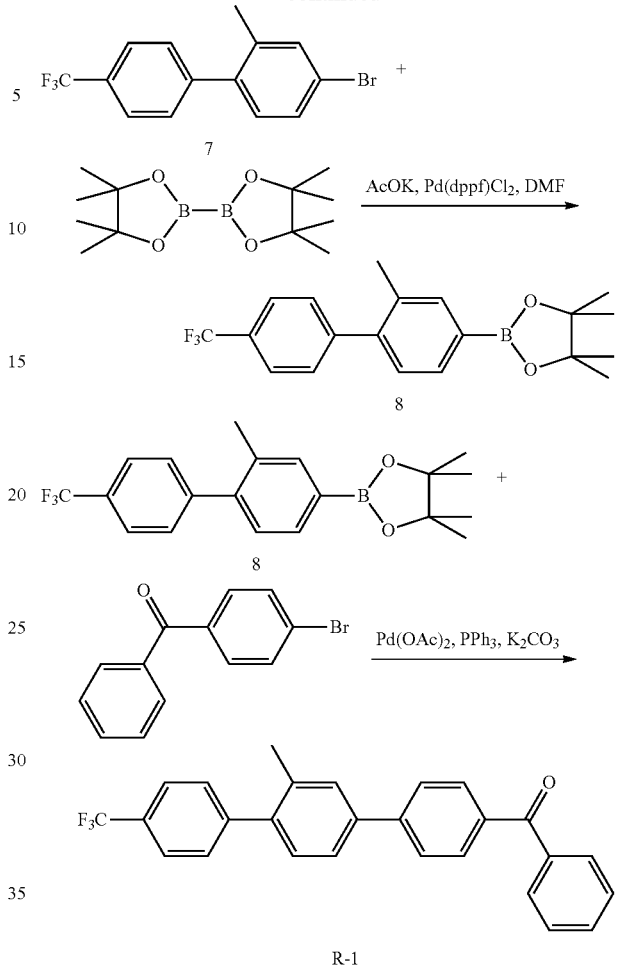

Synthesis of Raw Material Compound 7

6.98 g (37 mmol) of p-trifluoromethylphenylboronic acid, 9.92 g (33 mmol) 5-bromo-2-iodotoluene and 10.6 g (100 mmol) of sodium carbonate were dissolved in 190 ml of ethylene glycol dimethyl ether-distilled water mixed solvent (14:5), and 0.37 g (1.7 mmol) of palladium acetate and 0.88 g (3.3 mmol) of triphenylphosphine were added thereto. The system was heated for 7 hours in a nitrogen flow, and the reaction solution was allowed to cool and extracted by adding distilled water and about 600 ml of ethyl acetate. The aqueous layer was removed to separate the organic layer, and this organic phase was dried over magnesium sulfate. The filtrate after separating magnesium sulfate by filtration was evaporated to dryness in a rotary evaporator and purified on a silica gel column (ethyl acetate: hexane=1:400) to obtain 10.1 g (yield: 96%) of white Raw Material Compound 7. Compound 7 obtained was confirmed to be the target compound by $^1$H NMR spectrum.

Synthesis of Raw Material Compound 8

9.5 g (30 mmol) of Raw Material Compound 7, 9.9 g (39 mmol) of bis(pinacolato)diboron, 8.8 g (90 mmol) of potassium acetate and 0.73 g (0.9 mmol) of [1,1'-bis(diphenylphosphino)ferrocene]dichloropalladium were suspended in 170 ml of DMF, and the system was heated at 80° C. for 4 hours in a nitrogen flow. The reaction solution was allowed to cool and extracted by adding distilled water and ethyl acetate, and the aqueous layer was removed to separate the organic layer. This organic phase was dried over magnesium sulfate, and the filtrate after separating magnesium sulfate by filtration was evaporated to dryness in a rotary evaporator and purified on a silica gel column (ethyl acetate: hexane=1:100→1:10) to obtain 5.9 g (yield: 54%) of colorless Raw Material Compound 8. Compound 8 obtained was confirmed to be the target compound by $^1$H NMR spectrum.

Synthesis of R-1

0.8 g (2.2 mmol) of Raw Material Compound 5 and 0.52 g (2.0 mmol) of p-bromobenzophenone were dissolved in 35 mL of ethylene glycol dimethyl ether-distilled water mixed solvent (6:1), and 22.5 mg (0.1 mmol) of palladium acetate, 52.4 mg (0.2 mmol) of triphenylphosphine and 0.64 g (6 mmol) of potassium carbonate were added thereto. The mixture was refluxed under heating for 2 hour, and the reaction solution was allowed to cool and extracted by adding distilled water and ethyl acetate. The aqueous layer was removed to separate the organic layer, and this organic phase was dried over magnesium sulfate. The filtrate after separating magnesium sulfate by filtration was evaporated to dryness in a rotary evaporator to obtain a crude product, and the crude product was purified on a silica gel column (ethyl acetate: hexane=1:100→1:5) to obtain 0.71 g (yield: 77%) of a white crystal. The compound obtained was confirmed to be the target Compound R-1 by mass spectrum and $^1$H NMR spectrum.

$^1$H NMR (CDCl$_3$) 2.37 (s, 3H), 7.34 (d, 1H), 7.48-7.55 (m, 7H), 7.7-7.8 (m, 4H), 7.85 (m, 2H), 7.95 (m, 2H)

Preparation of Two-Photon Recording Material

Preparation of Two-Photon Recording Material 1

Two-Photon Recording Material 1 was prepared according to the following formulation.

| | |
|---|---|
| Polymer two-photon absorption compound: D-1 | 7 parts by mass |
| Coating solvent: methyl ethyl ketone | 93 parts by mass |

Preparation of Two-Photon Recording Material 2

Two-Photon Recording Material 2 using R-1 in place of D-1 as the two-photon absorption compound and using methyl polymethacrylate was prepared.

| | |
|---|---|
| Two-photon absorption compound: R-1 | 3 parts by mass |
| Binder: methyl polymethacrylate (produced by Aldrich, Mw = 100,000) | 6 parts by mass |
| Coating solvent: methyl ethyl ketone | 91 parts by mass |

Production of Two-Photon Absorption Recording Mediums 5 and 6

Using a slide glass as the substrate, each of coating solutions of Two-Photon Absorption Recording Materials 1 and 2 prepared above was coated thereon by spin coating to form a recording layer. At this time, the rotation speed was adjusted in the range of 300 to 3,000 rpm such that the recording layer has a thickness of 1 µm. As the cover layer, a polycarbonate film (Teijin Pure-Ace, thickness: 80 µm) having a self-adhesive layer (glass transition temperature: −52° C.) on one surface was used, and the self-adhesive layer and the polycarbonate film were set to have a total thickness of 100 µm. The cover layer was placed on the recording layer through the self-adhesive layer, and these layers were laminated together by press-bonding the cover layer by means of a pressing member, whereby Two-Photon Absorption Recording Mediums 5 and 6 composed of one recording layer were produced.

Evaluation of Two-Photon Recording/Reproduction

For the two-photon recording, a pico-second laser of 405 nm (pulse width: 2 ps, repetition: 76 MHz, peak power 66 W (average power: 5 mW)) was used. Readout of the recording signal was performed by reading the signal of reflected light at the irradiation with semiconductor laser light of 405 nm.

Evaluation of Change in Height of Recording Mark by Humidity-Heat Storage Test after Two-Photon Recording With respect to the recorded part in the recording layer using each of Two-Photon Absorption Recording Mediums 5 and 6 after two-photon absorption recording, a humidity-heat storage test at 60° C. and 90% RH was performed, as a result, the recording mark of Two-Photon Absorption Recording Material 2 disappeared in 2 hours. On the other hand, reduction in the height of the recording mark of Two-Photon Absorption Recording Material 1 stayed at 10% after 300 hours.

Evaluation of Change in Intensity of Reflected Light by Humidity-Heat Storage Test of Unrecorded Part With respect to the unrecorded part in the recording layer using each of Two-Photon Absorption Recording Materials 1 and 2 after two-photon absorption recording, a humidity-heat storage test for 300 hours was performed. Assuming that the intensity of each reflected light before the test is 100, the relative change in the intensity of reflected light between before and after the test is shown in Table 1 below.

[Table 1]

TABLE 1

Evaluation by Humidity-Heat Storage Test of Two-Photon Absorption Recording Medium

| | | Relative Change in Intensity of Reflected Light | |
|---|---|---|---|
| Recording Medium | Humidity-Heat Storage Conditions | Before Test | After Test of 300 Hours |
| Two-Photon Absorption Recording Medium 5 | 60° C., 90% RH | 100 | 89 |
| | 80° C., 85% RH | 100 | 110 |
| Two-Photon Absorption Recording Medium 6 | 60° C., 90% RH | 100 | 56 |
| | 80° C., 85% RH | 100 | 59 |

As seen in Table 1, the two-photon absorption recording material using Compound D-1 of the present invention has higher humidity-heat resistance than the two-photon absorption recording material using Comparative Compound R-1.

Example 3
Synthesis Method of Compound D-21
Compound D-21 was synthesized by the following method.
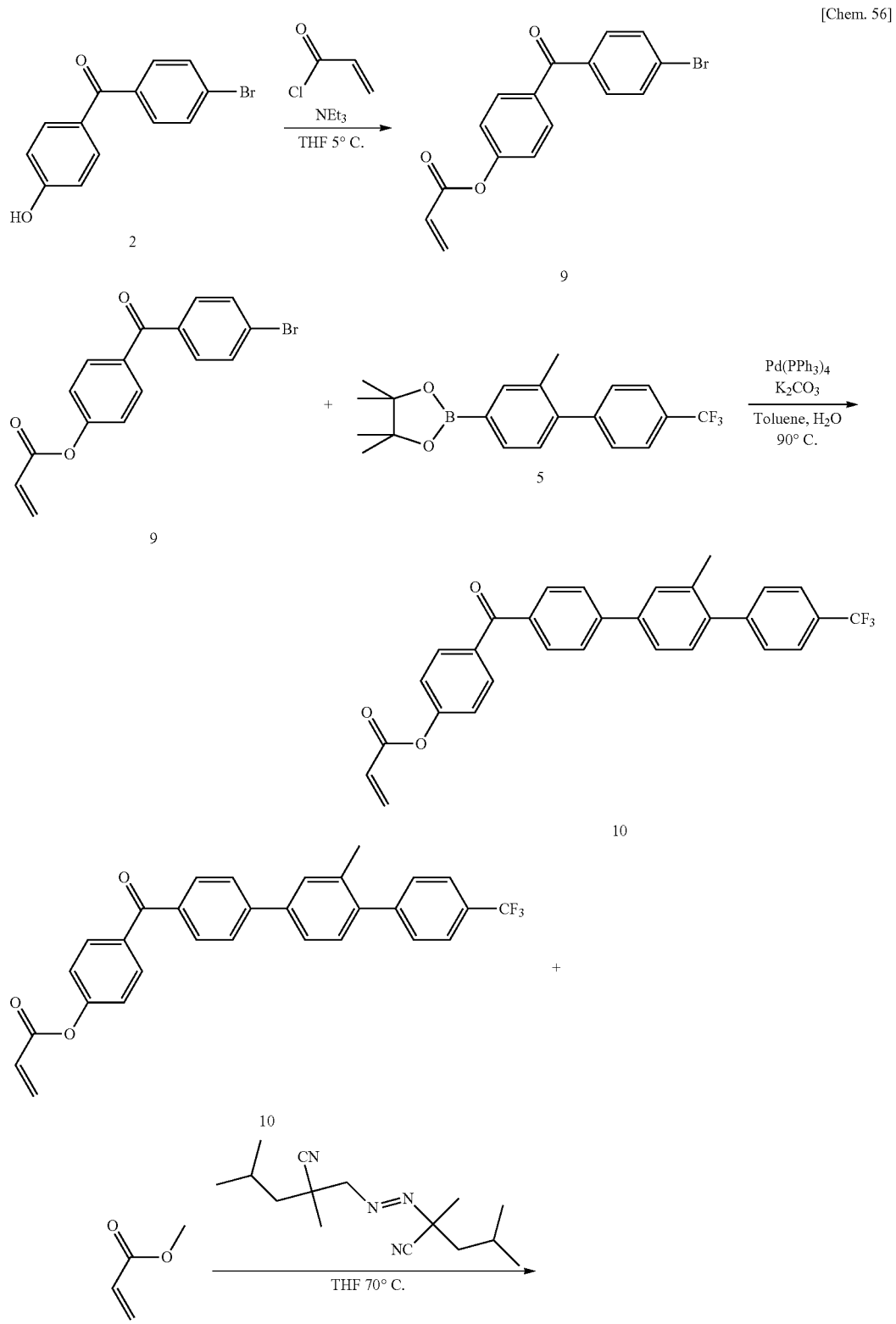
[Chem. 56]

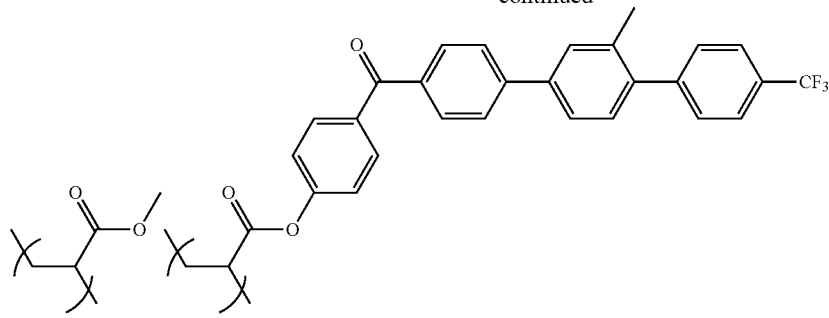

D-21

Synthesis of Raw Material Compound 9

9.74 g (35.1 mmol) of Raw Material Compound 2 was dissolved in 70 ml of tetrahydrofuran and after adding 7.10 g (70.2 mmol) of triethylamine, the mixture was cooled to an internal temperature of 5° C. Thereafter, the system was stirred for 2 hours in a nitrogen atmosphere while adding dropwise 3.18 g (35.1 mmol) of methacrylic acid chloride. The reaction solution was poured in water and stirred at room temperature for 20 minutes. The precipitate deposited was separated by filtration and dried at room temperature to quantitatively obtain white Compound 9. Compound 9 obtained was confirmed to be the target product by $^1$H NMR.

Synthesis of Raw Material Compound 10

170 ml of toluene and 20 ml of water were added to 14.2 g (42.9 mmol) of Raw Material Compound 9, 18.6 g (51.5 mmol) of raw material Compound 5, 2.48 g (2.15 mmol) of tetrakistriphenylphosphine palladium, 17.8 g (129 mmol) of potassium carbonate and 1 mg of dibutylhydroxytoluene, and the mixture was stirred at an external temperature of 90° C. for 12 hours in a nitrogen atmosphere. After allowing to cool to room temperature, the reaction solution was extracted with ethyl acetate, concentrated in a rotary evaporator and purified on a silica gel column (ethyl acetate: hexane=1:5) to obtain 6.8 g (yield: 32%) of white Compound 10. Compound 10 obtained was confirmed to be the target product by $^1$H NMR.

Synthesis of D-21

5 g of tetrahydrofuran was stirred at an external temperature of 70° C. in a nitrogen atmosphere. Thereto, 1.95 g (4.00 mmol) of Raw Material Compound 10 dissolved in 26.7 g of tetrahydrofuran, 9.98 g (116 mmol) of methyl methacrylate and 29.8 mg (0.12 mmol) of 2,2'-azobis(2,4-dimethylvaleronitrile) were added dropwise over 2 hours, followed by stirring for 8 hours. After allowing to cool to room temperature, the reaction solution was diluted with acetone, recrystallized from acetone/hexane, separated by filtration and dried to obtain 4.33 g of Compound D-21. The composition of the polymer obtained was confirmed by $^1$H NMR, and the molecular weight was measured by GPC (compositional ratio: Raw Material Compound 10/methyl methacrylate=10/90 (by mol), Mw=34,000).

Production of Two-Photon Absorption Recording Mediums 7 and 8

Based on the preparation method for Two-Photon Absorption Recording Medium 5, Two-Photon Absorption Recording Medium 7 was prepared using Polymer Two-Photon Absorption Compound D-21 synthesized in the same manner as D-1, and Two-Photon Absorption Recording Medium 8 was prepared using R-1 and polymethyl acrylate, similarly to Two-Photon Absorption Recording Medium 6.

Evaluation of Change in Height of Recording Mark by Humidity-Heat Storage Test after Two-Photon Recording With respect to the recorded part in the recording layer using each of Two-Photon Absorption Recording Mediums 7 and 8 after two-photon absorption recording, a humidity-heat storage test at 60° C. and 90% RH was performed, as a result, the recording mark of Two-Photon Absorption Recording Material 8 using R-1 disappeared in 2 hours. On the other hand, reduction in the height of the recording mark of Two-Photon Absorption Recording Material 7 using D-21 stayed at 14% after 300 hours.

Evaluation of Change in Intensity of Reflected Light by Humidity-Heat Storage Test of Unrecorded Part With respect to the unrecorded part in the recording layer using each of Two-Photon Absorption Recording Mediums 7 and 8 after two-photon absorption recording, a humidity-heat storage test for 300 hours was performed. Assuming that the intensity of each reflected light before the test is 100, the relative change in the intensity of reflected light between before and after the test is shown in Table 2 below.
[Table 2]

TABLE 2

Evaluation by Humidity-Heat Storage Test of Two-Photon Absorption Recording Medium

| Recording Medium | Humidity-Heat Storage Conditions | Relative Change in Intensity of Reflected Light | |
|---|---|---|---|
| | | Before Test | After Test of 300 Hours |
| Two-Photon Absorption Recording Medium 7 | 60° C., 90% RH<br>80° C., 85% RH | 100<br>100 | 76<br>69 |
| Two-Photon Absorption Recording Medium 8 | 60° C., 90% RH<br>80° C., 85% RH | 100<br>100 | 24<br>18 |

As seen from the evaluation of change in mark height and the results in Table 2, Two-Photon Absorption Recording Material 7 using Compound D-21 of the present invention has higher humidity-heat resistance than Two-Photon Absorption Recording Material 8 using Comparative Compound R-1.

Example 4
Synthesis Method of Compound D-77
Compound D-77 was synthesized by the following method.
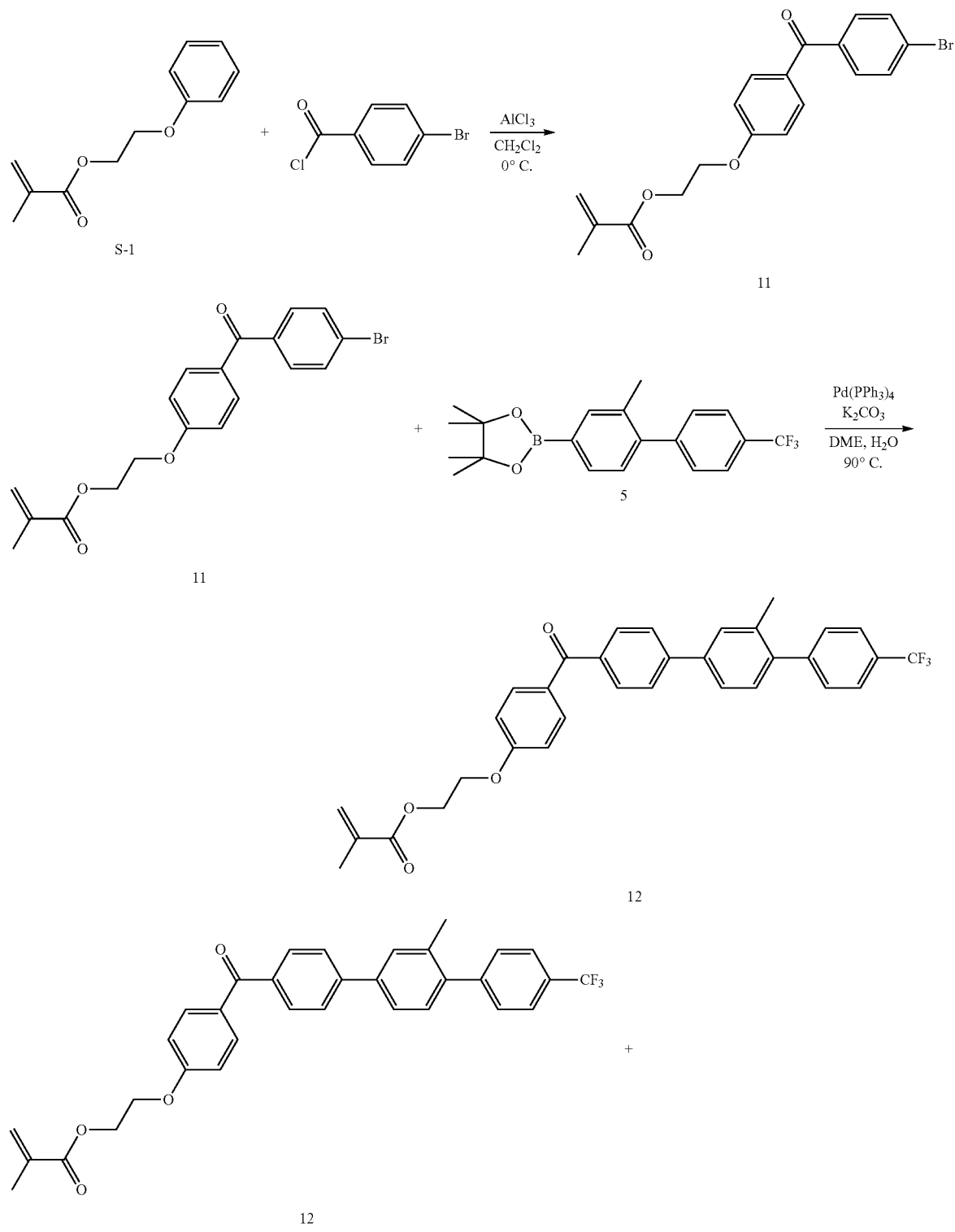
[Chem. 57]

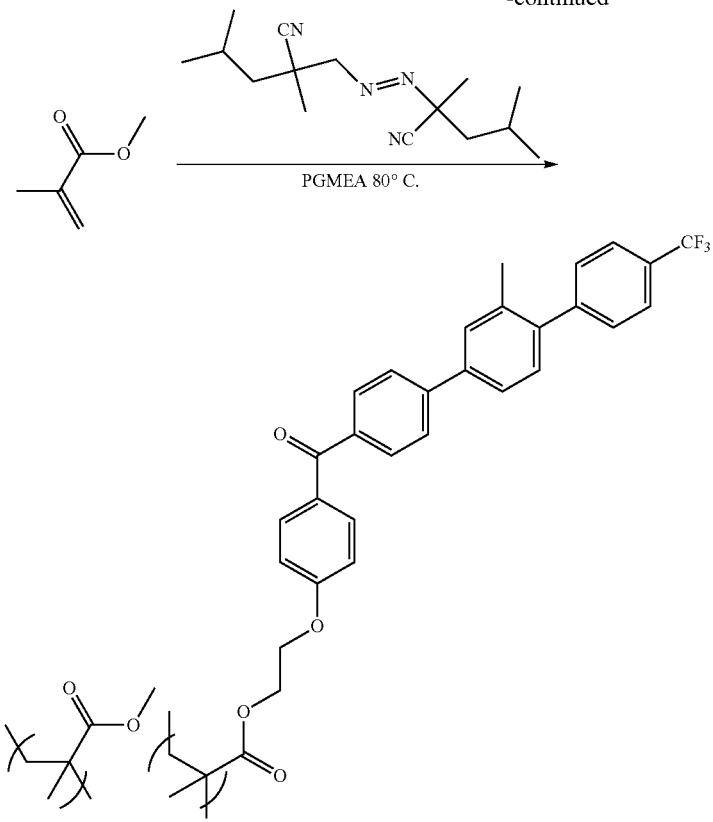

D-77

Synthesis of Raw Material Compound 11

100 ml of methylene chloride was added to 11.0 g (25.0 mmol) of 4-bromobenzoyl chloride and 8.34 g (31.3 mmol) of aluminum chloride, and the mixture was stirred at an external temperature of 0° C. under ice bath in a nitrogen atmosphere. Thereto, 12.9 g (31.3 mmol) of Raw Material Compound S-1 was added dropwise over 30 minutes, and the system was stirred for 2 hours. The reaction solution was added dropwise to 200 ml of ice water, extracted with ethyl acetate and concentrated in a rotary evaporator to obtain 8.53 g (yield: 70%) of white Compound 11. Compound 11 obtained was confirmed to be the target product by $^1$H NMR.

Synthesis of Raw Material Compound 12

35 ml of dimethoxyethane and 7 ml of water were added to 2.74 g (7.04 mmol) of Raw Material Compound 11, 2.80 g (7.73 mmol) of Raw Material Compound 5, 407 mg (0.35 mmol) of tetrakistriphenylphosphine palladium, 2.92 g (21.1 mmol) of potassium carbonate and 7 mg of dibutylhydroxytoluene, and the mixture was stirred at an external temperature of 90° C. for 12 hours in a nitrogen atmosphere. After allowing to cool to room temperature, the reaction solution was extracted with ethyl acetate, concentrated in a rotary evaporator and purified on a silica gel column (ethyl acetate:hexane=1:4) to obtain 3.00 g (yield: 78%) of white Compound 12. Compound 12 obtained was confirmed to be the target product by $^1$H NMR.

$^1$H NMR (CDCl3) 7.87 (d, 4H), 7.72 (m, 4H), 7.59-7.54 (m, 2H), 7.50 (d, 2H), 7.34 (d, 1H), 7.01 (d, 2H), 6.17 (s, 1H), 5.61 (s, 1H), 4.54 (t, 2H), 4.32 (t, 2H), 2.38 (s, 3H), 1.97 (s, 3H).

Synthesis of D-77

26 g of propylene glycol monomethyl mether acetate was added to 2.45 g (4.50 mmol) of Raw Material Compound 12 and 4.06 g (40.6 mmol) of methyl methacrylate, and the mixture was stirred at an external temperature of 80° C. in a nitrogen atmosphere. Thereto, 104 mg (0.40 mmol) of 2,2'-azobis(2,4-dimethylvaleronitrile) dissolved in 2 ml of propylene glycol monomethyl mether acetate was added and after stirring for 2 hours, 51.8 mg (0.20 mmol) of 2,2'-azobis(2,4-dimethylvaleronitrile) dissolved in 2 ml of propylene glycol monomethyl mether acetate was added, followed by stirring for 2 hours. Furthermore, 51.8 mg (0.20 mmol) of 2,2'-azobis(2,4-dimethylvaleronitrile) dissolved in 2 ml of propylene glycol monomethyl mether acetate was added, and the mixture was stirred for 2 hours. Thereafter, the external temperature was raised to 90° C., and the system was stirred for 1 hour. After allowing to cool to room temperature, the reaction solution was poured in methanol under stirring to perform crystallization, then filtered and dried under reduced pressure to obtain 5.13 g of a compound. The composition of the polymer obtained was confirmed by $^1$H NMR, and the molecular weight was measured by GPC (compositional ratio: Raw Material Compound 12/methyl methacrylate=8.6/91.4 (by mol), Mw=30,000).

Production of Two-Photon Absorption Recording Mediums 9 and 10

Based on the preparation method for Two-Photon Absorption Recording Medium 5, Two-Photon Absorption Recording Medium 9 was prepared using Polymer Two-Photon Absorption Compound D-77 synthesized in the same manner as D-1, and Two-Photon Absorption Recording Medium 10 was prepared using R-1 and polymethyl acrylate, similarly to Two-Photon Absorption Recording Medium 6.

Evaluation of Change in Height of Recording Mark by Humidity-Heat Storage Test after Two-Photon Recording With respect to the recorded part in the recording layer using each of Two-Photon Absorption Recording Mediums 9 and 10 after two-photon absorption recording, a humidity-heat storage test at 60° C. and 90% RH was performed, as a result, the recording mark of Two-Photon Absorption Recording Material 10 using R-1 disappeared in 2 hours. On the other hand, reduction in the height of the recording mark of Two-Photon Absorption Recording Material 9 using D-77 stayed at 26% after 300 hours.

Evaluation of Change in Intensity of Reflected Light by Humidity-Heat Storage Test of Unrecorded Part With respect to the unrecorded part in the recording layer using each of Two-Photon Absorption Recording Mediums 9 and 10 after two-photon absorption recording, a humidity-heat storage test for 300 hours was performed. Assuming that the intensity of each reflected light before the test is 100, the relative change in the intensity of reflected light between before and after the test is shown in Table 3 below.

TABLE 3

Evaluation by Humidity-Heat Storage Test of Two-Photon Absorption Recording Medium

| Recording Medium | Humidity-Heat Storage Conditions | Relative Change in Intensity of Reflected Light | |
|---|---|---|---|
| | | Before Test | After Test of 300 Hours |
| Two-Photon Absorption Recording Medium 9 | 60° C., 90% RH | 100 | 95 |
| | 80° C., 85% RH | 100 | 100 |
| Two-Photon Absorption Recording Medium 10 | 60° C., 90% RH | 100 | 56 |
| | 80° C., 85% RH | 100 | 59 |

As seen from the evaluation of change in mark height and the results in Table 3, Two-Photon Absorption Recording Material 9 using Compound D-77 of the present invention has higher humidity-heat resistance than Two-Photon Absorption Recording Material 10 using Comparative Compound R-1.

Example 5

Synthesis Method of Compound D-273

Compound D-273 was synthesized by the following method.

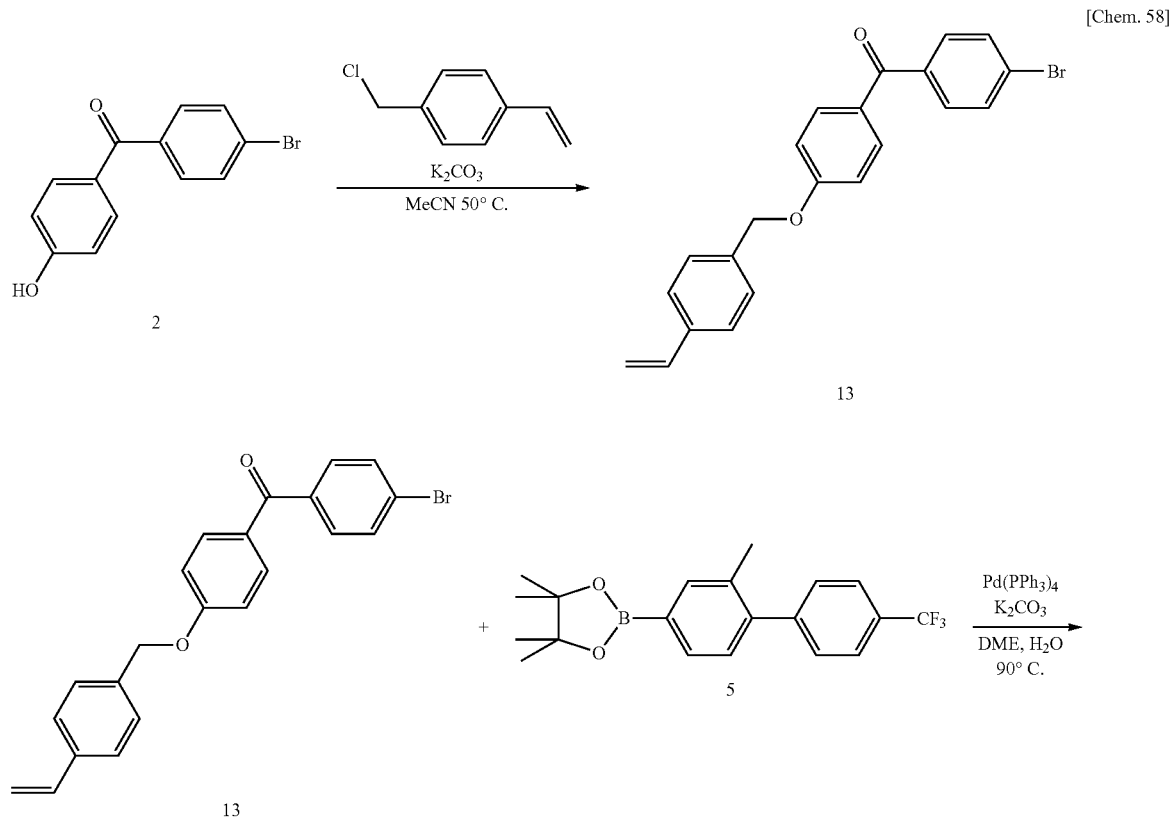

[Chem. 58]

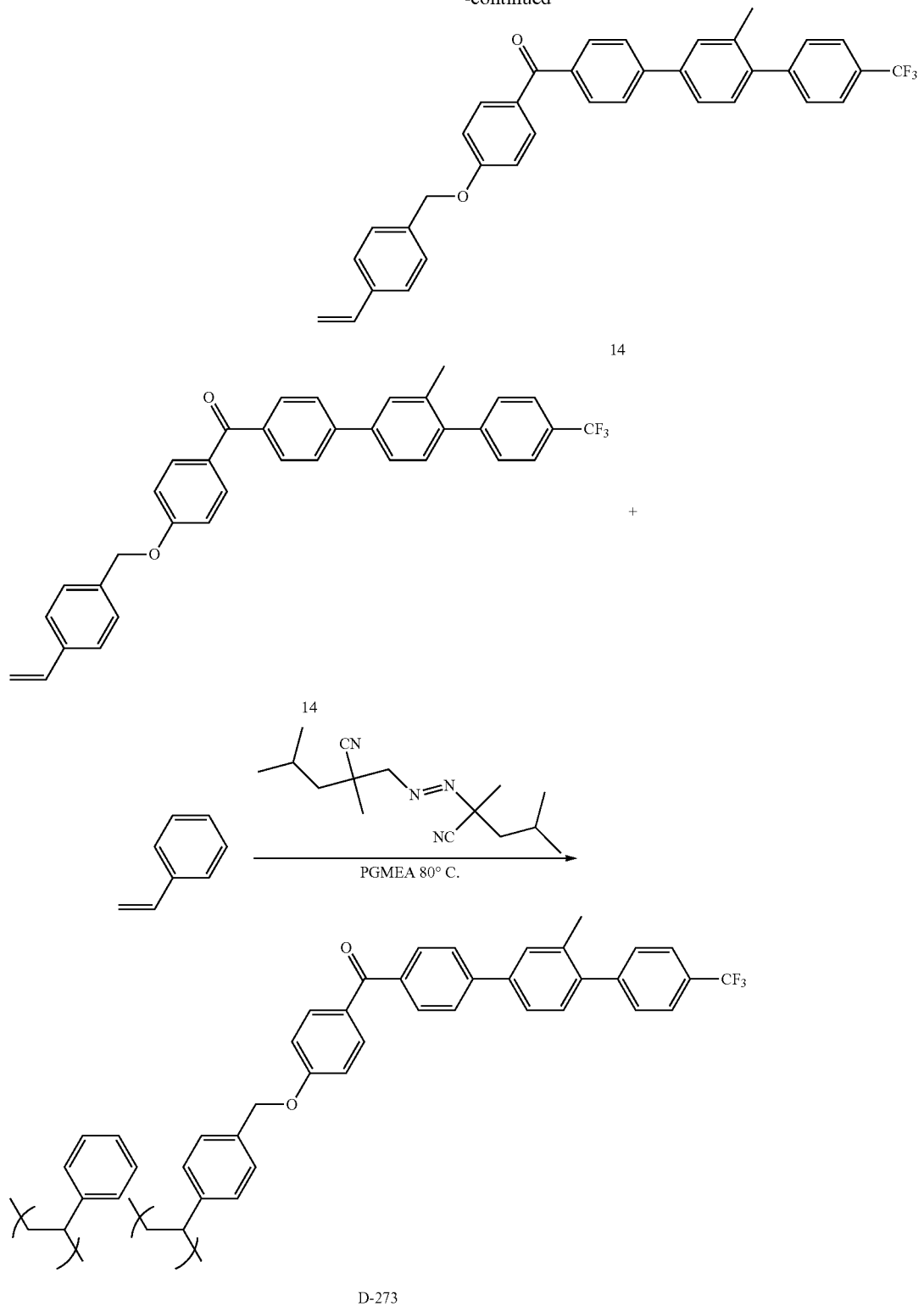

D-273

Synthesis of Raw Material Compound 13

100 ml of acetonitrile was added to 8.00 g (28.9 mmol) of Raw Material Compound 2 and 7.99 g (57.8 mmol) of potassium carbonate, and the mixture was stirred at an external temperature of 50° C. for 1 hour in a nitrogen atmosphere. Thereafter, the system was further stirred for 30 hours while adding dropwise 4.85 g (31.8 mmol) of 4-vinylbenzyl chloride. The reaction solution was poured in water and stirred at room temperature for 20 minutes. The precipitate deposited was separated by filtration and purified on a silica gel column to obtain 5.11 g (yield: 45%) of white Compound 13. Compound 13 obtained was confirmed to be the target product by $^1$H NMR.

Synthesis of Raw Material Compound 14

35 ml of dimethoxyethane and 7 ml of water were added to 3.00 g (7.63 mmol) of Raw Material Compound 13, 3.04 g (8.39 mmol) of Raw Material Compound 5, 439 mg (0.38 mmol) of tetrakistriphenylphosphine palladium, 3.17 g (22.9 mmol) of potassium carbonate and 7 mg of dibutylhydroxytoluene, and the mixture was stirred at an external temperature of 90° C. for 12 hours in a nitrogen atmosphere. After allowing to cool to room temperature, the reaction solution was extracted with ethyl acetate, concentrated in a rotary evaporator and purified on a silica gel column (ethyl acetate: hexane=1:4) to obtain 2.72 g (yield: 65%) of white Compound 14. Compound 14 obtained was confirmed to be the target product by $^1$H NMR.

Synthesis of D-273

24.4 g of propylene glycol monomethyl mether acetate was added to 1.73 g (3.15 mmol) of Raw Material Compound 14 and 4.36 g (41.9 mmol) of styrene, and the mixture was stirred at an external temperature of 80° C. in a nitrogen atmosphere. Thereto, 104 mg (0.40 mmol) of 2,2'-azobis(2,4-dimethylvaleronitrile) dissolved in 2 ml of propylene glycol monomethyl mether acetate was added and after stirring for 2 hours, 51.8 mg (0.20 mmol) of 2,2'-azobis(2,4-dimethylvaleronitrile) dissolved in 2 ml of propylene glycol monomethyl mether acetate was added, followed by stirring for 2 hours. Furthermore, 51.8 mg (0.20 mmol) of 2,2'-azobis(2,4-dimethylvaleronitrile) dissolved in 2 ml of propylene glycol monomethyl mether acetate was added, and the mixture was stirred for 2 hours. Thereafter, the external temperature was raised to 90° C., and the system was stirred for 1 hour. After allowing to cool to room temperature, the reaction solution was poured in methanol under stirring to perform crystallization, then filtered and dried under reduced pressure to obtain 4.89 g of a compound. The composition of the polymer obtained was confirmed by $^1$H NMR, and the molecular weight was measured by GPC (compositional ratio: Raw Material Compound 14/styrene=9.5/90.5 (by mol), Mw=43,000).

Production of Two-Photon Absorption Recording Mediums 11 and 12

Based on the preparation method for Two-Photon Absorption Recording Medium 5, Two-Photon Absorption Recording Medium 11 was prepared using Polymer Two-Photon Absorption Compound D-273 synthesized in the same manner as D-1, and Two-Photon Absorption Recording Medium 12 was prepared using R-1 and polymethyl acrylate, similarly to Two-Photon Absorption Recording Medium 6.

Evaluation of Change in Height of Recording Mark by Humidity-Heat Storage Test after Two-Photon Recording With respect to the recorded part in the recording layer using each of Two-Photon Absorption Recording Mediums 11 and 12 after two-photon absorption recording, a humidity-heat storage test at 60° C. and 90% RH was performed, as a result, the recording mark of Two-Photon Absorption Recording Material 12 using R-1 disappeared in 27 hours. On the other hand, reduction in the height of the recording mark of Two-Photon Absorption Recording Material 11 using D-273 stayed at 7% after 300 hours.

Evaluation of Change in Intensity of Reflected Light by Humidity-Heat Storage Test of Unrecorded Part With respect to the unrecorded part in the recording layer using each of Two-Photon Absorption Recording Mediums 11 and 12 after two-photon absorption recording, a humidity-heat storage test for 300 hours was performed. Assuming that the intensity of each reflected light before the test is 100, the relative change in the intensity of reflected light between before and after the test is shown in Table 4 below.

[Table 4]

TABLE 4

Evaluation by Humidity-Heat Storage Test of Two-Photon Absorption Recording Medium

| Recording Medium | Humidity-Heat Storage Conditions | Relative Change in Intensity of Reflected Light | |
|---|---|---|---|
| | | Before Test | After Test of 300 Hours |
| Two-Photon Absorption Recording Medium 11 | 60° C., 90% RH | 100 | 100 |
| | 80° C., 85% RH | 100 | 104 |
| Two-Photon Absorption Recording Medium 12 | 60° C., 90% RH | 100 | 87 |
| | 80° C., 85% RH | 100 | 88 |

As seen from the evaluation of change in mark height and the results in Table 4, Two-Photon Absorption Recording Material 11 using Compound D-273 of the present invention has higher humidity-heat resistance than Two-Photon Absorption Recording Material 12 using Comparative Compound R-1.

Example 6

Production of Two-Photon Absorption Recording Mediums 13 and 14

Based on the preparation method for Two-Photon Absorption Recording Medium 5, Two-Photon Absorption Recording Medium 13 was prepared using Polymer Two-Photon Absorption Compound D-3 synthesized in the same manner as D-1, and Two-Photon Absorption Recording Medium 14 was prepared using R-1 and polymethyl acrylate, similarly to Two-Photon Absorption Recording Medium 6.

Evaluation of Change in Height of Recording Mark by Humidity-Heat Storage Test after Two-Photon Recording With respect to the recorded part in the recording layer using each of Two-Photon Absorption Recording Mediums 13 and 14 after two-photon absorption recording, a humidity-heat storage test at 30° C. and 90% RH was performed, as a result, the recording mark of Two-Photon Absorption Recording Material 14 using R-1 disappeared in 27 hours. On the other hand, reduction in the height of the recording mark of Two-Photon Absorption Recording Material 13 using D-3 stayed at 5% after 300 hours.

Evaluation of Change in Intensity of Reflected Light by Humidity-Heat Storage Test of Unrecorded Part With respect to the unrecorded part in the recording layer using each of Two-Photon Absorption Recording Mediums 13 and 14 after two-photon absorption recording, a humidity-heat storage test for 300 hours was performed. Assuming that the intensity of each reflected light before the test is 100, the relative change in the intensity of reflected light between before and after the test is shown in Table 5 below.

TABLE 5

Evaluation by Humidity-Heat Storage Test of Two-Photon Absorption Recording Medium

| Recording Medium | Humidity-Heat Storage Conditions | Before Test | After Test of 300 Hours |
|---|---|---|---|
| Two-Photon Absorption Recording Medium 13 | 30° C., 90% RH | 100 | 100 |
|  | 50° C., 85% RH | 100 | 88 |
| Two-Photon Absorption Recording Medium 14 | 30° C., 90% RH | 100 | 5 |
|  | 50° C., 85% RH | 100 | 3 |

As seen from the evaluation of change in mark height and the results in Table 5, Two-Photon Absorption Recording Material 13 using Compound D-3 of the present invention has higher humidity-heat resistance than Two-Photon Absorption Recording Material 14 using Comparative Compound R-1.

Example 7

Synthesis Method of Compound D-106

Compound D-106 was synthesized by the following method.

[Chem. 59]

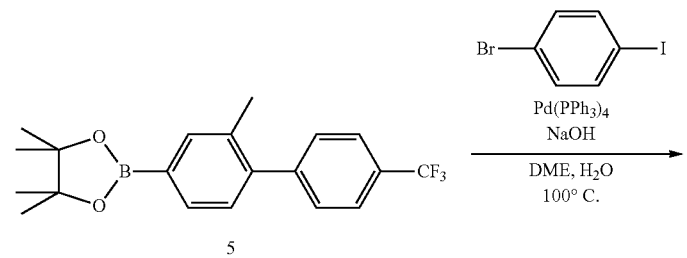

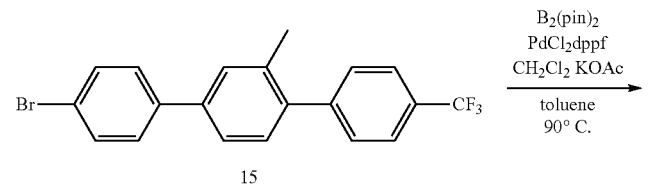

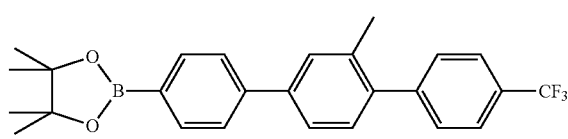

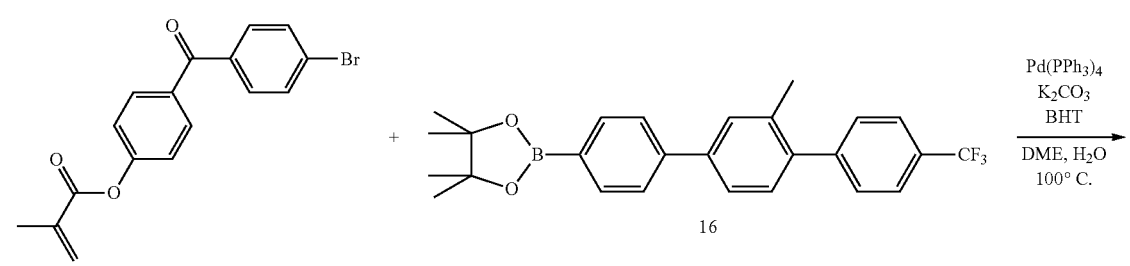

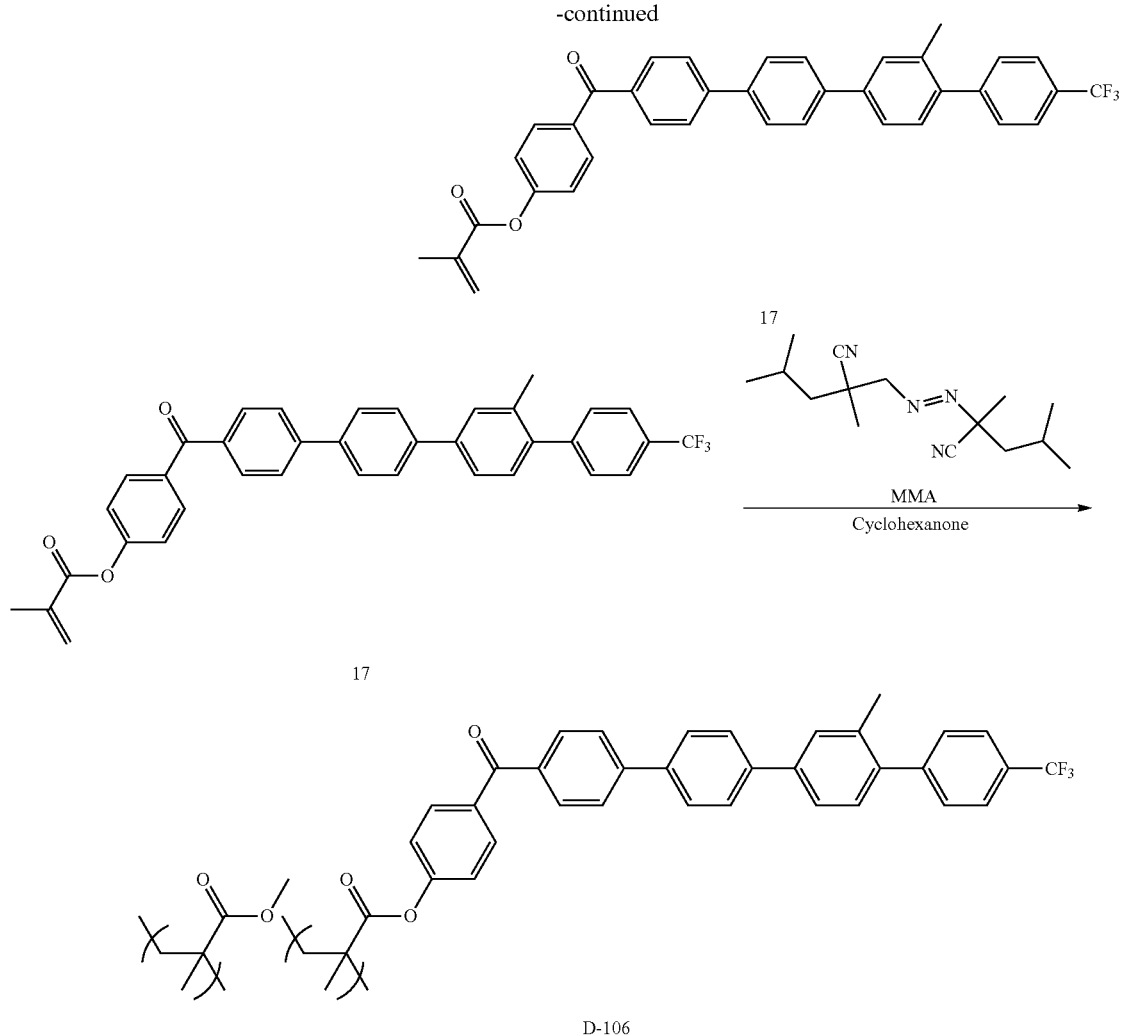

D-106

Synthesis of Raw Material Compound 15

97 ml of 1,2-dimethoxyethane and 35 ml of pure water were added to 11.0 g (30.4 mmol) of Raw Material Compound 5, 8.20 g (29.0 mmol) of 4-iodobromobenzene, 1.68 g (1.45 mmol) of tetrakistriphenylphosphine palladium and 3.48 g (87.0 mmol) of sodium hydroxide, and the mixture was stirred at an external temperature of 100° C. for 3 hours in a nitrogen atmosphere. After allowing to cool to room temperature, the reaction solution was poured in water, and the precipitate produced was filtered and used still as being a crude product in the subsequent reaction.

Synthesis of Raw Material Compound 16

90 ml of toluene was added to 13.0 g (33.2 mmol) of Raw Material Compound 15, 9.27 g (36.5 mmol) of bispinacolatodiboron, 1.36 g (1.66 mmol) of [1,1'-bis(diphenylphosphino)ferrocene]palladium(II) dichloride dichloromethane adduct and 9.77 g (99.6 mmol) of potassium acetate, and the mixture was stirred at an external temperature of 90° C. for 6 hours. After allowing to cool to room temperature, the reaction solution was extracted with ethyl acetate, concentrated in a rotary evaporator and then purified on a silica gel column (hexane: ethyl acetate=10:1) to obtain 8.26 g (yield in two steps: 65%) of white Compound 16. The compound obtained was confirmed to be the target product by $^1$H NMR spectrum.

Synthesis of Raw Material Compound 17

31 ml of dimethoxyethane and 6 ml of pure water were added to 2.15 g (6.22 mmol) of Raw Material Compound 3, 3.00 g (6.84 mmol) of Raw Material Compound 16, 359 mg (0.311 mmol) of tetrakistriphenylphosphine palladium, 2.58 g (18.7 mmol) of potassium carbonate and 14 mg of dibutylhydroxytoluene, and the mixture was stirred at an external temperature of 100° C. for 4 hours in a nitrogen atmosphere. After allowing to cool to room temperature, the reaction solution was poured in water and stirred at room temperature for 20 minutes. The precipitate deposited was filtered, washed in sequence with hexane: ethyl acetate=1:1 and then with methanol, filtered and dried to obtain 1.68 g (yield: 47%) of a white compound. The compound obtained was confirmed to be the target product by $^1$H NMR spectrum.

$^1$H NMR (CDCl$_3$): 7.93-7.91 (m, 4H), 7.79-7.77 (m, 6H), 7.71 (d, 2H), 7.59-7.55 (m, 2H), 7.50 (d, 2H), 7.33 (d, 1H), 7.29 (d, 2H), 6.41 (s, 1H), 5.82 (t, 1H), 2.37 (s, 3H), 2.10 (s, 3H).

Synthesis of D-106

24 g of cyclohexanone was added to 1.81 g (3.15 mmol) of raw material compound and 4.19 g (41.9 mmol) of methyl methacrylate, and the mixture was stirred at an external temperature of 80° C. in a nitrogen atmosphere. After 30 minutes, 103.6 mg (0.450 mmol) of 2,2'-azobis(2,4-dimethylvaleronitrile) was added, and the mixture was stirred for 2 hours. Thereafter, 51.8 mg (0.225 mmol) of 2,2'-azobis(2,4-dimethylvaleronitrile) was added, followed by stirring for 2 hours. Furthermore, 51.8 mg (0.225 mmol) of 2,2'-azobis(2,4-dimethylvaleronitrile) was added, and the mixture was further stirred for 2 hours and finally stirred for 2 hours by raising the external temperature to 90° C. After allowing to cool to room temperature, the reaction solution was poured in methanol under stirring to perform crystallization, then filtered and dried under reduced pressure to obtain 4.16 g of a compound. The composition of the polymer obtained was confirmed by $^1$H NMR spectrum, and the molecular weight was measured by GPC (compositional ratio: Raw Material Compound 1/methyl methacrylate=8.6/91.4 (by mol), Mw=30,000).

Synthesis of Comparative Compound R-2

[Chem. 60]

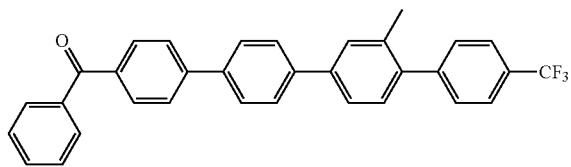

Comparative Compound R-2

Compound R-2 was synthesized by the following method.

[Chem. 61]

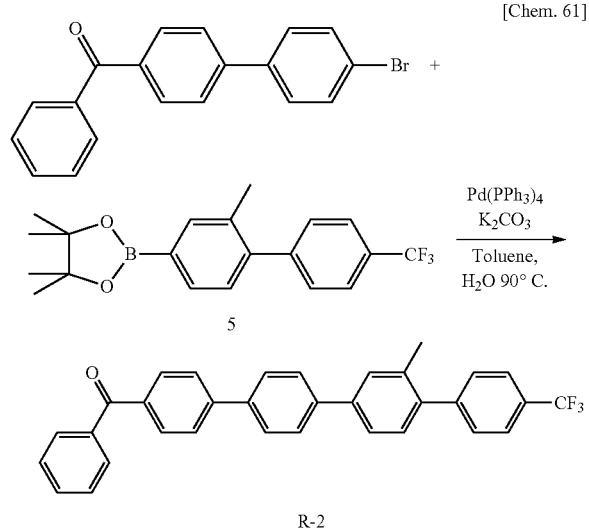

Synthesis of R-2

60 ml of toluene and 10 ml of water were added to 5.00 g (14.8 mmol) of 4-benzoyl-4'-bromobiphenyl, 5.90 g (16.3 mmol) of Raw Material Compound 5, 855 mg (0.74 mmol) of tetrakistriphenylphosphine palladium and 6.14 g (44.4 mmol) of potassium carbonate, and the mixture was stirred at an external temperature of 90° C. for 12 hours in a nitrogen atmosphere. After allowing to cool to room temperature, the reaction solution was extracted with ethyl acetate, concentrated in a rotary evaporator and purified on a silica gel column (ethyl acetate: hexane=1:4) to obtain 5.47 g (yield: 75%) of white Compound R-2. Compound R-2 obtained was confirmed to be the target product by H NMR.

$^1$H NMR (CDCl3) 7.93 (d, 2H), 7.86 (d, 2H), 7.80-7.69 (m, 8H), 7.64-7.49 (m, 7H), 7.33 (d, 1H), 2.37 (s, 3H).

Production of Two-Photon Absorption Recording Mediums 15 and 16

Based on the preparation method for Two-Photon Absorption Recording Medium 5, Two-Photon Absorption Recording Medium 15 was prepared using Polymer Two-Photon Absorption Compound D-106 synthesized in the same manner as D-1, and Two-Photon Absorption Recording Medium 16 was prepared using R-1 and polymethyl acrylate, similarly to Two-Photon Absorption Recording Medium 6.

Evaluation of Change in Height of Recording Mark by Humidity-Heat Storage Test after Two-Photon Recording With respect to the recorded part in the recording layer using each of Two-Photon Absorption Recording Mediums 15 and 16 after two-photon absorption recording, a humidity-heat storage test at 60° C. and 90% RH was performed, as a result, the recording mark of Two-Photon Absorption Recording Material 16 disappeared in 2 hours. On the other hand, reduction in the height of the recording mark of Two-Photon Absorption Recording Material 15 stayed at 10% after 300 hours.

Evaluation of Change in Intensity of Reflected Light by Humidity-Heat Storage Test of Unrecorded Part With respect to the unrecorded part in the recording layer using each of Two-Photon Absorption Recording Materials 1 and 2 after two-photon absorption recording, a humidity-heat storage test for 300 hours was performed. Assuming that the intensity of each reflected light before the test is 100, the relative change in the intensity of reflected light between before and after the test is shown in Table 6 below.

TABLE 6

Evaluation by Humidity-Heat Storage Test of Two-Photon Absorption Recording Medium

| Recording Medium | Humidity-Heat Storage Conditions | Relative Change in Intensity of Reflected Light | |
|---|---|---|---|
| | | Before Test | After Test of 300 Hours |
| Two-Photon Absorption Recording Medium 15 | 60° C., 90% RH | 100 | 100 |
| | 80° C., 85% RH | 100 | 105 |
| Two-Photon Absorption Recording Medium 16 | 60° C., 90% RH | 100 | 5 |
| | 80° C., 85% RH | 100 | 0 |

As seen in Table 6, Two-Photon Absorption Recording Material 15 using Compound D-106 of the present invention has higher humidity-heat resistance than Two-Photon Absorption Recording Material 16 using Comparative Compound R-2.

INDUSTRIAL APPLICABILITY

According to the present invention, a two-photon absorption recording material allowing for non-resonant two-photon absorption recording and having high humidity/heat resistance can be provided.

While the invention has been described in detail and with reference to specific embodiments thereof, it will be apparent to one skilled in the art that various changes and modifications can be made therein without departing from the spirit and scope of the invention.

This application is based on Japanese Patent Application (Patent Application No. 2011-108698) filed on May 13, 2011, Japanese Patent Application (Patent Application No. 2011-154893) filed on Jul. 13, 2011, and Japanese Patent Application (Patent Application No. 2012-108951) filed on May 10, 2012, the contents of which are incorporated herein by way of reference.

DESCRIPTION OF REFERENCE NUMERALS AND SIGNS

1 Recording/reproducing apparatus
10 Optical information recording medium

The invention claimed is:

1. A non-resonant two-photon absorption recording medium consisting essentially of a non-resonant polymer two-photon absorption compound coated as a recording layer upon a substrate,
wherein:
the non-resonant polymer two-photon absorption compound is a polymer compound containing, as a copolymer component, a structure represented by the following formula (1):

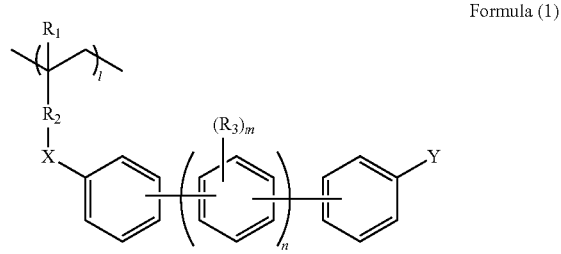

Formula (1)

and the polymer compound contains the structure

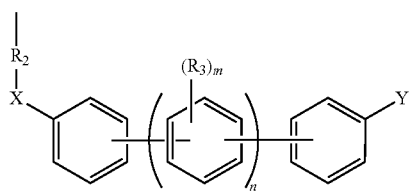

at a side chain thereof,
wherein Y represents a substituent having a Hammett sigma para value ($\sigma p$ value) of 0 or more; X represents a divalent substituent having a Hammett sigma para value ($\sigma p$ value) of 0 or more; X and Y may be the same as or different from each other; n represents an integer of 1 to 4; $R_1$ represents a hydrogen atom or a substituent; $R_2$ represents a divalent substituent; $R_3$ represents a substituent; when a plurality of $R_1$, $R_2$ or $R_3$ are present, $R_1$, $R_2$ or $R_3$ may be the same as or different from every other $R_1$, $R_2$ or $R_3$; l represents an integer of 1 or more; and m represents an integer of 0 to 4;
and further wherein:
the non-resonant polymer two-photon absorption compound is a material capable of changing the reflected light intensity or refractive index between before and after two-photon recording by deforming before and after two-photon recording to form a convex geometry on an interface with a layer adjacent to a recording layer containing the non-resonant polymer two-photon absorption compound.

2. The optical information recording medium as claimed in claim 1, wherein the thickness of the recording layer is from 50 nm to 5 μm.

3. The optical information recording medium as claimed in claim 1, wherein the optical recording medium has an intermediate layer located adjacent to the recording layer so as to physically separate the recording layer and form an interface capable of forming a recording mark by expansion.

4. The optical information recording medium as claimed in claim 3, wherein the refractive index difference between the recording layer and the intermediate layer is from 0.01 to 0.5.

5. The optical information recording medium as claimed in claim 3, wherein the thickness of the intermediate layer is from 2 to 20 μm.

6. The optical information recording medium as claimed in claim 1, wherein the substrate thickness is from 0.02 to 2 mm.

7. The optical information recording medium as claimed in claim 1, wherein the optical information recording medium has a guide layer for performing the radial position control by a tracking servo during recording.

8. The optical information recording medium as claimed in claim 1, wherein the optical information recording medium has a cover layer on the light incidence-side surface side relative to the recording layer.

9. The optical information recording medium as claimed in claim 8, wherein the thickness of the cover layer is from 0.01 mm to 0.2 mm.

10. The optical information recording medium as claimed in claim 1, wherein the optical information recording medium has a reflecting layer.

11. The optical information recording medium as claimed in claim 1, wherein the optical information recording medium has a spacer layer.

12. The optical information recording medium as claimed in claim 11, wherein the thickness of the spacer layer is from 5 μm to 100 μm.

13. The optical information recording medium as claimed in claim 1, wherein the optical information recording medium performs marking.

14. The optical information recording medium as claimed in claim 1, wherein the optical information recording medium has a hardcoat layer on the light incidence-side surface.

15. The optical information recording medium as claimed in claim 1, wherein the optical information recording medium is housed in a cartridge.

16. A recording/reproducing method on the optical information recording medium claimed in claim 1, wherein the peak power of a recording laser is from 1 to 100 W on the surface of the optical information recording medium, the average power of the recording laser is 100 mW or less on the surface of the optical information recording medium, and the product of the pulse width and the oscillation cycle of the recording laser is from 0.001 to 0.1.

17. A recording/reproducing method on the optical information recording medium claimed in claim 1, comprising using a confocal optical system at the time of reproducing the information.

18. The non-resonant two-photon absorption recording medium as claimed in claim 1, wherein the polymer compound containing, as a copolymer component, a structure represented by formula (1) is a polymer compound containing, as a copolymer component, a structure represented by the following formula (2):

Formula (2)

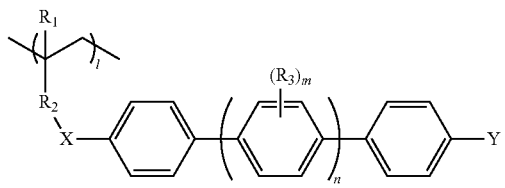

wherein Y represents a substituent having a Hammett sigma para value (σp value) of 0 or more; X represents a divalent substituent having a Hammett sigma para value (σp value) of 0 or more; X and Y may be the same as or different from each other; n represents an integer of 1 to 4; $R_1$ represents a hydrogen atom or a substituent; $R_2$ represents a divalent substituent; $R_3$ represents a substituent; when a plurality of $R_1$, $R_2$ or $R_3$ are present, $R_1$, $R_2$ or $R_3$ may be the same as or different from every other $R_1$, $R_2$ or $R_3$; l represents an integer of 1 or more; and m represents an integer of 0 to 4.

19. The non-resonant two-photon absorption recording medium as claimed in claim 1, wherein the polymer compound containing, as a copolymer component, a structure represented by formula (1) is a polymer compound containing, as a copolymer component, a structure represented by the following formula (3):

Formula (3)

wherein Y represents a substituent having a Hammett sigma para value (σp value) of 0 or more; n represents an integer of 1 to 4; $R_1$ represents a hydrogen atom or a substituent; $R_2$ represents a divalent substituent; $R_3$ represents a substituent; when a plurality of $R_1$, $R_2$ or $R_3$ are present, $R_1$, $R_2$ or $R_3$ may be the same as or different from every other $R_1$, $R_2$ or $R_3$; l represents an integer of 1 or more; and m represents an integer of 0 to 4.

20. The non-resonant two-photon absorption recording medium as claimed in claim 1, wherein the polymer compound containing, as a copolymer component, a structure represented by formula (1) is a polymer compound containing, as a copolymer component, a structure represented by the following formula (4):

Formula (4)

wherein Y represents a substituent having a Hammett sigma para value (σp value) of 0 or more; n represents an integer of 1 to 4; $R_1$ represents a hydrogen atom or a substituent; $R_2$ represents a divalent substituent; $R_3$ represents a substituent; when a plurality of $R_1$, $R_2$ or $R_3$ are present, $R_1$, $R_2$ or $R_3$ may be the same as or different from every other $R_1$, $R_2$ or $R_3$; l represents an integer of 1 or more; and m represents an integer of 0 to 4.

21. The non-resonant two-photon absorption recording medium as claimed in claim 1, the weight average molecular weight of the non-resonant polymer two-photon absorption compound represented by formula (1) is from 10,000 to 700,000.

22. The non-resonant two-photon absorption recording medium as claimed in claim 1, wherein the molecular weight distribution (weight average molecular weight÷number average molecular weight, Mw/Mn) of the non-resonant polymer two-photon absorption compound represented by formula (1) is 5.0 or less.

23. The non-resonant two-photon absorption recording medium as claimed in claim 1, wherein the non-resonant polymer two-photon absorption compound is a polymer compound containing, as copolymer components, a structure represented by formula (1) as a first repeating unit and a second repeating unit other than the first repeating unit, and the percentage of the first repeating unit is from 1 to 80 mol %.

24. The non-resonant two-photon absorption recording medium as claimed in claim 1, wherein the non-resonant polymer two-photon absorption compound can change the reflected light intensity between before and after two-photon recording in a recording layer formed of the recording material.

25. The non-resonant two-photon absorption recording medium as claimed in claim 1, wherein the non-resonant polymer two-photon absorption compound can change the refractive index between before and after two-photon recording in a recording layer formed of the recording material.

* * * * *